(12) United States Patent
Cooley et al.

(10) Patent No.: US 12,168,147 B2
(45) Date of Patent: Dec. 17, 2024

(54) COLLIMATOR AND ENERGY DEGRADER FOR A PARTICLE THERAPY SYSTEM

(71) Applicant: Mevion Medical Systems, Inc., Littleton, MA (US)

(72) Inventors: James Cooley, Boxborough, MA (US); Townsend Zwart, Durham, NH (US); Mark Jones, Reading, MA (US); Michael Ahearn, Sandown, NH (US)

(73) Assignee: Mevion Medical Systems, Inc., Littleton, CO (US)

( * ) Notice: Subject to any disclaimer, the term of this patent is extended or adjusted under 35 U.S.C. 154(b) by 0 days.

(21) Appl. No.: 17/728,098

(22) Filed: Apr. 25, 2022

(65) Prior Publication Data

US 2022/0249871 A1    Aug. 11, 2022

Related U.S. Application Data

(63) Continuation of application No. 16/811,138, filed on Mar. 6, 2020, now Pat. No. 11,311,746.

(Continued)

(51) Int. Cl.
 *A61N 5/10* (2006.01)

(52) U.S. Cl.
 CPC ......... *A61N 5/1045* (2013.01); *A61N 5/1031* (2013.01); *A61N 5/1043* (2013.01);

(Continued)

(58) Field of Classification Search
 None
 See application file for complete search history.

(56) References Cited

U.S. PATENT DOCUMENTS 463,291 A    11/1891    Dodson
773,508 A    10/1904    Leblanc
(Continued)

FOREIGN PATENT DOCUMENTS

CA    2629333 A1    5/2007
CN    1377521 A    10/2002
(Continued)

OTHER PUBLICATIONS

International Preliminary Report on Patentability for International Patent Application No. PCT/US2020/021342, Issued Sep. 23, 2021, (12 Pages.).

(Continued)

*Primary Examiner* — Marcus H Taningco
(74) *Attorney, Agent, or Firm* — ArentFox Schiff, LLP

(57) ABSTRACT

An example system includes a particle accelerator to produce a particle beam to treat a patient and a carrier having openings including a first opening and a second opening. The carrier is made of a material that inhibits transmission of the particle beam and the carrier is located between the particle accelerator and the patient. A control system is configured to control movement of the particle beam to the first opening to enable at least part of the particle beam to reach the patient, to change an energy of the particle beam while the particle beam remains stationary at the first opening, and to control movement of the particle beam from the first opening to the second opening. The example system also includes an energy degrader that includes at least some boron carbide.

21 Claims, 48 Drawing Sheets

Related U.S. Application Data

(60) Provisional application No. 62/889,861, filed on Aug. 21, 2019, provisional application No. 62/889,825, filed on Aug. 21, 2019, provisional application No. 62/853,387, filed on May 28, 2019, provisional application No. 62/815,721, filed on Mar. 8, 2019.

(52) U.S. Cl.
CPC ......... *A61N 5/1065* (2013.01); *A61N 5/1079* (2013.01); *A61N 2005/1087* (2013.01)

(56) References Cited

U.S. PATENT DOCUMENTS

| | | |
|---|---|---|
| 2,280,606 A | 4/1942 | Roberts |
| 2,492,324 A | 12/1949 | Salisbury |
| 2,615,129 A | 10/1952 | Mcmillan |
| 2,616,042 A | 10/1952 | Ray |
| 2,659,000 A | 11/1953 | Salisbury |
| 2,701,304 A | 2/1955 | Dickinson |
| 2,754,422 A | 7/1956 | Lofgren et al. |
| 2,789,222 A | 4/1957 | Martin et al. |
| 2,958,327 A | 11/1960 | Geissmann |
| 3,175,131 A | 3/1965 | Burleigh et al. |
| 3,432,721 A | 3/1969 | Naydan et al. |
| 3,582,650 A | 6/1971 | Avery |
| 3,679,899 A | 7/1972 | Dimeff |
| 3,689,847 A | 9/1972 | Verster |
| 3,757,118 A | 9/1973 | Hodge et al. |
| 3,868,522 A | 2/1975 | Bigham et al. |
| 3,886,367 A | 5/1975 | Castle, Jr. |
| 3,925,676 A | 12/1975 | Bigham et al. |
| 3,955,089 A | 5/1976 | McIntyre et al. |
| 3,958,327 A | 5/1976 | Marancik et al. |
| 3,992,625 A | 11/1976 | Schmidt et al. |
| 4,038,622 A | 7/1977 | Purcell |
| 4,047,068 A | 9/1977 | Ress et al. |
| 4,112,306 A | 9/1978 | Nunan |
| 4,129,784 A | 12/1978 | Tschunt et al. |
| 4,139,777 A | 2/1979 | Rautenbach |
| 4,197,510 A | 4/1980 | Szu |
| 4,220,866 A | 9/1980 | Taumann et al. |
| 4,230,129 A | 10/1980 | LeVeen |
| 4,256,966 A | 3/1981 | Heinz |
| 4,293,772 A | 10/1981 | Stieber |
| 4,336,505 A | 6/1982 | Meyer |
| 4,342,060 A | 7/1982 | Gibson |
| 4,345,210 A | 8/1982 | Tran |
| 4,353,033 A | 10/1982 | Karasawa |
| 4,425,506 A | 1/1984 | Brown et al. |
| 4,490,616 A | 12/1984 | Cipollina et al. |
| 4,507,614 A | 3/1985 | Prono et al. |
| 4,507,616 A | 3/1985 | Blosser et al. |
| 4,589,126 A | 5/1986 | Augustsson et al. |
| 4,598,208 A | 7/1986 | Brunelli et al. |
| 4,628,523 A | 12/1986 | Heflin |
| 4,633,125 A | 12/1986 | Blosser et al. |
| 4,641,057 A | 2/1987 | Blosser et al. |
| 4,641,104 A | 2/1987 | Blosser et al. |
| 4,651,007 A | 3/1987 | Perusek et al. |
| 4,680,565 A | 7/1987 | Jahnke |
| 4,705,955 A | 11/1987 | Mileikowsky |
| 4,710,722 A | 12/1987 | Jahnke |
| 4,726,046 A | 2/1988 | Nunan |
| 4,734,653 A | 3/1988 | Jahnke |
| 4,736,106 A | 4/1988 | Kashy et al. |
| 4,736,173 A | 4/1988 | Basil, Jr. et al. |
| 4,737,727 A | 4/1988 | Yamada et al. |
| 4,739,173 A | 4/1988 | Blosser |
| 4,745,367 A | 5/1988 | Dustmann et al. |
| 4,754,147 A | 6/1988 | Maughan et al. |
| 4,763,483 A | 8/1988 | Olsen |
| 4,767,930 A | 8/1988 | Stieber et al. |
| 4,769,623 A | 9/1988 | Marsing et al. |
| 4,771,208 A | 9/1988 | Jongen et al. |
| 4,783,634 A | 11/1988 | Yamamoto et al. |
| 4,808,941 A | 2/1989 | Marsing |
| 4,812,658 A | 3/1989 | Koehler |
| 4,843,333 A | 6/1989 | Marsing et al. |
| 4,845,371 A | 7/1989 | Stieber |
| 4,865,284 A | 9/1989 | Gosis et al. |
| 4,868,843 A | 9/1989 | Nunan |
| 4,868,844 A | 9/1989 | Nunan |
| 4,870,287 A | 9/1989 | Cole et al. |
| 4,880,985 A | 11/1989 | Jones |
| 4,894,541 A | 1/1990 | Ono |
| 4,896,206 A | 1/1990 | Denham |
| 4,902,993 A | 2/1990 | Krevet |
| 4,904,949 A | 2/1990 | Wilson |
| 4,905,267 A | 2/1990 | Miller et al. |
| 4,917,344 A | 4/1990 | Prechter et al. |
| 4,943,781 A | 7/1990 | Wilson et al. |
| 4,945,478 A | 7/1990 | Merickel et al. |
| 4,968,915 A | 11/1990 | Wilson et al. |
| 4,987,309 A | 1/1991 | Klasen et al. |
| 4,992,744 A | 2/1991 | Fujita et al. |
| 4,996,496 A | 2/1991 | Kitamura et al. |
| 5,006,759 A | 4/1991 | Krispel |
| 5,010,562 A | 4/1991 | Hernandez et al. |
| 5,012,111 A | 4/1991 | Ueda |
| 5,017,789 A | 5/1991 | Young et al. |
| 5,017,882 A | 5/1991 | Finlan |
| 5,036,290 A | 7/1991 | Sonobe et al. |
| 5,039,057 A | 8/1991 | Prechter et al. |
| 5,039,867 A | 8/1991 | Nishihara et al. |
| 5,046,078 A | 9/1991 | Hernandez et al. |
| 5,072,123 A | 12/1991 | Johnsen |
| 5,111,042 A | 5/1992 | Sullivan et al. |
| 5,111,173 A | 5/1992 | Matsuda et al. |
| 5,117,194 A | 5/1992 | Nakanishi et al. |
| 5,117,212 A | 5/1992 | Yamamoto et al. |
| 5,117,829 A | 6/1992 | Miller et al. |
| 5,148,032 A | 9/1992 | Hernandez |
| 5,166,531 A | 11/1992 | Huntzinger |
| 5,189,687 A | 2/1993 | Bova et al. |
| 5,191,706 A | 3/1993 | Cosden |
| 5,240,218 A | 8/1993 | Dye |
| 5,260,579 A | 11/1993 | Yasuda et al. |
| 5,260,581 A | 11/1993 | Lesyna et al. |
| 5,278,533 A | 1/1994 | Kawaguchi |
| 5,285,166 A | 2/1994 | Hiramoto et al. |
| 5,317,164 A | 5/1994 | Kurokawa |
| 5,336,891 A | 8/1994 | Crewe |
| 5,341,104 A | 8/1994 | Anton et al. |
| 5,349,198 A | 9/1994 | Takanaka |
| 5,365,742 A | 11/1994 | Boffito et al. |
| 5,374,913 A | 12/1994 | Pissantezky et al. |
| 5,382,914 A | 1/1995 | Hamm et al. |
| 5,401,973 A | 3/1995 | McKeown et al. |
| 5,405,235 A | 4/1995 | Lebre et al. |
| 5,434,420 A | 7/1995 | McKeown et al. |
| 5,440,133 A | 8/1995 | Moyers et al. |
| 5,451,794 A | 9/1995 | McKeown et al. |
| 5,461,773 A | 10/1995 | Kawaguchi |
| 5,463,291 A | 10/1995 | Carroll et al. |
| 5,464,411 A | 11/1995 | Schulte et al. |
| 5,492,922 A | 2/1996 | Palkowitz |
| 5,511,549 A | 4/1996 | Legg et al. |
| 5,521,469 A | 5/1996 | Laisne |
| 5,538,942 A | 7/1996 | Koyama et al. |
| 5,549,616 A | 8/1996 | Schulte et al. |
| 5,561,697 A | 10/1996 | Takafuji et al. |
| 5,585,642 A | 12/1996 | Britton et al. |
| 5,633,747 A | 5/1997 | Nikoonahad |
| 5,635,721 A | 6/1997 | Bardi et al. |
| 5,668,371 A | 9/1997 | Deasy et al. |
| 5,672,878 A | 9/1997 | Yao |
| 5,691,679 A | 11/1997 | Ackermann et al. |
| 5,726,448 A | 3/1998 | Smith et al. |
| 5,727,554 A | 3/1998 | Kalend et al. |
| 5,730,745 A | 3/1998 | Schulte et al. |
| 5,751,781 A | 5/1998 | Brown et al. |
| 5,778,047 A | 7/1998 | Mansfield et al. |
| 5,783,914 A | 7/1998 | Hiramoto et al. |

(56) References Cited

U.S. PATENT DOCUMENTS

| | | |
|---|---|---|
| 5,784,431 A | 7/1998 | Kalend et al. |
| 5,797,924 A | 8/1998 | Schulte et al. |
| 5,811,944 A | 9/1998 | Sampayan et al. |
| 5,818,058 A | 10/1998 | Nakanishi et al. |
| 5,821,705 A | 10/1998 | Caporaso et al. |
| 5,825,845 A | 10/1998 | Blair et al. |
| 5,841,237 A | 11/1998 | Alton |
| 5,846,043 A | 12/1998 | Spath |
| 5,851,182 A | 12/1998 | Sahadevan |
| 5,866,912 A | 2/1999 | Slater et al. |
| 5,874,611 A | 2/1999 | Finlan et al. |
| 5,895,926 A | 4/1999 | Britton et al. |
| 5,920,601 A | 7/1999 | Nigg et al. |
| 5,929,458 A | 7/1999 | Nemazawa et al. |
| 5,953,615 A | 10/1999 | Egley et al. |
| 5,993,373 A | 11/1999 | Nonaka et al. |
| 6,006,499 A | 12/1999 | Hiramoto et al. |
| 6,034,377 A | 3/2000 | Pu |
| 6,057,655 A | 5/2000 | Jongen |
| 6,061,426 A | 5/2000 | Linders et al. |
| 6,064,807 A | 5/2000 | Arai et al. |
| 6,066,851 A | 5/2000 | Madono et al. |
| 6,080,992 A | 6/2000 | Nonaka et al. |
| 6,087,670 A | 7/2000 | Hiramoto et al. |
| 6,094,760 A | 8/2000 | Nonaka et al. |
| 6,118,848 A | 9/2000 | Reiffel |
| 6,140,021 A | 10/2000 | Nakasuji et al. |
| 6,144,875 A | 11/2000 | Schweikard et al. |
| 6,158,708 A | 12/2000 | Egley et al. |
| 6,207,952 B1 | 3/2001 | Kan et al. |
| 6,219,403 B1 | 4/2001 | Nishihara |
| 6,222,905 B1 | 4/2001 | Yoda et al. |
| 6,241,671 B1 | 6/2001 | Ritter et al. |
| 6,246,066 B1 | 6/2001 | Yuehu |
| 6,256,591 B1 | 7/2001 | Yoda et al. |
| 6,265,837 B1 | 7/2001 | Akiyama et al. |
| 6,268,610 B1 | 7/2001 | Pu |
| 6,278,239 B1 | 8/2001 | Caporaso et al. |
| 6,279,579 B1 | 8/2001 | Riaziat et al. |
| 6,307,914 B1 | 10/2001 | Kunieda et al. |
| 6,316,776 B1 | 11/2001 | Hiramoto et al. |
| 6,366,021 B1 | 4/2002 | Meddaugh et al. |
| 6,369,585 B2 | 4/2002 | Yao |
| 6,380,545 B1 | 4/2002 | Yan |
| 6,417,634 B1 | 7/2002 | Bergstrom |
| 6,407,505 B1 | 8/2002 | Beitsche |
| 6,433,336 B1 | 8/2002 | Jongen et al. |
| 6,433,349 B2 | 8/2002 | Akiyama et al. |
| 6,433,494 B1 | 8/2002 | Kulish et al. |
| 6,441,569 B1 | 8/2002 | Janzow |
| 6,443,349 B1 | 9/2002 | Van Der Burg |
| 6,465,957 B1 | 10/2002 | Whitham et al. |
| 6,472,834 B2 | 10/2002 | Hiramoto et al. |
| 6,476,403 B1 | 11/2002 | Dolinskii et al. |
| 6,492,922 B1 | 12/2002 | New |
| 6,493,424 B2 | 12/2002 | Whitham |
| 6,498,444 B1 | 12/2002 | Hanna et al. |
| 6,501,961 B1 | 12/2002 | Scheikard et al. |
| 6,519,316 B1 | 2/2003 | Collins |
| 6,593,696 B2 | 7/2003 | Ding et al. |
| 6,594,336 B2 | 7/2003 | Nishizawa et al. |
| 6,600,164 B1 | 7/2003 | Badura et al. |
| 6,617,598 B1 | 9/2003 | Matsuda |
| 6,621,889 B1 | 9/2003 | Mostafavi |
| 6,622,244 B1 | 9/2003 | Eidson |
| 6,639,234 B1 | 10/2003 | Badura et al. |
| 6,646,383 B2 | 11/2003 | Bertsche et al. |
| 6,670,618 B1 | 12/2003 | Hartmann et al. |
| 6,683,162 B2 | 1/2004 | Scheinberg et al. |
| 6,683,318 B1 | 1/2004 | Haberer et al. |
| 6,683,426 B1 | 1/2004 | Kleeven |
| 6,693,283 B2 | 2/2004 | Eickhoff et al. |
| 6,710,362 B2 | 3/2004 | Kraft et al. |
| 6,713,773 B1 | 3/2004 | Lyons et al. |
| 6,713,976 B1 | 3/2004 | Zumoto et al. |
| 6,717,162 B1 | 4/2004 | Jongen |
| 6,736,831 B1 | 5/2004 | Hartmann et al. |
| 6,780,149 B1 | 6/2004 | Schulte |
| 6,745,072 B1 | 8/2004 | Badura et al. |
| 6,769,806 B2 | 8/2004 | Moyers |
| 6,774,383 B2 | 8/2004 | Norimine et al. |
| 6,777,669 B2 | 8/2004 | Nelson |
| 6,777,700 B2 | 8/2004 | Yanagisawa et al. |
| 6,799,068 B1 | 9/2004 | Hartmann et al. |
| 6,800,866 B2 | 10/2004 | Amemiya et al. |
| 6,803,591 B2 | 10/2004 | Muramatsu et al. |
| 6,814,694 B1 | 11/2004 | Padroni |
| 6,853,142 B2 | 2/2005 | Chistyakov |
| 6,853,703 B2 | 2/2005 | Svatos et al. |
| 6,864,770 B2 | 3/2005 | Nemoto et al. |
| 6,865,254 B2 | 3/2005 | Nafstadius |
| 6,873,123 B2 | 3/2005 | Marchand et al. |
| 6,891,177 B1 | 5/2005 | Kraft et al. |
| 6,891,924 B1 | 5/2005 | Yoda et al. |
| 6,894,300 B2 | 5/2005 | Reimoser et al. |
| 6,897,451 B2 | 5/2005 | Kaercher et al. |
| 6,914,396 B1 | 7/2005 | Symons et al. |
| 6,936,832 B2 | 8/2005 | Norimine et al. |
| 6,953,943 B2 | 10/2005 | Yanagisawa et al. |
| 6,965,116 B1 | 11/2005 | Wagner et al. |
| 6,969,194 B1 | 11/2005 | Nafstadius |
| 6,979,832 B2 | 12/2005 | Yanagisawa et al. |
| 6,984,835 B2 | 1/2006 | Harada |
| 6,992,312 B2 | 1/2006 | Yanagisawa et al. |
| 6,993,112 B2 | 1/2006 | Hesse |
| 7,008,105 B2 | 3/2006 | Amann et al. |
| 7,011,447 B2 | 3/2006 | Moyers |
| 7,012,267 B2 | 3/2006 | Moriyama et al. |
| 7,014,361 B1 | 3/2006 | Ein-Gal |
| 7,026,636 B2 | 4/2006 | Yanagisawa et al. |
| 7,038,403 B2 | 5/2006 | Mastrangeli et al. |
| 7,041,479 B2 | 5/2006 | Swartz et al. |
| 7,045,781 B2 | 5/2006 | Adamec et al. |
| 7,049,613 B2 | 5/2006 | Yanagisawa et al. |
| 7,053,389 B2 | 5/2006 | Yanagisawa et al. |
| 7,054,801 B2 | 5/2006 | Sakamoto et al. |
| 7,060,997 B2 | 6/2006 | Norimine et al. |
| 7,071,479 B2 | 7/2006 | Yanagisawa et al. |
| 7,073,508 B2 | 7/2006 | Moyers |
| 7,081,619 B2 | 7/2006 | Bashkirov et al. |
| 7,084,410 B2 | 8/2006 | Beloussov et al. |
| 7,091,478 B2 | 8/2006 | Haberer |
| 7,102,144 B2 | 9/2006 | Matsuda et al. |
| 7,122,811 B2 | 10/2006 | Matsuda et al. |
| 7,122,966 B2 | 10/2006 | Norling et al. |
| 7,122,978 B2 | 10/2006 | Nakanishi et al. |
| 7,135,678 B2 | 11/2006 | Wang et al. |
| 7,138,771 B2 | 11/2006 | Bechthold et al. |
| 7,154,107 B2 | 12/2006 | Yanagisawa et al. |
| 7,154,108 B2 | 12/2006 | Tadokoro et al. |
| 7,154,991 B2 | 12/2006 | Earnst et al. |
| 7,162,005 B2 | 1/2007 | Bjorkholm |
| 7,173,264 B2 | 2/2007 | Moriyama et al. |
| 7,173,265 B2 | 2/2007 | Miller et al. |
| 7,173,365 B2 | 2/2007 | Caporaso et al. |
| 7,186,991 B2 | 3/2007 | Kato et al. |
| 7,193,227 B2 | 3/2007 | Hiramoto et al. |
| 7,199,382 B2 | 4/2007 | Rigney et al. |
| 7,208,748 B2 | 4/2007 | Sliski et al. |
| 7,212,608 B2 | 5/2007 | Nagamine et al. |
| 7,212,609 B2 | 5/2007 | Nagamine et al. |
| 7,221,733 B1 | 5/2007 | Takai et al. |
| 7,227,161 B2 | 6/2007 | Matsuda et al. |
| 7,262,424 B2 | 6/2007 | Moriyama et al. |
| 7,247,869 B2 | 7/2007 | Tadokoro et al. |
| 7,257,191 B2 | 8/2007 | Sommer |
| 7,259,529 B2 | 8/2007 | Tanaka |
| 7,262,565 B2 | 8/2007 | Fujisawa |
| 7,266,356 B2 | 9/2007 | Ma et al. |
| 7,274,018 B2 | 9/2007 | Adamec et al. |
| 7,280,633 B2 | 10/2007 | Cheng et al. |
| 7,295,649 B2 | 11/2007 | Johnsen |
| 7,297,967 B2 | 11/2007 | Yanagisawa et al. |
| 7,301,162 B2 | 11/2007 | Matsuda et al. |

(56) References Cited

U.S. PATENT DOCUMENTS

| | | | |
|---|---|---|---|
| 7,307,264 | B2 | 12/2007 | Brusasco et al. |
| 7,318,605 | B2 | 1/2008 | Schweikard et al. |
| 7,319,231 | B2 | 1/2008 | Moriyama et al. |
| 7,319,336 | B2 | 1/2008 | Baur et al. |
| 7,331,713 | B2 | 2/2008 | Moyers |
| 7,332,880 | B2 | 2/2008 | Ina et al. |
| 7,345,291 | B2 | 3/2008 | Kats |
| 7,345,292 | B2 | 3/2008 | Moriyama et al. |
| 7,348,557 | B2 | 3/2008 | Armit |
| 7,348,579 | B2 | 3/2008 | Pedroni |
| 7,351,988 | B2 | 4/2008 | Naumann et al. |
| 7,355,189 | B2 | 4/2008 | Yanagisawa et al. |
| 7,366,740 | B2 | 4/2008 | Beloussov et al. |
| 7,372,053 | B2 | 5/2008 | Yamashita et al. |
| 7,376,672 | B2 | 5/2008 | Harada |
| 7,381,979 | B2 | 6/2008 | Yamashita et al. |
| 7,396,309 | B2 | 7/2008 | Baumann et al. |
| 7,397,054 | B2 | 7/2008 | Natori et al. |
| 7,397,901 | B1 | 7/2008 | Johnsen |
| 7,402,822 | B2 | 7/2008 | Guertin et al. |
| 7,402,823 | B2 | 7/2008 | Guertin et al. |
| 7,402,824 | B2 | 7/2008 | Guertin et al. |
| 7,402,963 | B2 | 7/2008 | Sliski et al. |
| 7,405,407 | B2 | 7/2008 | Hiramoto et al. |
| 7,425,717 | B2 | 9/2008 | Matsuda et al. |
| 7,432,516 | B2 | 10/2008 | Peggs et al. |
| 7,439,528 | B2 | 10/2008 | Nishiuchi et al. |
| 7,446,328 | B2 | 11/2008 | Rigney et al. |
| 7,446,490 | B2 | 11/2008 | Jongen et al. |
| 7,449,701 | B2 | 11/2008 | Fujimaki et al. |
| 7,453,076 | B2 | 11/2008 | Welch et al. |
| 7,465,944 | B2 | 12/2008 | Ueno et al. |
| 7,466,085 | B2 | 12/2008 | Nutt |
| 7,468,506 | B2 | 12/2008 | Rogers et al. |
| 7,469,035 | B2 | 12/2008 | Keall et al. |
| 7,473,913 | B2 | 1/2009 | Hermann et al. |
| 7,476,667 | B2 | 1/2009 | Fritsch et al. |
| 7,476,883 | B2 | 1/2009 | Nutt |
| 7,482,606 | B2 | 1/2009 | Groezinger et al. |
| 7,492,556 | B2 | 2/2009 | Atkins et al. |
| 7,507,975 | B2 | 3/2009 | Mohr |
| 7,525,104 | B2 | 4/2009 | Harada |
| 7,541,905 | B2 | 6/2009 | Antaya |
| 7,547,901 | B2 | 6/2009 | Guertin et al. |
| 7,554,096 | B2 | 6/2009 | Ward et al. |
| 7,554,097 | B2 | 6/2009 | Ward et al. |
| 7,554,275 | B2 | 6/2009 | Amaldi |
| 7,555,103 | B2 | 6/2009 | Johnsen |
| 7,557,358 | B2 | 7/2009 | Ward et al. |
| 7,557,359 | B2 | 7/2009 | Ward et al. |
| 7,557,360 | B2 | 7/2009 | Ward et al. |
| 7,557,361 | B2 | 7/2009 | Ward et al. |
| 7,560,698 | B2 | 7/2009 | Rietzel |
| 7,560,712 | B2 | 7/2009 | Kim et al. |
| 7,560,715 | B2 | 7/2009 | Pedroni |
| 7,560,717 | B2 | 7/2009 | Matsuda et al. |
| 7,567,694 | B2 | 7/2009 | Lu et al. |
| 7,574,251 | B2 | 8/2009 | Lu et al. |
| 7,576,499 | B2 | 8/2009 | Caporaso et al. |
| 7,579,603 | B2 | 8/2009 | Birgy et al. |
| 7,579,610 | B2 | 8/2009 | Grozinger et al. |
| 7,582,666 | B2 | 9/2009 | Furuhashi et al. |
| 7,582,885 | B2 | 9/2009 | Katagiri et al. |
| 7,586,112 | B2 | 9/2009 | Chiba et al. |
| 7,596,497 | B2 | 10/2009 | Yamamoto et al. |
| 7,609,009 | B2 | 10/2009 | Tanaka et al. |
| 7,609,809 | B2 | 10/2009 | Kapatoes et al. |
| 7,609,811 | B1 | 10/2009 | Siljamaki et al. |
| 7,615,942 | B2 | 11/2009 | Sanders et al. |
| 7,628,347 | B2 | 12/2009 | Sliski et al. |
| 7,629,598 | B2 | 12/2009 | Harada |
| 7,639,853 | B2 | 12/2009 | Olivera et al. |
| 7,639,854 | B2 | 12/2009 | Schnarr et al. |
| 7,643,661 | B2 | 1/2010 | Ruchala et al. |
| 7,656,258 | B1 | 2/2010 | Antaya et al. |
| 7,659,521 | B2 | 2/2010 | Pedroni |
| 7,659,528 | B2 | 2/2010 | Uematsu |
| 7,668,291 | B2 | 2/2010 | Nord et al. |
| 7,672,429 | B2 | 3/2010 | Urano et al. |
| 7,679,049 | B2 | 3/2010 | Rietzel |
| 7,679,073 | B2 | 3/2010 | Urano et al. |
| 7,682,078 | B2 | 3/2010 | Rietzel |
| 7,692,166 | B2 | 4/2010 | Muraki et al. |
| 7,692,168 | B2 | 4/2010 | Moriyama et al. |
| 7,696,499 | B2 | 4/2010 | Miller et al. |
| 7,696,847 | B2 | 4/2010 | Antaya |
| 7,701,677 | B2 | 4/2010 | Schultz et al. |
| 7,709,818 | B2 | 5/2010 | Matsuda et al. |
| 7,710,051 | B2 | 5/2010 | Caporaso et al. |
| 7,718,982 | B2 | 5/2010 | Sliski et al. |
| 7,728,311 | B2 | 6/2010 | Gall |
| 7,746,978 | B2 | 6/2010 | Cheng et al. |
| 7,755,068 | B2 | 7/2010 | Ma et al. |
| 7,755,305 | B2 | 7/2010 | Umezawa et al. |
| 7,759,642 | B2 | 7/2010 | Nir |
| 7,763,867 | B2 | 7/2010 | Birgy et al. |
| 7,767,988 | B2 | 8/2010 | Kaiser et al. |
| 7,770,231 | B2 | 8/2010 | Prater et al. |
| 7,772,577 | B2 | 8/2010 | Saito et al. |
| 7,773,723 | B2 | 8/2010 | Nord et al. |
| 7,773,788 | B2 | 8/2010 | Lu et al. |
| 7,778,488 | B2 | 8/2010 | Nord et al. |
| 7,783,010 | B2 | 8/2010 | Clayton |
| 7,784,124 | B2 | 8/2010 | Long et al. |
| 7,784,127 | B2 | 8/2010 | Kuro et al. |
| 7,786,433 | B2 | 8/2010 | Gunzert-Marx et al. |
| 7,786,451 | B2 | 8/2010 | Ward et al. |
| 7,786,452 | B2 | 8/2010 | Ward et al. |
| 7,789,560 | B2 | 9/2010 | Moyers |
| 7,791,051 | B2 | 9/2010 | Beloussov et al. |
| 7,796,731 | B2 | 9/2010 | Nord et al. |
| 7,801,269 | B2 | 9/2010 | Cravens et al. |
| 7,801,270 | B2 | 9/2010 | Nord et al. |
| 7,801,988 | B2 | 9/2010 | Baumann et al. |
| 7,807,982 | B2 | 10/2010 | Nishiuchi et al. |
| 7,809,107 | B2 | 10/2010 | Nord et al. |
| 7,812,319 | B2 | 10/2010 | Diehl et al. |
| 7,812,326 | B2 | 10/2010 | Grozinger et al. |
| 7,816,657 | B2 | 10/2010 | Hansmann et al. |
| 7,817,778 | B2 | 10/2010 | Nord et al. |
| 7,817,836 | B2 | 10/2010 | Chao et al. |
| 7,818,045 | B2 | 10/2010 | Rietzel |
| 7,834,334 | B2 | 11/2010 | Grozinger et al. |
| 7,834,336 | B2 | 11/2010 | Boeh et al. |
| 7,835,494 | B2 | 11/2010 | Nord et al. |
| 7,835,502 | B2 | 11/2010 | Spence et al. |
| 7,839,972 | B2 | 11/2010 | Ruchala et al. |
| 7,839,973 | B2 | 11/2010 | Nord et al. |
| 7,842,606 | B2 | 11/2010 | Lee et al. |
| 7,848,488 | B2 | 12/2010 | Mansfield |
| 7,857,756 | B2 | 12/2010 | Warren et al. |
| 7,860,216 | B2 | 12/2010 | Jongen et al. |
| 7,860,550 | B2 | 12/2010 | Saracen et al. |
| 7,868,301 | B2 | 1/2011 | Diehl |
| 7,875,846 | B2 | 1/2011 | Gunzert-Marx et al. |
| 7,875,861 | B2 | 1/2011 | Huttenberger et al. |
| 7,875,868 | B2 | 1/2011 | Moriyama et al. |
| 7,881,431 | B2 | 2/2011 | Aoi et al. |
| 7,894,574 | B1 | 2/2011 | Nord et al. |
| 7,903,781 | B2 | 3/2011 | Foland et al. |
| 7,906,769 | B2 | 3/2011 | Blasche et al. |
| 7,914,734 | B2 | 3/2011 | Livingston |
| 7,919,765 | B2 | 4/2011 | Timmer |
| 7,920,040 | B2 | 4/2011 | Antaya et al. |
| 7,920,675 | B2 | 4/2011 | Lomax et al. |
| 7,928,415 | B2 | 4/2011 | Bert et al. |
| 7,934,869 | B2 | 5/2011 | Ivanov et al. |
| 7,940,881 | B2 | 5/2011 | Jongen et al. |
| 7,943,913 | B2 | 5/2011 | Balakin |
| 7,947,969 | B2 | 5/2011 | Pu |
| 7,949,096 | B2 | 5/2011 | Cheng et al. |
| 7,950,587 | B2 | 5/2011 | Henson et al. |
| 7,953,205 | B2 | 5/2011 | Balakin |
| 7,960,710 | B2 | 6/2011 | Kruip et al. |

(56) References Cited

U.S. PATENT DOCUMENTS

| | | |
|---|---|---|
| 7,961,844 B2 | 6/2011 | Takeda et al. |
| 7,977,648 B2 | 7/2011 | Westerly et al. |
| 7,977,656 B2 | 7/2011 | Fujimaki et al. |
| 7,982,198 B2 | 7/2011 | Nishiuchi et al. |
| 7,982,416 B2 | 7/2011 | Tanaka et al. |
| 7,984,715 B2 | 7/2011 | Moyers |
| 7,986,768 B2 | 7/2011 | Nord et al. |
| 7,987,053 B2 | 7/2011 | Schaffner |
| 7,989,785 B2 | 8/2011 | Emhofer et al. |
| 7,990,524 B2 | 8/2011 | Jureller et al. |
| 7,997,553 B2 | 8/2011 | Sloan et al. |
| 8,002,466 B2 | 8/2011 | Von Neubeck et al. |
| 8,003,964 B2 | 8/2011 | Stark et al. |
| 8,009,603 B2 | 8/2011 | Nord et al. |
| 8,009,804 B2 | 8/2011 | Siljamaki et al. |
| 8,016,336 B2 | 9/2011 | Messinger et al. |
| 8,039,822 B2 | 10/2011 | Rietzel |
| 8,041,006 B2 | 10/2011 | Boyden et al. |
| 8,044,364 B2 | 10/2011 | Yamamoto |
| 8,049,187 B2 | 11/2011 | Tachikawa |
| 8,053,508 B2 | 11/2011 | Korkut et al. |
| 8,053,739 B2 | 11/2011 | Rietzel |
| 8,053,745 B2 | 11/2011 | Moore |
| 8,053,746 B2 | 11/2011 | Timmar et al. |
| 8,063,381 B2 | 11/2011 | Tsoupas et al. |
| 8,067,748 B2 | 11/2011 | Balakin |
| 8,069,675 B2 | 12/2011 | Radovinsky et al. |
| 8,071,966 B2 | 12/2011 | Kaiser et al. |
| 8,080,801 B2 | 12/2011 | Safai |
| 8,085,899 B2 | 12/2011 | Nord et al. |
| 8,089,054 B2 | 1/2012 | Balakin |
| 8,093,564 B2 | 1/2012 | Balakin |
| 8,093,568 B2 | 1/2012 | Mackie et al. |
| 8,111,125 B2 | 2/2012 | Antaya et al. |
| 8,129,694 B2 | 3/2012 | Balakin |
| 8,129,699 B2 | 3/2012 | Balakin |
| 8,144,832 B2 | 3/2012 | Balakin |
| 8,153,989 B2 | 4/2012 | Tachikawa et al. |
| 8,173,981 B2 | 5/2012 | Trbojevic |
| 8,173,983 B1 | 5/2012 | Sahadevan |
| 8,183,541 B2 | 5/2012 | Wilkens et al. |
| 8,188,688 B2 | 5/2012 | Balakin |
| 8,189,889 B2 | 5/2012 | Pearlstein et al. |
| 8,198,607 B2 | 6/2012 | Balakin |
| 8,222,613 B2 | 7/2012 | Tajiri et al. |
| 8,227,768 B2 | 7/2012 | Smick et al. |
| 8,232,536 B2 | 7/2012 | Harada |
| 8,207,856 B2 | 8/2012 | Baumgartner et al. |
| 8,253,121 B2 | 8/2012 | Gnutzmann et al. |
| 8,263,645 B2 | 10/2012 | Guneysel |
| 8,288,742 B2 | 10/2012 | Balakin |
| 8,291,717 B2 | 10/2012 | Radovinsky et al. |
| 8,294,127 B2 | 10/2012 | Tachibana |
| 8,304,725 B2 | 11/2012 | Komuro et al. |
| 8,304,750 B2 | 11/2012 | Preikszas et al. |
| 8,309,941 B2 | 11/2012 | Balakin |
| 8,330,132 B2 | 12/2012 | Guertin et al. |
| 8,334,520 B2 | 12/2012 | Otaka et al. |
| 8,335,397 B2 | 12/2012 | Takane et al. |
| 8,344,340 B2 | 1/2013 | Gall et al. |
| 8,350,214 B2 | 1/2013 | Otaki et al. |
| 8,354,656 B2 | 1/2013 | Beloussov et al. |
| 8,368,038 B2 | 2/2013 | Balakin |
| 8,368,043 B2 | 2/2013 | Havelange et al. |
| 8,373,143 B2 | 2/2013 | Balakin |
| 8,373,145 B2 | 2/2013 | Balakin |
| 8,373,146 B2 | 2/2013 | Balakin |
| 8,374,314 B2 | 2/2013 | Balakin |
| 8,378,299 B2 | 2/2013 | Frosien |
| 8,378,311 B2 | 2/2013 | Balakin |
| 8,378,312 B1 | 2/2013 | Gordon et al. |
| 8,378,321 B2 | 2/2013 | Balakin |
| 8,382,943 B2 | 2/2013 | Clark |
| 8,389,949 B2 | 3/2013 | Harada et al. |
| 8,399,866 B2 | 3/2013 | Balakin |
| 8,405,042 B2 | 3/2013 | Honda et al. |
| 8,405,056 B2 | 3/2013 | Amaldi et al. |
| 8,415,643 B2 | 4/2013 | Balakin |
| 8,416,918 B2 | 4/2013 | Nord et al. |
| 8,421,041 B2 | 4/2013 | Balakin |
| 8,426,833 B2 | 4/2013 | Trbojevic |
| 8,436,323 B2 | 5/2013 | Iseki et al. |
| 8,436,325 B2 | 5/2013 | Noda et al. |
| 8,436,327 B2 | 5/2013 | Balakin |
| 8,440,987 B2 | 5/2013 | Stephani et al. |
| 8,445,872 B2 | 5/2013 | Behrens et al. |
| 8,459,714 B2 | 6/2013 | Pomper et al. |
| 8,461,559 B2 | 6/2013 | Lomax |
| 8,462,912 B2 | 6/2013 | O'Connor et al. |
| 8,466,441 B2 | 6/2013 | Iwata et al. |
| 8,472,583 B2 | 6/2013 | Star-Lack et al. |
| 8,481,951 B2 | 7/2013 | Jongen et al. |
| 8,483,357 B2 | 7/2013 | Siljamaki et al. |
| 8,487,278 B2 | 7/2013 | Balakin |
| 8,519,365 B2 | 8/2013 | Balakin |
| 8,525,419 B2 | 9/2013 | Smith et al. |
| 8,525,447 B2 | 9/2013 | Antaya |
| 8,525,448 B2 | 9/2013 | Tanaka et al. |
| 8,546,769 B2 | 10/2013 | Uno |
| 8,552,406 B2 | 10/2013 | Phaneuf et al. |
| 8,552,408 B2 | 10/2013 | Hanawa et al. |
| 8,558,461 B2 | 10/2013 | Poehlmann-Martins et al. |
| 8,558,485 B2 | 10/2013 | Antaya |
| 8,569,717 B2 | 10/2013 | Balakin |
| 8,575,563 B2 | 11/2013 | Cameron et al. |
| 8,575,579 B2 | 11/2013 | Moskvin et al. |
| 8,581,215 B2 | 11/2013 | Balakin |
| 8,581,218 B2 | 11/2013 | Fujimoto et al. |
| 8,581,523 B2 | 11/2013 | Gall et al. |
| 8,581,525 B2 | 11/2013 | Antaya et al. |
| 8,598,543 B2 | 12/2013 | Balakin |
| 8,601,116 B2 | 12/2013 | Baumann et al. |
| 8,613,694 B2 | 12/2013 | Walsh |
| 8,614,554 B2 | 12/2013 | Balakin |
| 8,614,612 B2 | 12/2013 | Antaya et al. |
| 8,618,519 B2 | 12/2013 | Ueda |
| 8,619,242 B2 | 12/2013 | Suzuki |
| 8,624,528 B2 | 1/2014 | Balakin |
| 8,627,822 B2 | 1/2014 | Balakin |
| 8,632,448 B1 | 1/2014 | Schulte et al. |
| 8,637,818 B2 | 1/2014 | Balakin |
| 8,637,839 B2 | 1/2014 | Brauer |
| 8,642,978 B2 | 2/2014 | Balakin |
| 8,643,314 B2 | 2/2014 | Touchi |
| 8,644,571 B1 | 2/2014 | Schulte et al. |
| 8,653,314 B2 | 2/2014 | Pelati et al. |
| 8,657,354 B2 | 2/2014 | Pomper et al. |
| 8,657,743 B2 | 2/2014 | Rietzel et al. |
| 8,688,197 B2 | 4/2014 | Balakin |
| 8,702,578 B2 | 4/2014 | Fahrig et al. |
| 8,704,197 B2 | 4/2014 | Gemmel |
| 8,710,462 B2 | 4/2014 | Balakin |
| 8,716,663 B2 | 5/2014 | Brusasco et al. |
| 8,718,231 B2 | 5/2014 | Balakin |
| 8,748,852 B2 | 6/2014 | Jongen |
| 8,750,453 B2 | 6/2014 | Cheng et al. |
| 8,766,217 B2 | 7/2014 | Balakin |
| 8,766,218 B2 | 7/2014 | Jongen |
| 8,791,435 B2 | 7/2014 | Balakin |
| 8,791,656 B1 | 7/2014 | Zwart et al. |
| 8,796,648 B2 | 8/2014 | Fujimoto et al. |
| 8,835,885 B2 | 9/2014 | Ogasawara |
| 8,847,179 B2 | 9/2014 | Fujitaka et al. |
| 8,859,264 B2 | 10/2014 | Bert et al. |
| 8,866,109 B2 | 10/2014 | Sasai |
| 8,896,239 B2 | 11/2014 | Balakin |
| 8,897,857 B2 | 11/2014 | Tome et al. |
| 8,901,509 B2 | 12/2014 | Balakin |
| 8,901,520 B2 | 12/2014 | Tachibana et al. |
| 8,907,309 B2 | 12/2014 | Spotts |
| 8,907,311 B2 | 12/2014 | Gall et al. |
| 8,907,594 B2 | 12/2014 | Begg et al. |
| 8,915,833 B1 | 12/2014 | Sahadevan |
| 8,916,838 B2 | 12/2014 | Claereboudt et al. |

(56) References Cited

U.S. PATENT DOCUMENTS

| | | |
|---|---|---|
| 8,916,841 B2 | 12/2014 | Totake et al. |
| 8,916,843 B2 | 12/2014 | Gall et al. |
| 8,927,946 B2 | 1/2015 | Behrens et al. |
| 8,927,950 B2 | 1/2015 | Gall et al. |
| 8,933,650 B2 | 1/2015 | O'Neal, III et al. |
| 8,941,084 B2 | 1/2015 | Balakin |
| 8,941,086 B2 | 1/2015 | Yajima |
| 8,947,021 B2 | 2/2015 | Tsutsui |
| 8,948,341 B2 | 2/2015 | Beckman |
| 8,952,343 B2 | 2/2015 | Stephani et al. |
| 8,952,634 B2 | 2/2015 | Sliski et al. |
| 8,957,396 B2 | 2/2015 | Balakin |
| 8,963,112 B1 | 2/2015 | Balakin |
| 8,969,834 B2 | 3/2015 | Balakin |
| 8,970,137 B2 | 3/2015 | Gall et al. |
| 8,971,363 B2 | 3/2015 | Levecq et al. |
| 8,975,600 B2 | 3/2015 | Balakin |
| 8,975,602 B2 | 3/2015 | Huber et al. |
| 8,975,836 B2 | 3/2015 | Bromberg et al. |
| 8,986,186 B2 | 3/2015 | Zhang et al. |
| 8,993,522 B2 | 3/2015 | Vidyasagar et al. |
| 9,006,693 B2 | 4/2015 | Sasai |
| 9,007,740 B2 | 4/2015 | Touchi |
| 9,012,832 B2 | 4/2015 | Bert et al. |
| 9,012,866 B2 | 4/2015 | Benna et al. |
| 9,012,873 B2 | 4/2015 | Fujimoto et al. |
| 9,018,601 B2 | 4/2015 | Balakin |
| 9,024,256 B2 | 5/2015 | Ruan et al. |
| 9,029,760 B2 | 5/2015 | Beddar et al. |
| 9,044,600 B2 | 6/2015 | Balakin |
| 9,056,199 B2 | 6/2015 | Balakin |
| 9,058,910 B2 | 6/2015 | Balakin |
| 9,060,998 B2 | 6/2015 | Stockfleth |
| 9,061,143 B2 | 6/2015 | Sasai et al. |
| 9,084,887 B2 | 7/2015 | Schulte et al. |
| 9,093,209 B2 | 7/2015 | Jongen |
| 9,095,040 B2 | 7/2015 | Balakin |
| 9,108,050 B2 | 8/2015 | Bula et al. |
| 9,142,385 B1 | 9/2015 | Iwanaga |
| 9,155,186 B2 | 10/2015 | Zwart et al. |
| 9,155,908 B2 | 10/2015 | Meltsner et al. |
| 9,155,910 B1 | 10/2015 | Sahadevan |
| 9,185,789 B2 | 11/2015 | Zwart et al. |
| 9,186,525 B2 | 11/2015 | Prieels et al. |
| 9,188,685 B2 | 11/2015 | Takayanagi et al. |
| 9,196,082 B2 | 11/2015 | Pearlstein et al. |
| 9,220,920 B2 | 12/2015 | Schulte et al. |
| 9,220,923 B2 | 12/2015 | Yajima et al. |
| 9,237,640 B2 | 1/2016 | Abs et al. |
| 9,237,642 B2 | 1/2016 | Kleeven |
| 9,245,336 B2 | 1/2016 | Mallya et al. |
| 9,254,396 B2 | 2/2016 | Mihaylov |
| 9,259,155 B2 | 2/2016 | Bharat et al. |
| 9,271,385 B2 | 2/2016 | Verbruggen et al. |
| 9,283,406 B2 | 3/2016 | Prieels |
| 9,283,407 B2 | 3/2016 | Benna et al. |
| 9,289,140 B2 | 3/2016 | Ross et al. |
| 9,289,624 B2 | 3/2016 | Jongen |
| 9,297,912 B2 | 3/2016 | Campbell et al. |
| 9,301,384 B2 | 3/2016 | Zwart et al. |
| 9,302,121 B2 | 4/2016 | Totake et al. |
| 9,305,742 B2 | 4/2016 | Aptaker et al. |
| 9,308,394 B2 | 4/2016 | Nishiuchi et al. |
| 9,355,784 B2 | 5/2016 | Abs |
| 9,364,688 B2 | 6/2016 | Pausch et al. |
| 9,370,089 B2 | 6/2016 | Ungaro et al. |
| 9,381,379 B2 | 7/2016 | Beckman |
| 9,393,443 B2 | 7/2016 | Fujimoto et al. |
| 9,417,302 B2 | 8/2016 | Kuhn |
| 9,451,688 B2 | 9/2016 | Jongen |
| 9,451,689 B2 | 9/2016 | Tsutsui |
| 9,452,300 B2 | 9/2016 | Anferov |
| 9,452,301 B2 | 9/2016 | Gall et al. |
| 9,468,608 B2 | 10/2016 | Lin et al. |
| 9,492,684 B2 | 11/2016 | Takayanagi et al. |
| 9,661,736 B2 | 5/2017 | O'Neal, III et al. |
| 9,855,445 B2 | 1/2018 | Mansfield |
| 9,999,787 B1 | 6/2018 | Ruohonen et al. |
| 10,092,774 B1 | 10/2018 | Vanderstraten et al. |
| 10,183,179 B1 | 1/2019 | Smith et al. |
| 10,245,448 B2 | 4/2019 | Heese |
| 10,307,618 B2 | 6/2019 | Mansfield |
| 10,549,117 B2 | 2/2020 | Vanderstraten et al. |
| 10,609,806 B2 | 3/2020 | Roecken et al. |
| 10,675,487 B2 | 6/2020 | Zwart et al. |
| 10,702,716 B2 | 7/2020 | Heese |
| 10,786,689 B2 | 9/2020 | Zwart et al. |
| 10,814,144 B2 | 10/2020 | Khuntia et al. |
| 10,843,011 B2 | 11/2020 | Trail et al. |
| 10,850,124 B2 | 12/2020 | Vanderstraten et al. |
| 10,898,730 B2 | 1/2021 | Smith et al. |
| 10,910,188 B2 | 2/2021 | Star-Lack et al. |
| 10,918,886 B2 | 2/2021 | Smith et al. |
| 11,103,727 B2 | 8/2021 | Folkerts et al. |
| 11,116,995 B2 | 9/2021 | Khuntia et al. |
| 11,291,861 B2 | 4/2022 | Cooley |
| 11,717,703 B2 | 8/2023 | Cooley |
| 2002/0058007 A1 | 5/2002 | Scheinberg et al. |
| 2002/0172317 A1 | 11/2002 | Maksimchuk et al. |
| 2003/0048080 A1 | 3/2003 | Amemiya et al. |
| 2003/0125622 A1 | 7/2003 | Schweikard et al. |
| 2003/0136924 A1 | 7/2003 | Kraft et al. |
| 2003/0152197 A1 | 8/2003 | Moyers |
| 2003/0163015 A1 | 8/2003 | Yanagisawa et al. |
| 2003/0183779 A1 | 10/2003 | Norimine et al. |
| 2003/0234369 A1 | 12/2003 | Glukhoy |
| 2004/0000650 A1 | 1/2004 | Yanagisawa et al. |
| 2004/0017888 A1 | 1/2004 | Seppi et al. |
| 2004/0058212 A1 | 3/2004 | Yanagisawa et al. |
| 2004/0061077 A1 | 4/2004 | Muramatsu et al. |
| 2004/0061078 A1 | 4/2004 | Muramatsu et al. |
| 2004/0085023 A1 | 5/2004 | Chistyakov |
| 2004/0098445 A1 | 5/2004 | Baumann et al. |
| 2004/0111134 A1 | 6/2004 | Muramatsu et al. |
| 2004/0118081 A1 | 6/2004 | Reimoser et al. |
| 2004/0149934 A1 | 8/2004 | Yanagisawa et al. |
| 2004/0155206 A1 | 8/2004 | Marchand et al. |
| 2004/0159795 A1 | 8/2004 | Kaercher et al. |
| 2004/0164254 A1 | 8/2004 | Beloussov et al. |
| 2004/0173763 A1 | 9/2004 | Moriyama et al. |
| 2004/0174958 A1 | 9/2004 | Moriyama et al. |
| 2004/0183033 A1 | 9/2004 | Moriyama et al. |
| 2004/0183035 A1 | 9/2004 | Yanagisawa et al. |
| 2004/0200982 A1 | 10/2004 | Moriyama et al. |
| 2004/0200983 A1 | 10/2004 | Fujimaki et al. |
| 2004/0213381 A1 | 10/2004 | Harada |
| 2004/0227104 A1 | 11/2004 | Matsuda et al. |
| 2004/0232356 A1 | 11/2004 | Norimine et al. |
| 2004/0240626 A1 | 12/2004 | Moyers |
| 2005/0029472 A1 | 2/2005 | Ueno et al. |
| 2005/0051740 A1 | 3/2005 | Yanagisawa et al. |
| 2005/0058245 A1 | 3/2005 | Ein-Gal |
| 2005/0072940 A1 | 4/2005 | Beloussov et al. |
| 2005/0079235 A1 | 4/2005 | Stockfleth |
| 2005/0087700 A1 | 4/2005 | Tadokoro et al. |
| 2005/0089141 A1 | 4/2005 | Brown |
| 2005/0099145 A1 | 5/2005 | Nishiuchi et al. |
| 2005/0113327 A1 | 5/2005 | Roiz et al. |
| 2005/0127306 A1 | 6/2005 | Yanagisawa et al. |
| 2005/0161618 A1 | 7/2005 | Pedroni |
| 2005/0139787 A1 | 8/2005 | Chiba et al. |
| 2005/0167616 A1 | 8/2005 | Yanagisawa |
| 2005/0184686 A1 | 8/2005 | Caporaso et al. |
| 2005/0186179 A1 | 8/2005 | Harats et al. |
| 2005/0205806 A1 | 9/2005 | Tadokoro et al. |
| 2005/0228255 A1 | 10/2005 | Saracan et al. |
| 2005/0234327 A1 | 10/2005 | Saracan et al. |
| 2005/0247890 A1 | 11/2005 | Norimine et al. |
| 2005/0259779 A1 | 11/2005 | Abraham-Fuchs et al. |
| 2006/0017015 A1 | 1/2006 | Sliski et al. |
| 2006/0067468 A1 | 3/2006 | Rietzel |
| 2006/0126792 A1 | 6/2006 | Li |
| 2006/0145088 A1 | 7/2006 | Ma |
| 2006/0127878 A1 | 8/2006 | Fuccione |

(56) References Cited

U.S. PATENT DOCUMENTS

| | | |
|---|---|---|
| 2006/0175991 A1 | 8/2006 | Fujisawa |
| 2006/0192148 A1 | 8/2006 | Yanagisawa et al. |
| 2006/0203967 A1 | 9/2006 | Nilsson |
| 2006/0204478 A1 | 9/2006 | Harats et al. |
| 2006/0219948 A1 | 10/2006 | Ueno et al. |
| 2006/0284562 A1 | 12/2006 | Hruby et al. |
| 2007/0001128 A1 | 1/2007 | Sliski et al. |
| 2007/0013273 A1 | 1/2007 | Albert et al. |
| 2007/0014654 A1 | 1/2007 | Haverfield et al. |
| 2007/0018120 A1 | 1/2007 | Beloussov et al. |
| 2007/0023699 A1 | 2/2007 | Yamashita et al. |
| 2007/0029510 A1 | 2/2007 | Hermann et al. |
| 2007/0031337 A1 | 2/2007 | Schulte |
| 2007/0034812 A1 | 2/2007 | Ma et al. |
| 2007/0051904 A1 | 3/2007 | Kaiser et al. |
| 2007/0053484 A1 | 3/2007 | Chiba et al. |
| 2007/0059387 A1 | 3/2007 | Stockfleth |
| 2007/0075273 A1 | 4/2007 | Birgy et al. |
| 2007/0083101 A1 | 4/2007 | Rietzel |
| 2007/0092812 A1 | 4/2007 | Caporaso et al. |
| 2007/0108922 A1 | 5/2007 | Amaldi |
| 2007/0114464 A1 | 5/2007 | Birgy et al. |
| 2007/0114471 A1 | 5/2007 | Birgy et al. |
| 2007/0114945 A1 | 5/2007 | Mattaboni et al. |
| 2007/0145916 A1 | 6/2007 | Caporaso et al. |
| 2007/0171015 A1 | 7/2007 | Antaya |
| 2007/0181519 A1 | 8/2007 | Khoshnevis |
| 2007/0217575 A1 | 9/2007 | Kaiser et al. |
| 2007/0228304 A1 | 10/2007 | Nishiuchi |
| 2007/0262269 A1 | 11/2007 | Trbojevic |
| 2007/0284548 A1 | 12/2007 | Kaiser et al. |
| 2008/0023644 A1 | 1/2008 | Pedroni |
| 2008/0029706 A1 | 2/2008 | Kaiser et al. |
| 2008/0031414 A1 | 2/2008 | Coppens |
| 2008/0061241 A1 | 3/2008 | Rietzel |
| 2008/0078942 A1 | 4/2008 | Rietzel |
| 2008/0093567 A1 | 4/2008 | Gall |
| 2008/0131419 A1 | 6/2008 | Roiz et al. |
| 2008/0179544 A1 | 7/2008 | Kaiser et al. |
| 2008/0191142 A1 | 8/2008 | Pedroni |
| 2008/0191152 A1 | 8/2008 | Grozinger et al. |
| 2008/0218102 A1 | 9/2008 | Sliski et al. |
| 2008/0219407 A1 | 9/2008 | Kaiser et al. |
| 2008/0219410 A1 | 9/2008 | Gunzert-Marx et al. |
| 2008/0219411 A1 | 9/2008 | Gunzert-Marx et al. |
| 2008/0237494 A1 | 10/2008 | Beloussov et al. |
| 2008/0237495 A1 | 10/2008 | Grozinger et al. |
| 2008/0267349 A1 | 10/2008 | Rietzel |
| 2008/0270517 A1 | 10/2008 | Baumann et al. |
| 2008/0272284 A1 | 11/2008 | Rietzel |
| 2008/0290299 A1 | 11/2008 | Hansmann et al. |
| 2008/0301872 A1 | 12/2008 | Fahrig et al. |
| 2008/0315111 A1 | 12/2008 | Sommer |
| 2009/0008575 A1* | 1/2009 | Okazaki .......... A61N 5/10 250/492.1 |
| 2009/0032742 A1 | 2/2009 | Kaiser et al. |
| 2009/0050819 A1 | 2/2009 | Ma et al. |
| 2009/0060130 A1 | 3/2009 | Wilkens et al. |
| 2009/0065717 A1 | 3/2009 | Kaiser et al. |
| 2009/0069640 A1 | 3/2009 | Rietzel et al. |
| 2009/0077209 A1 | 3/2009 | Schneider |
| 2009/0096179 A1 | 4/2009 | Stark et al. |
| 2009/0098145 A1 | 4/2009 | Mata et al. |
| 2009/0101833 A1 | 4/2009 | Emhofer et al. |
| 2009/0114847 A1 | 5/2009 | Grozinger et al. |
| 2009/0140671 A1 | 6/2009 | O'Neal, III et al. |
| 2009/0140672 A1 | 6/2009 | Gall et al. |
| 2009/0175414 A1 | 7/2009 | Messinger et al. |
| 2009/0200483 A1 | 8/2009 | Gall et al. |
| 2009/0230327 A1 | 9/2009 | Rietzel |
| 2009/0234237 A1 | 9/2009 | Ross et al. |
| 2009/0236545 A1 | 9/2009 | Timmer |
| 2009/0242789 A1 | 10/2009 | Tachikawa |
| 2009/0261275 A1 | 10/2009 | Rietzel |
| 2009/0274269 A1 | 11/2009 | Foland et al. |
| 2009/0296885 A1 | 12/2009 | Boeh et al. |
| 2009/0309046 A1 | 12/2009 | Balakin |
| 2009/0309047 A1 | 12/2009 | Gunzert-Marx et al. |
| 2009/0309520 A1 | 12/2009 | Balakin |
| 2009/0314960 A1 | 12/2009 | Balakin |
| 2009/0314961 A1 | 12/2009 | Balakin |
| 2009/0321656 A1 | 12/2009 | Rietzel et al. |
| 2009/0321665 A1 | 12/2009 | Timmer et al. |
| 2010/0006106 A1 | 1/2010 | Balakin |
| 2010/0006770 A1 | 1/2010 | Balakin |
| 2010/0008466 A1 | 1/2010 | Balakin |
| 2010/0014638 A1 | 1/2010 | Balakin |
| 2010/0014640 A1 | 1/2010 | Balakin |
| 2010/0002774 A1 | 2/2010 | Balakin |
| 2010/0038552 A1 | 2/2010 | Trbojevic |
| 2010/0045213 A1 | 2/2010 | Sliski et al. |
| 2010/0046697 A1 | 2/2010 | Balakin |
| 2010/0060209 A1 | 3/2010 | Balakin |
| 2010/0090122 A1 | 4/2010 | Balakin |
| 2010/0091946 A1 | 4/2010 | Balakin |
| 2010/0102244 A1 | 4/2010 | Zdasiuk et al. |
| 2010/0126964 A1 | 5/2010 | Smith et al. |
| 2010/0127184 A1 | 5/2010 | Balakin |
| 2010/0128646 A1 | 5/2010 | Balakin |
| 2010/0141183 A1 | 6/2010 | Balakin |
| 2010/0171045 A1 | 7/2010 | Guneysal |
| 2010/0171447 A1 | 7/2010 | Balakin |
| 2010/0133444 A1 | 8/2010 | Balakin |
| 2010/0133448 A1 | 8/2010 | Balakin |
| 2010/0207552 A1 | 8/2010 | Balakin |
| 2010/0230617 A1 | 9/2010 | Gall |
| 2010/0230620 A1 | 9/2010 | Tsoupas et al. |
| 2010/0264327 A1 | 10/2010 | Bonig et al. |
| 2010/0266100 A1 | 10/2010 | Balakin |
| 2010/0278303 A1 | 11/2010 | Grodzins |
| 2010/0288945 A1 | 11/2010 | Gnutzmann et al. |
| 2010/0296534 A1 | 11/2010 | Levecq et al. |
| 2010/0308235 A1 | 12/2010 | Sliski et al. |
| 2010/0320404 A1 | 12/2010 | Tanke |
| 2010/0327187 A1 | 12/2010 | Beloussov et al. |
| 2011/0006214 A1 | 1/2011 | Bonig |
| 2011/0009738 A1 | 1/2011 | Maltz et al. |
| 2011/0011729 A1 | 1/2011 | Poehlmann-Martins et al. |
| 2011/0027853 A1 | 2/2011 | Bert et al. |
| 2011/0047469 A1 | 2/2011 | Baumann et al. |
| 2011/0051891 A1 | 3/2011 | O'Connor et al. |
| 2011/0101236 A1 | 5/2011 | Cameron et al. |
| 2011/0116528 A1 | 5/2011 | Balakin |
| 2011/0118531 A1 | 5/2011 | Balakin |
| 2011/0124976 A1 | 5/2011 | Sabczynski et al. |
| 2011/0127443 A1 | 6/2011 | Comer et al. |
| 2011/0147608 A1 | 6/2011 | Balakin |
| 2011/0166219 A1 | 7/2011 | Stockfleth |
| 2011/0180720 A1 | 7/2011 | Balakin |
| 2011/0180731 A1 | 7/2011 | Welsh |
| 2011/0182410 A1 | 7/2011 | Balakin |
| 2011/0150180 A1 | 8/2011 | Balakin |
| 2011/0166720 A1 | 8/2011 | Jongen et al. |
| 2011/0186720 A1 | 8/2011 | Jongen et al. |
| 2011/0196223 A1 | 8/2011 | Balakin |
| 2011/0214588 A1 | 9/2011 | Grubling et al. |
| 2011/0218430 A1 | 9/2011 | Balakin |
| 2011/0220794 A1 | 9/2011 | Censor et al. |
| 2011/0220798 A1 | 9/2011 | Baurichter et al. |
| 2011/0233423 A1 | 9/2011 | Balakin |
| 2011/0238440 A1 | 9/2011 | Leuschner |
| 2011/0240874 A1 | 10/2011 | Iwata |
| 2011/0248188 A1 | 10/2011 | Brusasco et al. |
| 2011/0266961 A1 | 11/2011 | Umezawa et al. |
| 2011/0266981 A1 | 11/2011 | Umezawa |
| 2011/0278477 A1 | 11/2011 | Balakin |
| 2011/0284757 A1 | 11/2011 | Butuceanu et al. |
| 2011/0284760 A1 | 11/2011 | Balakin |
| 2011/0285327 A1 | 11/2011 | Begg |
| 2011/0297850 A1 | 12/2011 | Claereboudt et al. |
| 2011/0299657 A1 | 12/2011 | Havelange et al. |
| 2011/0299919 A1 | 12/2011 | Stark et al. |
| 2011/0306870 A1 | 12/2011 | Kuhn |
| 2011/0313232 A1 | 12/2011 | Balakin |

(56) References Cited

U.S. PATENT DOCUMENTS

| | | |
|---|---|---|
| 2012/0001085 A1 | 1/2012 | Fujimoto et al. |
| 2012/0056098 A1 | 3/2012 | Behrens et al. |
| 2012/0056108 A1 | 3/2012 | Lomax |
| 2012/0061582 A1 | 3/2012 | Iwata |
| 2012/0069981 A1 | 3/2012 | Pomper et al. |
| 2012/0077748 A1 | 3/2012 | Vidyasagar et al. |
| 2012/0081582 A1 | 3/2012 | Iwata |
| 2012/0112092 A1 | 5/2012 | Pomper et al. |
| 2012/0119114 A1 | 5/2012 | Brauer |
| 2012/0119115 A1 | 5/2012 | Iwata |
| 2012/0136194 A1 | 5/2012 | Zhang et al. |
| 2012/0020727 A1 | 8/2012 | Pomper et al. |
| 2012/0143051 A1 | 8/2012 | Balakin |
| 2012/0160996 A1 | 8/2012 | Jongen |
| 2012/0199757 A1 | 8/2012 | Pu |
| 2012/0199767 A1 | 8/2012 | Pu |
| 2012/0205551 A1 | 8/2012 | Balakin |
| 2012/0209108 A1 | 8/2012 | Balakin |
| 2012/0223246 A1 | 9/2012 | Stephani et al. |
| 2012/0224887 A1 | 9/2012 | Cheng et al. |
| 2012/0242257 A1 | 9/2012 | Balakin |
| 2012/0248325 A1 | 10/2012 | Balakin |
| 2012/0264998 A1 | 10/2012 | Fujitaka et al. |
| 2012/0267543 A1 | 10/2012 | Noda et al. |
| 2012/0260150 A1 | 11/2012 | Jongen |
| 2012/0273666 A1 | 11/2012 | Bert et al. |
| 2012/0303384 A1 | 11/2012 | Stepaniak et al. |
| 2012/0313003 A1 | 12/2012 | Trbojevic |
| 2012/0326722 A1 | 12/2012 | Weinberg et al. |
| 2013/0001432 A1 | 1/2013 | Jongen |
| 2013/0043403 A1 | 2/2013 | Gordon et al. |
| 2013/0053616 A1 | 2/2013 | Gall et al. |
| 2013/0068938 A1 | 3/2013 | Heese |
| 2013/0072743 A1 | 3/2013 | Fieres et al. |
| 2013/0072744 A1 | 3/2013 | Moskvin et al. |
| 2013/0086500 A1 | 4/2013 | Kane et al. |
| 2013/0090549 A1 | 4/2013 | Meltsner et al. |
| 2013/0108014 A1 | 5/2013 | Tome et al. |
| 2013/0127375 A1 | 5/2013 | Sliski et al. |
| 2013/0131424 A1 | 5/2013 | Sliski et al. |
| 2013/0131433 A1 | 5/2013 | Katscher et al. |
| 2013/0150647 A1 | 6/2013 | Chen et al. |
| 2013/0187060 A1 | 7/2013 | Jongen |
| 2013/0193353 A1 | 8/2013 | Ikeda et al. |
| 2013/0208867 A1 | 8/2013 | Beckman |
| 2013/0209450 A1 | 8/2013 | Cohen et al. |
| 2013/0211482 A1 | 8/2013 | Piipponen |
| 2013/0217948 A1 | 8/2013 | Balakin |
| 2013/0217950 A1 | 8/2013 | Partanen et al. |
| 2013/0218009 A1 | 8/2013 | Balakin |
| 2013/0221213 A1 | 8/2013 | Takayanagi et al. |
| 2013/0237425 A1 | 9/2013 | Leigh et al. |
| 2013/0237822 A1 | 9/2013 | Gross et al. |
| 2013/0243722 A1 | 9/2013 | Basile et al. |
| 2013/0245113 A1 | 9/2013 | Stockfleth |
| 2013/0259335 A1 | 10/2013 | Mallya et al. |
| 2013/0267756 A1 | 10/2013 | Totake et al. |
| 2013/0277569 A1 | 10/2013 | Behrens et al. |
| 2013/0303824 A1 | 11/2013 | Stephani et al. |
| 2013/0324479 A1 | 12/2013 | Zhang et al. |
| 2013/0345489 A1 | 12/2013 | Beloussov et al. |
| 2014/0005483 A1 | 1/2014 | Jongen |
| 2014/0005484 A1 | 1/2014 | Bharat et al. |
| 2014/0018603 A1 | 1/2014 | Asaba |
| 2014/0021375 A1 | 1/2014 | Nishiuchi |
| 2014/0028220 A1 | 1/2014 | Bromberg et al. |
| 2014/0042934 A1 | 2/2014 | Tsutsui |
| 2014/0046113 A1 | 2/2014 | Fujimoto et al. |
| 2014/0061493 A1 | 3/2014 | Prieels et al. |
| 2014/0077899 A1 | 3/2014 | Boswell et al. |
| 2014/0086755 A1 | 3/2014 | Matteo et al. |
| 2014/0091734 A1 | 4/2014 | Gall et al. |
| 2014/0094371 A1 | 4/2014 | Zwart et al. |
| 2014/0094637 A1 | 4/2014 | Zwart et al. |
| 2014/0094638 A1 | 4/2014 | Gall et al. |
| 2014/0094639 A1 | 4/2014 | Zwart et al. |
| 2014/0094640 A1 | 4/2014 | Gall et al. |
| 2014/0094643 A1 | 4/2014 | Gall et al. |
| 2014/0094841 A1 | 4/2014 | Gall et al. |
| 2014/0097920 A1 | 4/2014 | Goldie et al. |
| 2014/0107390 A1 | 4/2014 | Brown et al. |
| 2014/0113388 A1 | 4/2014 | Bitter et al. |
| 2014/0121441 A1 | 5/2014 | Huber et al. |
| 2014/0128719 A1 | 5/2014 | Longfield |
| 2014/0145090 A9 | 5/2014 | Jongen |
| 2014/0193058 A1 | 7/2014 | Bharat et al. |
| 2014/0200448 A1 | 7/2014 | Schulte et al. |
| 2014/0221616 A1 | 8/2014 | Franke et al. |
| 2014/0257011 A1 | 9/2014 | Spotts |
| 2014/0257099 A1 | 9/2014 | Balakin |
| 2014/0275699 A1 | 9/2014 | Benna et al. |
| 2014/0308202 A1 | 10/2014 | Matusik et al. |
| 2014/0316184 A1 | 10/2014 | Fujimoto et al. |
| 2014/0320008 A1 | 10/2014 | Abs et al. |
| 2014/0330063 A1 | 11/2014 | Balakin |
| 2014/0332691 A1 | 11/2014 | Campbell et al. |
| 2014/0336438 A1 | 11/2014 | Bharat et al. |
| 2014/0350322 A1 | 11/2014 | Schulte et al. |
| 2014/0369958 A1 | 12/2014 | Basile |
| 2014/0371076 A1 | 12/2014 | Jongen |
| 2014/0371511 A1 | 12/2014 | Zwart et al. |
| 2015/0015167 A1 | 1/2015 | Ungaro et al. |
| 2015/0030223 A1 | 1/2015 | Pearlstein et al. |
| 2015/0041665 A1 | 2/2015 | Hollebeek et al. |
| 2015/0060703 A1 | 3/2015 | Ogasawara et al. |
| 2015/0076370 A1 | 3/2015 | Totake et al. |
| 2015/0080633 A1 | 3/2015 | Anferov |
| 2015/0080634 A1 | 3/2015 | Huber et al. |
| 2015/0087883 A1 | 3/2015 | Boudreau et al. |
| 2015/0087885 A1 | 3/2015 | Boisseau et al. |
| 2015/0087960 A1 | 3/2015 | Treffert |
| 2015/0090894 A1 | 4/2015 | Zwart et al. |
| 2015/0099917 A1 | 4/2015 | Bula et al. |
| 2015/0126797 A1 | 5/2015 | Aptaker et al. |
| 2015/0146856 A1 | 5/2015 | Beckman |
| 2015/0174429 A1 | 6/2015 | Zwart et al. |
| 2015/0196534 A1 | 7/2015 | Vidyasagar et al. |
| 2015/0196779 A1 | 7/2015 | Tonner |
| 2015/0209601 A1 | 7/2015 | Benna et al. |
| 2015/0217138 A1 | 8/2015 | Fujimoto et al. |
| 2015/0217139 A1 | 8/2015 | Bert et al. |
| 2015/0217140 A1 | 8/2015 | Balakin |
| 2015/0231411 A1 | 8/2015 | O'Neal, III et al. |
| 2015/0321025 A1 | 11/2015 | Freud et al. |
| 2015/0328483 A1 | 11/2015 | Odawara et al. |
| 2015/0335463 A1 | 11/2015 | De Gruytere |
| 2015/0335919 A1 | 11/2015 | Behar et al. |
| 2015/0337393 A1 | 11/2015 | Keller et al. |
| 2015/0343238 A1 | 12/2015 | Balakin |
| 2015/0352372 A1 | 12/2015 | Takayanagi et al. |
| 2015/0352374 A1 | 12/2015 | Gattiker et al. |
| 2015/0374324 A1 | 12/2015 | Nishimura et al. |
| 2016/0000387 A1 | 1/2016 | Buchsbaum et al. |
| 2016/0008631 A1 | 1/2016 | Harada et al. |
| 2016/0016010 A1 | 1/2016 | Schulte et al. |
| 2016/0048981 A1 | 2/2016 | Pearlstein et al. |
| 2016/0059039 A1 | 3/2016 | Liu |
| 2016/0067316 A1 | 3/2016 | Sunavala-Dossabhoy |
| 2016/0074675 A1 | 3/2016 | Moskvin et al. |
| 2016/0113884 A1 | 4/2016 | Lin et al. |
| 2016/0136457 A1 | 5/2016 | Jung et al. |
| 2016/0144201 A1 | 5/2016 | Schulte |
| 2016/0172066 A1 | 6/2016 | Claereboudt |
| 2016/0172067 A1 | 6/2016 | Claereboudt et al. |
| 2016/0175052 A1 | 6/2016 | Kumar et al. |
| 2016/0175617 A1 | 6/2016 | Spatola et al. |
| 2016/0199667 A1 | 7/2016 | Flynn et al. |
| 2016/0199671 A1 | 7/2016 | Jongen |
| 2016/0217139 A1 | 7/2016 | Kapur et al. |
| 2016/0220846 A1 | 8/2016 | Matteo et al. |
| 2016/0220847 A1 | 8/2016 | Benna et al. |
| 2016/0243232 A1 | 8/2016 | Pickett |
| 2016/0250501 A1 | 9/2016 | Balakin |
| 2016/0250503 A1 | 9/2016 | Balakin et al. |

(56) References Cited

U.S. PATENT DOCUMENTS

| | | |
|---|---|---|
| 2016/0256712 A1 | 9/2016 | Vahala et al. |
| 2016/0263404 A1 | 9/2016 | Mougenot |
| 2016/0270203 A1 | 9/2016 | Ungaro et al. |
| 2016/0271424 A1 | 9/2016 | Lee et al. |
| 2016/0287899 A1 | 10/2016 | Park et al. |
| 2016/0296766 A1 | 10/2016 | El Fakhri et al. |
| 2016/0303399 A1 | 10/2016 | Balakin |
| 2016/0331999 A1 | 11/2016 | Hartman et al. |
| 2017/0028220 A1 | 2/2017 | Censor et al. |
| 2017/0128746 A1 | 5/2017 | Zwart et al. |
| 2017/0157422 A1 | 6/2017 | Zwart et al. |
| 2017/0157424 A1 | 6/2017 | Zwart et al. |
| 2017/0157425 A1 | 6/2017 | Zwart et al. |
| 2017/0182338 A1* | 6/2017 | Zwart .............. A61N 5/1077 |
| 2017/0229205 A1* | 8/2017 | Debatty ............ H01J 37/3002 |
| 2017/0281981 A1 | 10/2017 | Mansfield |
| 2017/0340900 A1 | 11/2017 | Moore et al. |
| 2018/0020535 A1 | 1/2018 | Cooley et al. |
| 2018/0099158 A1 | 4/2018 | Brusasco |
| 2018/0236268 A1 | 8/2018 | Zwart et al. |
| 2018/0277277 A1* | 9/2018 | Gerbershagen ......... G21K 5/04 |
| 2019/0022407 A1 | 1/2019 | Abel et al. |
| 2019/0022411 A1 | 1/2019 | Parry et al. |
| 2019/0060667 A1 | 2/2019 | Vanderstraeten et al. |
| 2020/0164224 A1 | 5/2020 | Vanderstraten et al. |
| 2020/0269068 A1 | 8/2020 | Abel et al. |
| 2020/0286601 A1 | 9/2020 | Khuntia et al. |
| 2020/0298023 A1 | 9/2020 | Cooley, III et al. |
| 2020/0330798 A1 | 10/2020 | Trail et al. |
| 2021/0016108 A1 | 1/2021 | Khuntia et al. |
| 2021/0027973 A1 | 1/2021 | Star-Lack et al. |
| 2021/0052917 A1 | 2/2021 | Vanderstraeten et al. |
| 2021/0101023 A1 | 4/2021 | Abel et al. |
| 2021/0113856 A1 | 4/2021 | Smith et al. |
| 2021/0128946 A1 | 5/2021 | Smith et al. |
| 2021/0308485 A1 | 10/2021 | Koponen et al. |
| 2021/0308486 A1 | 10/2021 | Perez et al. |

FOREIGN PATENT DOCUMENTS

| | | |
|---|---|---|
| CN | 1537657 A | 10/2004 |
| CN | 1816243 A | 8/2006 |
| CN | 101061759 A | 10/2007 |
| CN | 101546617 A | 9/2009 |
| CN | 101932361 A | 12/2010 |
| CN | 101933405 A | 12/2010 |
| CN | 101933406 A | 12/2010 |
| CN | 102172106 A | 8/2011 |
| CN | 102316661 A | 1/2012 |
| CN | 102387836 A | 3/2012 |
| CN | 102586318 A | 7/2012 |
| CN | 103566488 A | 2/2014 |
| CN | 105169572 A | 12/2015 |
| CN | 106902476 A | 6/2017 |
| CN | 108785874 A | 11/2018 |
| CN | 108883295 A | 11/2018 |
| CN | 109195664 A | 1/2019 |
| DE | 2753397 A1 | 8/1978 |
| DE | 3148100 A1 | 6/1983 |
| DE | 3530446 A1 | 3/1986 |
| DE | 4101094 C1 | 5/1992 |
| DE | 4411171 A1 | 10/1995 |
| EP | 0194728 A1 | 9/1986 |
| EP | 0208163 A1 | 1/1987 |
| EP | 0221987 A1 | 5/1987 |
| EP | 0222786 A1 | 5/1987 |
| EP | 0277521 A2 | 8/1988 |
| EP | 0306966 A2 | 3/1989 |
| EP | 0388123 A2 | 9/1990 |
| EP | 0465597 A1 | 1/1992 |
| EP | 0499253 A2 | 8/1992 |
| EP | 0776595 A1 | 6/1997 |
| EP | 0864337 A2 | 9/1998 |
| EP | 0911064 A2 | 4/1999 |
| EP | 1069809 A1 | 1/2001 |
| EP | 1153398 A1 | 11/2001 |
| EP | 1294445 A2 | 3/2003 |
| EP | 1348465 A1 | 10/2003 |
| EP | 1358908 A1 | 11/2003 |
| EP | 1371390 A1 | 12/2003 |
| EP | 1402923 A1 | 3/2004 |
| EP | 1430932 A1 | 6/2004 |
| EP | 1454653 A1 | 9/2004 |
| EP | 1454654 A2 | 9/2004 |
| EP | 1454655 A2 | 9/2004 |
| EP | 1454656 A2 | 9/2004 |
| EP | 1454657 A2 | 9/2004 |
| EP | 1477206 A1 | 11/2004 |
| EP | 1605742 A1 | 12/2005 |
| EP | 1684313 A2 | 7/2006 |
| EP | 1738798 A2 | 1/2007 |
| EP | 1826778 A2 | 8/2007 |
| EP | 1949404 A2 | 7/2008 |
| EP | 2183753 A1 | 5/2010 |
| EP | 2227295 A1 | 9/2010 |
| EP | 2232961 A1 | 9/2010 |
| EP | 2232962 A2 | 9/2010 |
| EP | 2363170 A1 | 9/2011 |
| EP | 2363171 A1 | 9/2011 |
| EP | 2394498 A2 | 12/2011 |
| EP | 2910276 A1 | 8/2015 |
| FR | 2560421 A1 | 8/1985 |
| FR | 2911843 A1 | 8/2008 |
| GB | 0957342 A | 5/1964 |
| GB | 2015821 A | 9/1979 |
| GB | 2361523 A | 10/2001 |
| JP | 56-141000 | 8/1963 |
| JP | 61-225798 | 10/1966 |
| JP | 63-226699 | 9/1968 |
| JP | S47-028762 U | 12/1972 |
| JP | U46-108098 | 12/1973 |
| JP | 57-162527 | 10/1982 |
| JP | 61-80800 | 4/1986 |
| JP | 63-149344 | 6/1986 |
| JP | 62-150804 | 7/1987 |
| JP | 62-166500 | 8/1987 |
| JP | 63-218200 | 9/1988 |
| JP | 64-89621 | 4/1989 |
| JP | 01-276797 | 11/1989 |
| JP | 01-302700 | 12/1989 |
| JP | 4-94196 | 3/1992 |
| JP | 06-036893 | 8/1994 |
| JP | 06-233831 | 8/1994 |
| JP | 07-260939 | 10/1995 |
| JP | 07-263196 | 10/1995 |
| JP | 08-173890 | 7/1996 |
| JP | 08-264298 | 10/1996 |
| JP | 09-162585 | 6/1997 |
| JP | 10-071213 | 3/1998 |
| JP | H 11408 A | 1/1999 |
| JP | 11-47287 | 2/1999 |
| JP | 11-102800 | 4/1999 |
| JP | 11-243295 | 9/1999 |
| JP | 2000-243309 A | 9/2000 |
| JP | 2000-294399 A | 10/2000 |
| JP | 2001-6900 | 1/2001 |
| JP | 2001-009050 A | 1/2001 |
| JP | 2001-129103 A | 5/2001 |
| JP | 2001-346893 A | 12/2001 |
| JP | 2002-164686 A | 6/2002 |
| JP | 2003-504628 A | 2/2003 |
| JP | 2005-526578 A | 9/2005 |
| JP | 2006-032282 A | 2/2006 |
| JP | 2006-507826 A | 3/2008 |
| JP | 04-128717 B2 | 7/2008 |
| JP | 04-129768 B2 | 8/2008 |
| JP | 2009045229 A | 3/2009 |
| JP | 2009-515671 A | 4/2009 |
| JP | 2009-516905 A | 4/2009 |
| JP | 04-273409 B2 | 6/2009 |
| JP | 04-337300 B2 | 9/2009 |
| JP | 43-23267 B2 | 9/2009 |
| JP | 2010-536130 A | 11/2010 |
| JP | 2011-505191 A | 2/2011 |

(56) References Cited

FOREIGN PATENT DOCUMENTS

| | | |
|---|---|---|
| JP | 2011-505670 A | 2/2011 |
| JP | 2011-507151 A | 3/2011 |
| JP | 2011-224342 A | 11/2011 |
| JP | 05-046928 B2 | 10/2012 |
| JP | 05-341352 B2 | 11/2013 |
| SU | 300137 | 6/1969 |
| SU | 569635 A1 | 8/1977 |
| TW | 200930160 A | 7/2009 |
| TW | 200934662 A | 8/2009 |
| TW | 200939908 A | 9/2009 |
| TW | 200940120 A | 10/2009 |
| WO | WO-1986/07229 A1 | 12/1986 |
| WO | WO-1990/012413 A1 | 10/1990 |
| WO | WO-1992/03028 A1 | 2/1992 |
| WO | WO-1993/02536 A1 | 2/1993 |
| WO | 1996006519 | 2/1996 |
| WO | WO-1998/17342 A2 | 4/1998 |
| WO | WO-1999/39385 A1 | 8/1999 |
| WO | WO-2000/40064 A2 | 7/2000 |
| WO | WO-2000/49624 A1 | 8/2000 |
| WO | WO-2001/026230 A1 | 4/2001 |
| WO | WO-2001/026569 A1 | 4/2001 |
| WO | WO-02/07817 | 1/2002 |
| WO | WO-2003/039212 A1 | 5/2003 |
| WO | WO-03065382 A1 * 8/2003 ............... G21K 1/10 |
| WO | WO-2003/092812 A1 | 11/2003 |
| WO | WO-2004/026401 A1 | 4/2004 |
| WO | WO-2004/101070 A1 | 11/2004 |
| WO | WO-2004/103145 A2 | 12/2004 |
| WO | WO-2006-012467 A2 | 2/2006 |
| WO | WO-2007/061937 A2 | 5/2007 |
| WO | WO-2007/084701 A1 | 7/2007 |
| WO | WO-2007/130164 A2 | 11/2007 |
| WO | WO-2007/145906 A2 | 12/2007 |
| WO | WO-2008/030911 A2 | 3/2008 |
| WO | WO-2008/081480 A1 | 7/2008 |
| WO | WO-2009/048745 A2 | 4/2009 |
| WO | WO-2009/070173 A1 | 6/2009 |
| WO | WO-2009/070588 A1 | 6/2009 |
| WO | WO-2009/073480 A2 | 6/2009 |
| WO | WO-2014/018706 A1 | 1/2014 |
| WO | WO-2014/018876 A1 | 1/2014 |
| WO | 2017082984 A | 5/2017 |
| WO | 2017173443 | 10/2017 |
| WO | 2018/128822 A1 | 7/2018 |
| WO | 2019016249 | 1/2019 |
| WO | 2019016301 | 1/2019 |
| WO | 2019016305 | 1/2019 |
| WO | 2019016312 | 1/2019 |
| WO | 2019016326 | 1/2019 |
| WO | 2019018341 | 1/2019 |
| WO | 2019018376 | 1/2019 |
| WO | 2019018813 | 1/2019 |

OTHER PUBLICATIONS

Communication pursuant to Rules 161(1) & 162 EPC for European Patent Application No. 20717010.1, Issued Oct. 22, 2021, (3 Pages.).
Magliari, MS CMD, "FLASH Radiotherapy:A Look at Ultra-high Dose Rate Research and Treatment Plans", AAMD National Meeting, 2019, (47 pages).
Katalin Hideghéty et al., "Potential Clinical Application of Lazer Driven Ionizing Radiations", Prague ELIMEDICS Workshop, Mar. 2016, (58 pages).
Montay-Gruel P et al. Irradiation in a flash: Unique sparing of memory in mice after whole brain irradiation with dose rates above 100 Gy/s. Radiother Oncol (2017), http://dx.doi.org/10.1016/j.radonc.2017.05.03.
First Office Action (Chinese Translation), for CN20150245322.7, 8 pages (Oct. 29, 2018).
First Office Action (English Translation), for CN20150245322.7, 11 pages (Oct. 29, 2018).
Second Communication under Rule 71 (3) EPC for EP15155935.8, 100 pages (Oct. 25, 2017).
18th Japan Conference on Radiation and Radioisotopes [Japanese], Nov. 25-27, 1987, 9 pages.
510(k) Summary: Ion Beam Applications S.A., FDA, Jul. 12, 2001, 5 pages.
510(k) Summary: Optivus Proton Beam Therapy System, Jul. 21, 2000, 5 pages.
Abrosimov et al., 1000MeV Proton Beam Therapy facility at Petersburg Nuclear Physics Institute Synchrocyclotron, Medical Radiology (Moscow) 32, 10 (1987) revised in Journal of Physics, Conference Series 41, 2006, pp. 424-432, Institute of Physics Publishing Limited.
Abrosimov et al., Neutron Time-of-flight Spectrometer Gneis at the Gatchina 1 GeV Proton Syncrhocyclotron, Mar. 9, 1985 and revised form Jul. 31, 1985, Lemingrad Nuclear Physics Institute, Gatchina, 188350, USSR (15 pages).
Adachi et al., A 150MeV FFAG Synchrotron with Return-Yoke Free Magent, Proceedings of the 2001 Particle Accelerator Conference, Chicago, 2001, 3 pages.
Ageyev et al., The IHEP Accelerating and Storage Complex (UNK) Status Report, 11th International Conference on High-Energy Accelerators, 1980, pp. 60-70.
Agosteo et al., Maze Design of a gantry room for proton therapy, Nuclear Instruments & Methods in Physics Research, 1996, Section A. 382, pp. 573-582.
Alexeev et al., R4 Design of Superconducting Magents for Proton Synchrotrons, Proceedings of the Fifth International Cryogenic Engineering Conference, 197 4, pp. 531-533.
Allardyce et al., Performance and Prospects of the Reconstructed CERN 600 MeV Synchrocyclotron, IEEE Transactions on Nuclear Science USA, Jun. 1977, ns-24:(3) 1631-1633.
Alonso, Magnetically Scanned Ion Beams for Radiation Therapy, Accelerator & Fusion Research Division, Lawrence Berkeley Laboratory, Berkeley, CA, Oct. 1988, 13 pages.
Amaldi et al., The Italian project for a hadrontherapy centre Nuclear Instruments and Methods in Physics Research A, 1995, 360, pp. 297-301.
Amaldi, Overview of the world landscape of Hadrontherapy and the projects of the TERA foundation, Physica Medica, an International journal Devoted to the Applications of Physics to Medicine and Biology, Jul. 1998, vol. XIV, Supplement 1, 6th Workshop on Heavy Charged Particles in Biology and Medicine, Instituto Scientific Europeo (ISE), Sep. 29-Oct. 1, 1977, Baveno, pp. 76-85.
An Accelerated Collaboration Meets with Bearning Success, Lawrence Livermore National Laboratory, Apr. 12, 2006, S&TR, Livermore, California, pp. 1-3, http://www.linl.gov/str/April06/Caporaso.html.
Anferov et al., Status of the Midwest Proton Radiotherapy Institute, Proceedings of the 2003 Particle Accelerator Conference, 2003, pp. 699-701.
Anferov et al., The Indiana University Midwest Proton Radiation Institute, Proceedings of the 2001 Particle Accelerator Conference, 2001, Chicago, pp. 645-647.
Appun, Various problems of magnet fabrication for high-energy accelerators, Journal for All Engineers Interested in the Nuclear Field, 1987, 11 pp. 10-16 (1967) [Lang.: German], English bibliographic information (http://www.osti.1mv/enernvcitations/product.biblio.isn?ostiid=4442292).
Arduini et al. Physical specifications of clinical proton beams from a synchrotron, Med, Phys, Jun. 1996, 23 (6): 939-951.
Badano et al., Proton-Ion Medical Machine Study (PIMMS) Part I, PIMMS, Jan. 1999, 238 pages.
Beam Delivery and Properties, Journal of the ICRU, 2007, 7(2):20 pages.
Beeckman et al., Preliminary design of a reduced cost proton therapy facility using a compact, high field isochrenous cyclotron, Nuclear Instruments and Methods in Physics Research 856/57, 1991, pp. 1201-1204.
Bellomo et al., The Superconducting Cyclotron Program at Michigan State University, Bulletin of the American Physical Society, Sep. 1980, 25(7):767.

(56) References Cited

OTHER PUBLICATIONS

Benedikt and Carli, Matching to Gantries for Medical Synchrotrons IEEE Proceedings of the 1997 Particle Accelerator Conference, 1997, pp. 13 79-13 81.

Bieth et al., A Very Compact Protontherapy Facility Based on an Extensive Use of High Temperature Superconductors (HTS) Cyclotrons and their Applications 1998, Proceedings of the Fifteenth International Conference on Cyclotrons and their Applications, Caen, Jun. 14-19, 1998, pp. 669-672.

Bigham, Magnetic Trim Rods for Superconducting Cyclotrons, Nuclear Instruments and Methods (North-Holland Publishing Co.), 1975, 141:223-228.

Bimbot, First Studies of the External Beam from the Orsay S.C. 200 MeV, Institut de Physique Nucleaire, BP 1, Orsay, France, IEEE, 1979, pp. 1923-1926.

Blackmore et al., Operation of the Triumf Proton Therapy Facility, IEEE Proceedings of the 1997 Particle Accelerator Conference, May 12-16, 1997, 3:3831-3833.

Bloch, The Midwest Proton Therapy Center, Application of Accelerators in Research and Industry, Proceedings of the Fourteenth Int'l. Conf, Part Two, Nov. 1996, pp. 1253-1255.

Blosser et al., A Compact Superconducting Cyclotron for the Production of High Intensity Protons, Proceedings of the 1997 Particle Accelerator Conference, May 12-16, 1997, 1:1054-1056.

Blosser et al., Advances in Superconducting Cyclotrons at Michigan State University, Proceedings of the 11th International Conference on Cyclotrons and their Applications, Oct. 1986, pp. 157-167, Tokyo.

Blosser et al., Characteristics of a 400 (Q2/A) MeV Super-Conducting Heavy-Ion Cyclotron, Bulletin of the American Physical Society, Oct. 1974, p. 1026.

Blosser et al., Medical Accelerator Projects at Michigan State Univ. IEEE Proceedings of the 1989 Particle Accelerator Conference, Mar. 20-23, 1989, 2:742-746.

Blosser et al., Problems and Accomplishments of Superconducting Cyclotrons, Proceedings of the 14th International Conference, Cyclotrons and Their Applications, Oct. 1995, pp. 674-684.

Blosser et al., Progress toward an experiment to study the effect of RF grounding in an internal ion source on axial oscillations of the beam in a cyclotron, National Superconducting Cyclotron Laboratory, Michigan State University, Report MSUCL-760, CP600, Cyclotrons and their Applications 2011, Sixteenth International Conference, 2001, pp. 274-276.

Blosser et al., Superconducting Cyclotron for Medical Application, IEEE Transactions on Magnetics, Mar. 1989, 25(2): 1746-1754.

Blosser et al., Superconducting Cyclotrons, Seventh International Conference on Cyclotrons and their Applications, Aug. 19-22, 1975, pp. 584-594.

Blosser H.G.et al. "Progress on the Coupled Superconducting Cyclotron Project," Bulletin of the American Physical Society, 1993 (p. 3).

Blosser, Application of Superconductivity in Cyclotren Construction, Ninth International Conference on Cyclotrons and their Applications, Sep. 1981, pp. 147-157.

Blosser, Applications of Superconducting Cyclotrons, Twelfth International Conference on Cyclotrons and Their Applications, May 8-12, 1989, pp. 137-144.

Blosser, Future Cyclotrons, AIP, The Sixth International Cyclotron Conference, 1972, pp. 16-32.

Blosser, H., Present and Future Superconducting Cyclotrons, Bulletin of the American Physical Society, Feb. 1987, 32(2):171 Particle Accelerator Conference, Washington, D.C.

Blosser, H.G., Superconducting Cyclotrons at Michigan State University, Nuclear Instruments & Methods in Physics Research, 1987, vol. B 24/25, part II, pp. 752-756.

Blosser, Medical Cyclotrons, Physics Today, Special Issue Physical Review Centenary, Oct. 1993, pp. 70-73.

Blosser, Preliminary Design Study Exploring Building Features Required for a Proton Therapy Facility for the Ontario Cancer Institute, Mar. 1991, MSUCL-760a, 53 pages.

Blosser, Progress on the Coupled Superconducting Cyclotron Project, Bulletin of the American Physical Society, 1993 (p. 3).

Blosser, Synchrocyclotron Improvement Programs, IEEE Transactions on Nuclear Science USA, Jun. 1969, 16(3):Part 1, pp. 405-414.

Blosser, The Michigan State University Superconducting Cyclotron Program, Nuclear Science, Apr. 1979, NS-26(2):2040-2047.

Botha et al., A New Multidisciplinary Separated-Sector Cyclotron Facility, IEEE Transactions on Nuclear Science, 1977, NS-24(3): 1118-1120.

Chichili et al., Fabrication of Nb3Sn Shell-Type Coils with Pre-Preg Ceramic Insulation, American Institute of Physics Conference Proceedings, AIP USA, No. 711, (XP-002436709, ISSN: 0094-243X), 2004, pp. 450-457.

Chong et al., Radiology Clinic North American 7. 3319, 1969, 27 pagas.

Chu et al., Instrumentation for Treatment of Cancer Using Proton and Light-ion Beams, Review of Scientific Instruments, Aug. 1993, 64 (8):2055-2122.

Chu et al., Performance Specifications for Proton Medical Facility, Lawrence Berkeley Laboratory, University of California, Mar. 1993, 128 pages.

Chu, Instrumentation in Medical Systems, Accelerator and Fusion Research Division, Lawrence Berkeley Laboratory, University of California, Berkeley, CA, May 1995, 9 pages.

Cole et al., Design and Application of a Proton Therapy Accelerator, Fermi National Accelerator Laboratory, IEEE, 1985, 5 pages.

Collins, et al., The Indiana University Proton Therapy System, Proceedings of EPAC 2006, Edinburgh, Scotland, 2006, 3 pages.

Communication pursuant to Article 94(3) EPC for EP15155935.8, 3 pages (May 22, 2017).

Communication pursuant to Article 94(3) EPC, 4 pages (Jul. 7, 2016).

Communication under Rule 71(3) EPC for EP15155935.8, 100 pages (Mar. 24, 2017).

Conradi et al., Proposed New Facilities for Proton Therapy at iThemba Labs, Proceedings of EPAC, 2002, pp. 560-562.

C/E Source of Ions for Use in Sychro-Cyclotrons Search, Jan. 31, 2005, 9 pages.

Cosgrove et al., Microdosimetric Studies on the Orsay Proton Synchrocyclotron at 73 and 200 MeV, Radiation Protection Dosimetry, 1997, 70(1-4):493-496.

Coupland, High-field (5 T) pulsed superconducting dipole magnet, Proceedings of the Institution of Electrical EnRineers, Jul. 1974, 121(7):771-778.

Coutrakon et al. Proton Synchrotrons for Cancer Therapy, Application of Accelerators in Research and Industry—Sixteenth International Conf., American Institute of Physics, Nov. 1-5, 2000, vol. 576, pp. 861-864.

Coutrakon et al., A prototype beam delivery system for the proton medical accelerator at Loma Linda, Medical Physics, Nov./Dec. 1991, 18(6):1093-1099.

CPAC Highlights Its Proton Therapy Program at ESTRO Annual Meeting, TomoTherapy Incorporated, Sep. 18, 2008, Madison, Wisconsin, pp. 1-2.

Cuttone, Applications of a Particle Accelerators in Medical Physics, Istituto Nazionale di Fisica Nucleare-Laboratori Nazionali del Sud, V.S. Sofia, 44 Cantania, Italy, Jan. 2010, 17 pages.

Dahl P, Superconducting Magnet System, American Institute of Physics, AIP Conference Proceedings, 1987-1988, 2: 1329-1376.

Dialog Search, Jan. 31, 2005, 17 pages.

Dugan et al., Tevatron Status IEEE, Particle Accelerator Conference, Accelerator Science & Technology, 1989, pp. 426-430.

Eickhoff et al., The Proposed Accelerator Facility for Light Ion Cancer Therapy in Heidelberg, Proceedings of the 1999 Particle Accelerator Conference, New York, 1999, pp. 2513-2515.

Enchevich et al., Minimizing Phase Losses in the 680 MeV Synchrocyclotron by Correcting the Accelerating Voltage Amplitude, Atomnaya Energiya, 1989, 26:(3):315-316.

Endo et al., Compact Proton and Carbon Ion Synchrotrons for Radiation Therapy, Proceedings of EPAC 2002. Paris France, 2002, pp. 2733-2735.

Extended European Search Report in European counterpart application 15155935.8 mailed Jun. 10, 2015 (5 pages).

(56) References Cited

OTHER PUBLICATIONS

Flanz et al., Large Medical Gantries, Particle Accelerator Conference, Massachusetts General Hospital, 1995, pp. 1-5.
Flanz et al., Operation of a Cyclotron Based Proton Therapy Facility, Massachusetts General Hospital, Boston, MA 02114, pp. 1-4, retrieved from Internet in 2009.
Flanz et al., The Northeast Proton Therapy Center at Massachusetts General Hospital, Fifth Workshop on Heavy Charge Particles in Biology and Medicine, GSI, Darmstadt,Aug. 1995, 11 pages.
Flanz et al., Treating Patients with the NPTC Accelerator Based Prolon Treatment Facility, Proceedings of the 2003 Particle Accelerator Conference, 2003, pp. 690-693.
Flood and Frazier, The Wide-Band Driven RF System for the Berkeley 88-Inch Cyclotron, American Institute of Physics, Conference Proceedings., No. 9, 1972, 459-466.
Foster and Kashikhin, Superconducting Superferric Dipole Magent with Cold Iron Core for the VLHC, IEEE Transactions on Applied Superconductivity, Mar. 2002, 12(1):111-115.
Friesel et al., Design and Construction Progress on the IUCF Midwest Proton Radiation Institute, Proceedings of EPAC 2002, 2002, pp. 2736-2738.
Fukumoto et al., A Proton Therapy Facility Plan Cyclotrons and their Applications, Proceedings of the 13th International Conference, Vancouver, Canada, Jul. 6-10, 1992, pp. 258-261.
Fukumoto, Cyclotron Versus Synchrotron for Proton Beam Therapy, KEK Prepr., No. 95-122, Oct. 1995, pp. 533-536.
Goto et al., Progress on the Sector Magnets for the Riken SRC, American Institute of Physics, 714 CP600, Cyclotrons and Their Applications 2001, Sixteenth International Conference, 2001, pp. 319-323.
Graffman et al., Design Studies for a 200 MeV Proton Clinic for Radiotherapy, AIP Conference Proceedings: Cyclotrons—1972, 1972, No. 9. pp. 603-615.
Graffman, et. al. Proton radiotherapy with the Uppsala cyclotron. Experience and plans Strahlentherapie, 1985, 161(12):764-770.
Graffman, S., et al., Clinical Trials in Radiotherapy and the Merits of High Energy Protons, Acta Radiol. Therapy Phys. Biol. 9:1-23 (1970).
Hede, Research Groups Promoting Proton Therapy Lite, Journal of the National Cancer Institute, Dec. 6, 2006, 98(23):1682-1664.
Heinz, Superconducting Pulsed Magnetic Systems for High-Energy Synchrotrons, Proceedings of the Fourth International Cryogenic Engineering Conference, May 24-26, 1972, pp. 55-63.
Hentschel et al., Plans for the German National Neutron Therapy Centre with a Hospital-Based 70 MeV Proton Cyclotron at University Hospital Essen/Germany, Cyclotrons and their Applications, Proceedings of the Fifteenth International Conference on Cyclotrons and their Applications, Caen, Franco, Jun. 14-19, 1996, pp. 21-23.
Hepburn et al., Superconducting Cyclotron Neutron Source for Therapy, International Journal of Radiation Oncology Biology Physics, vol. 3 complete, 1977, pp. 367-391.
Hirabayashi, Development of Superconducting Magnets for Beam Lines and Accelerator at KEK, IEEE Transaction on Magnetics, Jan. 1981, Mag-17(1 ):728-731.
Indiana's mega-million proton therapy cancer center welcomes its first patients [online] Press release, Health & Medicine Week, 2004, retrieved from NewsRx.com, Mar. 1, 2004, pp. 119-120.
Ishibashi and Mcinturff, Stress Analysis of Superconducting 1 OT Magnets for Synchrotron, Proceedings of the Ninth International Cryogenic Engineering Conference, May 11-14, 1982, pp. 513-516.
Ishibashi and Mcinturff, Winding Design Study of Superconducting 10 T Dipoles for a Synchrotron, IEEE Transactions on Magnetics, May 1983, MAG-19(3):1364-1367.
Jahnke et al., First Superconducting Prototype Magnets for a Compact Synchrotron Radiation Source in Operation, IEEE Transactions on Magnetics, Mar. 1988, 24(2):1230-1232.

Jones and Dershem, Synchrotron Radiation from Proton in a 20 TEV, 10 TESLA Superconducting Super Collider Proceedings of the 12th International Conference on High-Energy Accelerator, Aug. 11-16, 1983, pp. 138-140.
Jones and Mills, The South African National Accelerator Centre: Particle Therapy and Isotope Production Programmes, Radiation Physics and Chemistry, Apr.-Jun. 1998, 51 ( 4-6):571-578
Jones et al., Status Report of the NAC Particle Therapy Programme, Stralentherapie und Onkologie, vol. 175, Supol. II, Jun. 1999, pp. 30-32.
Jones, Present Status and Future Trends of Heavy Particle Radiotherapy, Cyclotrons and their Applications 1996, Proceedings of the Fifteenth International Conference on Cyclotrons and their Applications, Jun. 14-19, 1998, pp. 13-20.
Jones, Progress with the 200 MeV Cyclotron Facility at the National Accelerator Centre, Commission of the European Communities Radiation Protection Proceedings, Fifth Symposium on Neutron Dosimetry, Sep. 17-21, 1964, vol. II, pp. 989-998.
Jongen et al., "Progress report on the IBA-SHI small cyclotron for cancer therapy" Nuclear Instruments and Methods in Physics Research, Section B, vol. 79, issue 1-4, 1993, pp. 885-889 (Abstract).
Jongen et al., Development of a Low-cost Compact Cyclotron System for Proton Therapy, National Institute of Radioi. Sci, 1991, No. 81, DD. 189-200.
Jongen et al., Progress report on the IBA-SHI small cyclotron for cancer therapy Nuclear Instruments and Methods in Physics Research, Section B, vol. 79, issue 1-4, 1993, pp. 885-889.
Jongen et al., The proton therapy system for MGH's NPTC: equipment description and progress report, Bulletin du Cancer/Radiotherapie, Proceedings of the meeting of the European Heavy Particle Therapy Group, 1996, 83(Suppl. 1):219-222.
Jongen et al., The proton therapy system for the NPTC: Equipment Description and progress report, Nuclear Instruments and methods in physics research, 1998, Section B, 113(1 ): 522-525.
Kanai et al., Three-dimensional Beam Scanning for Proton Therapy, Nuclear Instruments and Methods in Physic Research, Sep. 1, 1983, The Netherlands, 214(23):491-496.
Karlin et al., Medical Radiology (Moscow), 1983, 28, 13
Karlin et al., The State and Prospects In the Development of the Medical Proton Tract on the Synchrocyclotron in Gatchina, Med. Radial., Moscow, 28(3):28-32 (Mar. 1983)(German with English Abstract on end of p. 32).
Kats and Druzhinin, Comparison of Methods for Irradiation Prone Patients, Atomic Energy, Feb. 2003, 94(2): 120-123.
Kats and Onosovskii, A Planar Magnetooptical System for the Irradiation of a Lying Patient with a Proton Beam from Various Directions, Instruments and Experimental Techniques, 1996, 39(1):127-131.
Kats and Onosovskil, A Simple, Compact, Flat System for the Irradiation of a Lying Patient with a Proton Beam from Different Directions, Instruments and Experimental Techniques, 1996. 39(1):132-134.
Khoroshkov et al., Moscow Hospital-Based Proton Therapy Facility Design, Am. Joumal Clinical Oncology: CCT, Apr. 1994, 17(2):109-114.
Kim and Blosser, Optimized Magnet for a 250 MeV Proton Radiotherapy Cyclotron, Cyclotrons and Their Applications 2001. May 2001. Sixteenth International Conference, pp. 345-347.
Kim and Yun, A Light-Ion Superconducting Cyclotron System for Multi-Disciplinary Users, Journal of the Korean Physical Society. Sep. 2003, 43(3):325-331.
Kim et al., Construction of BT Magnet Test Stand for Cyclotron Studies, IEEE Transactions on Applied Superconductivity, Mar. 1993, 3(1):266-268.
Kim et al., Design Study of a Superconducting Cyclotron for Heavy Ion Therapy, Cyclotrons and Their Applications 2001, Sixteenth International Conference, May 13-17, 2001, pp. 324-326
Kim et al., Trim Coil System for the Riken Cyclotron Ring Cyclotron, Proceedings of the 1997 Particle Accelerator Conference, IEEE, Dec. 1981, vol. 3, pp. 214-235 or 3422-3424, 1998.
Kim, An Eight Tesla Superconducting Magnet for Cyclotron Studies, Ph.D. Dissertation, Michigan State University, Department of Physics and Astronomy, 1994, 13 8 pages.

(56) References Cited

OTHER PUBLICATIONS

Kirnstrand, Beam Modelling for Treatment Planning of Scanned Proton Beams, Digital Comprehensive Summaries of Uppsala dissertations from the Faculty of Medicine 330, Uppsala Universitet, 2008, 58 pages.
Kishida and Yano, Seam Transport System for the RIKEN SSC (II), Scientific Papers of the Institute of Physical and Chemical Research, Dec. 1981, 75(4):214-235.
Koehler et al., Range Modulators for Protons and Heavy Ions, Nuclear Instruments and Methods, 1975, vol. 131, pp. 437-440.
Koto and Tsujil, Future of Particle Thera12y, Ja12anese Journal of Cancer Clinics, 2001, 47(1):95-98 [Lang.: Japanese], English abstract (htt12://sciencelinks.j12/jeast/article/200206/000020020601A05 | | 453 .nhn).
Kraft et al., Hadrontherapy in Oncology, U. Amaldi and Larsson, editors Elsevier Science, 1994, 161 pages.
Krevet et al., Design of a Strongly Curved Superconducting Bending Magnet for a Compact Synchrotron Light Source, Advances in Cryogenic Engineering. 1988, vol. 33, pp. 25-32.
Laisne et al., The Orsay 200 MeV Synchrocyclotron, IEEE Transactions on Nuclear Science. Apr. 1979, NS-26(2):1919-1922.
Larsson, B., et al., "The High-Energy Proton Beam as a Neurosurgical Tool," Nature vol. 182, pp. 1222-1223 (1958).
Larsson, Biomedical Program for the Converted 200-MeV Synchrocyclotron at the Gustaf Werner Institute, Radiation Research, 1985, 104:S310-S318
Lawrence et al., Heavy particles in acromegaly and Cushing's Disease, in Endocrine and Norendocrine Hormone Producing Tumors (Year Book Medical Chicago, 1973, pp. 29-61
Lawrence et al., Successful Treatment of Acromegaly: Metabolic and Clinical Studies in 145 Patients, The Journal of Clinical Endocrinology and Metabolism, Aug. 1970, 31(2), 21 pages.
Lawrence et al., Treatment of Pituitary Tumors, (Excerpta medica, Amsterdamy/American Elsevier, New York, 1973, pp. 253-262.
Lawrence, J.H., Proton Irradiation of the Pituitary Cancer, vol. 10, pp. 795-798 (1957).
Lecroy et al., "Viewing Probe for High Voltage Pulses," Review of Scientific Instruments USA, Dec. 1960, 31(12):1354.
Lin et al., Principles and 10 Year Experience of the Beam Monitor System at the PSI Scanned Proton Therapy Facility, Center for Proton Radiation Therapy, Paul Scherrer Institute, CH-5232, Villigen PSI, Switzerland, 2007, 21 pages.
Linfoot et al., Acromegaly, in Hormonal Proteins and Peptides, edited by C.H. Li, 1975, pp. 191-246.
Literature Author and Keyword Search, Feb. 14, 2005, 44 pages.
Literature Keyword Search, Jan. 24, 2005, 98 pages.
Literature Search and Keyword Search for Synchrocyclotron, Jan. 25, 2005, 68 pages.
Literature Search by Company Name/Component Source, Jan. 24, 2005, 111 pages.
Literature Search, Jan. 26, 2005, 37 pages.
Livingston, M.S., et al. A Capillary Ion Source for the Cyclotron, Review Science Instruments, vol. 10, p. 9. 63-67, (1939).
LLNL, UC Davis Team Up to Fight Cancer, Lawrence Livermore National Laboratory, Apr. 28, 2006, SF-06-04-02, Livermore, California, pp. 1-4.
Lorin, Stefan, et al., "Development of a compact proton scanning system in Uppsala with a moveable second magnet", Phys. Med. Biol. 45, pp. 1151-1163, 2000 (13 pages).
Mandrillon, High Energy Medical Accelerators, EPAC 90, 2nd European Particle Accelerator Conference, Jun. 12-16, 1990, 2:54-58.
Marchand et al., IBA Proton Pencil Beam Scanning: an Innovative Solution for Cancer Treatment, Proceedings of EPAC 2000, Vienna, Austria, 3 pages.
Marti et al., High Intensity Operation of a Superconducting Cyclotron, Proceedings of the I 4the International Conference, Cyclotrons and Their Applications, Oct. 1995, pp. 45-48 (Oct. 1995).

Martin, Operational Experience with Superconducting Synchrotron Magnets Proceedings of the 1987 IEEE Particle Accelerator Conference, Mar. 16-19, 1987, vol. 3 of 3: 1379-1382.
Meote et al., ETOILE Hadrontherapy Project, Review of Design Studies Proceedings of EPAC 2002, 2002, pp. 2745-2747.
Miyamoto et al., Development of the Proton Therapy System, The Hitachi Hyoron, 79(10):775-775 779 (1997) [Lang: Japanese], English abstract (http://www.hitachi.com/rev/1998/revfeb98/rev4 706.htm).
Montelius et al., The Narrow Proton Beam Therapy Unit at the Svedberg Laboratory in Uppsala, ACTA Oncologica, 1991, 30:739-745
Moser et al., Nonlinear Beam Optics with Real Fields in Compact Storage Rings, Nuclear Instruments & Methods in Physics Research/Section B, 830, Feb. 1988, No. 1, pp. 105-109
Moyers et al., A Continuously Variable Thickness Scatterer for Proton Beams Using Self-compensating Dual Linear Wedges Loma Linda University Medical Center, Dept. of Radiation Medicine, Loma Linda, CA, Nov. 2, 1992, 21 pages.
National Cancer Institute Funding (Senate-Sep. 21, I 992) (www.tbomas.ioc.gov/cgibin/querw/z?rl02:S21SE2-712 (2 pages).
Nicholson, Applications of Proton Beam Therapy, Journal of the American Society of Radiologic Technologists, May/Jun. 1996, 67(5): 439-441.
Nolen et al., The Integrated Cryogenic - Superconducting Beam Transport System Planned for MSU, Proceedings of the J21h International Conference on High-Energy Accelerators, Aug. 1983, pp. 549-551.
Norimine et al., A Design of a Rotating Gantry with Easy Steering for Proton Therapy, Proceedings of EPAC 2002, 2002, pp. 2751-2753.
Ogino, Takashi, Heavy Charged Particle Radiotherapy-Proton Beam, Division of Radiation Oncology, National Cancer Hospital East, Kashiwa, Japan, Dec. 2003, 7 pages.
Okumura et al., Overview and Future Prospect of Proton Radiotherapy, Japanese Journal of Cancer Clinics, 1997, 43(2):209-214 [Lang .: Japanese].
Okumura et al., Proton Radiotherapy Japanese Journal of Cancer and Chemotherapy, 1993, 10. 20(14):2149-2155[Lang.: Japanese].
Outstanding from Search Reports, Accelerator of Polarized Portons at Fermilab, 2005, 20 pages.
Paganetti et al., Proton Beam Radiotherapy—The State of the Art, Springer Verlag, Heidelberg, ISBN 3-540-00321-5, Oct. 2005,36 pages.
Palmer and Tollestrup, Superconducting Magnet Technology for Accelerators, Annual Review of Nuclear and Particle Science, 1984, vol. 34, pp. 247-284.
Patent Assignee and Keyword Searches for Synchrocyclotron, Jan. 25, 2005, 76 pages.
Patent Assignee Search Paul Scherrer Institute, Library Services at Fish & Richardson P.C., Mar. 20, 2007, 40 pages.
Patent Prior Art Search for 'Proton Therapy System', Library Services at Fish & Richardson P.C., Mar. 20, 2007, 46 pages.
Pavlovic, Bear-optics study of the gantry beam delivery system for light-ion cancer therapy, Nuclear Instruments and Methods in Physics Research, Section A, Nov. 1997, 399(2):439-454(16).
Pedroni and Enge, Beam optics design of compact gantry for proton therapy Medical & Biological Engineering & Computing, May 1995, 33(3):271-277.
Pedroni and Jermann, "SGSMP: Bulletin Mar. 2002 Proscan Project, Progress Report on the PROSCAN Project of PSI" [online] retrieved from www.sgsmp.ch/protA23.htm, Mar. 2002, 5 pages.
Pedroni et al., A Novel Gantry for Proton Therapy at the Paul Scherrer Institute, Cycloctrons and Their Applications 2001: Sixteenth International Conference. AIP Conference Proceedings, 2001. 600:13-17.
Pedroni et al., The 200-MeV proton therapy project at the Paul Scherrer Institute: Conceptual design and practical realization, Medical Physics, Jan. 1995, 22(1 ):37-53.
Pedroni, Accelerators for Charged Particle Therapy: Performance Criteria from the User Point of View, Cyclotrons and their Applications, Proceedings of the 13th International Conference, Jul. 6-10, 1992, pp. 226-233.

(56) References Cited

OTHER PUBLICATIONS

Pedroni, E. and Jermann, M. "SGSMP: Bulletin Mar. 2002 Proscan Project, Progress Report on the PROSCAN Project of PSI," [online] retrieved from www.sgsmp.ch/protA23.htm, (5 pages) Mar. 2002.
Pedroni, Latest Developments in Proton Therapy Proceedings of EPAC 2000, pp. 240-244, 2000
Pedroni, Status of Proton Therapy: results and future trends, Paul Scherrer Institute, Division of Radiation Medicine. 1994. 5 pages.
Peggs et al., A Survey of Hadron Therapy Accelerator Technologies, Particle Accelerator Conference, Jun. 25-29, 2008, 7 pages.
Potts et al., MPWP6-Therapy III: Treatment Aids and Techniques Medical Physics, Sep/Oct. 1988, 15(5):798.
Pourrahimi et al., Powder Metallurgy Processed Nb3Sn(Ta) Wire for High Field NMR magnets, IEEE Transactions on Applied Superconductivity, Jun. 1995, 5(2):1603-1606.
Prieels et al., The IBA State-of-the-Art Proton Therapy System, Performances and Recent Results, Application of Accelerators in Research and industry—Sixteenth Int'l. Conj, American Institute of Physics, Nov. 1-5, 2000, 576:857-860.
Rabin et al., Compact Designs for Comprehensive Proton Beam Clinical Facilities, Nuclear Instruments & Methods in Physics Research, Apr. 1989, Section B, vol. 40-41, Part II, pp. 1335-1339.
Research & Development Magazine, Proton Therapy Center Nearing Completion, Aug. 1999, 41(9):2 pages (www.rdmag.com).
Resmini,, Design Characteristics of the K=800 Superconducting Cyclotron at M.S.U., Cyclotron Laboratory, Michigan State University, East Lansing, Michigan 48824, IEEE Transaction on Nuclear Science, vol. NS-26, No. 2, Apr. 1979, 8 pages.
RetroSearch Berkeley 88-Inch Cyclotron 'RF' or 'Frequency Control', Jan. 21, 2005, 36 pages.
RetroSearch Berkeley 88-Inch Cyclotron, Jan. 24, 2005, 170 pages.
RetroSearch Bernard Gottschalk, Cyclotron, Beams, Compensated Upstream Modulator, Compensated Scatter, Jan. 21, 2005, 20 pages.
RetroSearch Cyclotron with 'RF' or 'Frequency Control', Jan. 21, 2005, 49 pages.
RetroSearch Gottschalk, Bernard, Harvard Cyclotron Wheel, Jan. 21, 2005, 20 pages.
RetroSearch Loma Linda University Beam Compensation, Jan. 21, 2005, 60 pages.
RetroSearch Loma Linda University, Beam Compensation Foil Wedge, Jan. 21, 2005, 15 pages.
Revised Patent Keyword Search, Jan. 25, 2005, 86 pages.
Rifuggiato et, al., Status Report of the LNS Superconducting Cyclotron Nukleonika, 2003, 48:SI31-Si34, Supplement 2.
Rode, Tevatron Cryogenic System, Proceedings of the 12th International Conference on Highenergy Accelerators, Fermilab, Aug. 11-16, 1983, pp. 529-535.
Salzburger et al., Superconducting Synchrotron Magnets Supraleitende Synchrotronmagnete, NTIS, 155 pages (Oct. 1975).
Schillo et al,. Compact Superconducting 250 MeV Proton Cyclotron for the PSI Proscan Proton Therapy Project, Cyclotrons and Their Applications 2001, Sixteenth International Conference, 2001, pp. 37-39.
Schneider et al., Nevis Synchrocyclotron Conversion Program—RF System, IEEE Transactions on Nuclear Science USA, Jun. 1969, ns 16(3): 430-433.
Schneider et al., Superconducting Cyclotrons, IEEE Transactions on Magnetics, vol. MAG-11, No. 2, Mar. 1975, New York, pp. 443-446.
Schreuder et al., The Non-orthogonal Fixed Beam Arrangement for the Second Proton Therapy Facility at the National Accelerator Centre, Application of Accelerators in Research and Industry, American Institute of Physics, Proceedings of the Fifteenth International Conference, Nov. 1998, Part Two, pp. 963-966.
Schreuder, Recent Developments in Superconducting Cyclotrons, Proceedings of the 1995 Particle Accelerator Conference, May 1-5, 1995, vol. 1, pp. 317-321.
Schubert and Blosser, Conceptual Design of a High Field Ultra-Compact Cyclotron for Nuclear Physics Research, Proceedings of the 1997 Particle Accelerator Conference, May 12-16, 1997, vol. 1, 3 pp. 1060-1062.
Schubert, Extending the Feasibility Boundary of the Isochronous Cyclotron, Dissertation submitted to Michigan State University, 1997, Abstract http://adsabs.harvard.edu/abs/1998PhDT . . . 147S.
Shelaev et al., Design Features of a Model Superconducting Synchrotron of JINR, Proceedings of the 12th International Conference on High-energy Accelerators, Aug. 11-16, 1983, pp. 416-418.
Shintomi et. al., Technology and Materials for the Superconducting Super Collider (SSC) Project, [Lang.: Japanese], The Iron and Steel Institute of Japan 00211575, 78(8): 1305-1313, 1992, http://ci.nil.ac.jp/naid/I I 0001493249/en/.
Shintomi et. al., Technology and Materials for the Superconducting Super Collider (SSC) Project, The Iron and Steel Institute of Japan 00211575, 78(8): 1305-1313, 1992, [English Abstract included].
Sisterson, Clinical use of proton and ion beams from a world-wide perspective, Nuclear Instruments and Methods in Physics Research, Section B, 1989, 40-41:1350-1353.
Slater et al., Developing a Clinical Proton Accelerator Facility: Consortium-Assisted Technology Transfer, Conference Record of the 1991 IEEE Particle Accelerator Conference: Accelerator Science and Technology, voi. I, May 6-9, 1991, pp. 532-536.
Smith et al., The Northeast Proton Therapy Center at Massachusetts General Hospital Journal of Brachytherapy International, Jan. 1997, pp. 137-139.
Snyder and Marti, Central region design studies for a proposed 250 MeV proton cyclotren, Nuclear Instruments and Methods in Physics Research, Section A, 1995, vol. 355, pp. 618-623.
Soga, Progress of Particle Therapy in Japan, Application of Accelerators in Research and Industry, American Institute of Physics, Sixteenth International Conference, Nov. 2000, pp. 869-872.
Source Search "Cites of U.S. and Foreign Patents/Published applications in the name of Mitsubishi Denki Kabushiki Kaisha and Containing the Keywords (Proton and Synchrocyclotron)," Jan. 2005, 8 pages.
Spiller et al., The GSI Synchrotron Facility Proposal for Acceleration of High Intensity Ion and Proton Beams Proceedings of the 2003 Particle Accelerator Conference, May 12-16, 2003, vol. 1, pp. 589-591.
Stanford et al., Method of Temperature Control in Microwave Ferroelectric Measurements, Sperry Microwave Electronics Company, Clearwater, Florida, Sep. 19, 1960, 1 page.
Superconducting Cyclotron Contract awarded by Paul Scherrer Institute (PSI), Villigen, Switzerland, http://www.accel.de/News/superconducting_ cyclotron_ contract.htm, Jan. 2009, 1 page.
Tadashi et al., Large superconducting super collider (SSC) in the planning and materials technology,78(8):1305-1313, The Iron and Steel Institute of Japan 00211575, Aug. 1992.
Takada, Conceptual Design of a Proton Rotating Gantry for Cancer Therapy, Japanese Journal of Medical Physics, 1995, 15(4):270-284.
Takayama et al., Compact Cyclotron for Proton Therapy, Proceedings of the 81h Symposium on Accelerator Science and Technology, Japan, Nov. 25-27, 1991, pp. 380-382.
Teng, The Fermilab Tevatron, Coral Gables 1981, Proceedings, Gauge Theories, Massive Neutrinos, and Proton Decay, 1981, pp. 43-62.
The Davis 76-Inch Isochronous Cyclotron, Beam On; Crocker Nuclear Laboratory, University of California, 2009, 1 page.
The Journal of Practical Pharmacy, 1995, 46(1):97-103 [English Abstract included].
The Journal of Practical Pharmacy, 1995, 46(1):97-103 [Japanese].
The K100 Neutron-therapy Cyclotron, National Superconducting Cyclotron Laboratory at Michigan State University (NSCL ), retrieved from: http://www.nscl.msu.edu/tech/accelerators/kl 00, Feb. 2005, 1 page.
The K250 Proton therapy Cyclotron, National Superconducting Cyclotron Laboratory at Michigan State University (NSCL), retrieved from: http://www.nscl.msu.edu/tech/accelerators/k.250.html, Feb. 2005, 2 pages.

(56) References Cited

OTHER PUBLICATIONS

The K250 Proton-therapy Cyclotron Photo Illustration, National Superconducting Cyclotron Laboratory at Michigan State University (NSCL), retrieved from: http://www.nscl.msu.edu/media/image/ experimental-equipment-technology /25 0 .html, Feb. 2005, 1 page.
Tilly, et al., "Development and verification of the pulsed scanned proton beam at The Svedberg 254 Laboratory in Uppsala", Physics in Medicine and Biology, Phys. Med. Biol. 52, pp. 2741-2454, 2007.
Tobias, C.A., et al., Pituitary Irradiation with High-Energy Proton Beams a Preliminary Report, Cancer Research, vol. 18, No. 2. pp. 121-134 (1958).
Tom, The Use of Compact Cyclotrons for Producing Fast Neutrons for Therapy in a Rotatable Isocentric Gantry, IEEE Transaction on Nuclear Science, Apr. 1979, 26(2):2294-2298.
Toyoda, Proton Therapy System, Sumitomo Heavy Industries, Ltd. 2000, 5 pages.
Trinks et. al., The Tritron: A Superconducting Separated-Orbit Cyclotron, Nuclear Instruments and Methods in Physics Research, Section A, 1986, vol. 244, pp. 273-282.
Tsuji, The Future and Progress of Proton Beam Radiotherapy, Journal of Japanese Society for Therapeutic Radiology and Oncology, 1994, 6(2):63-76.
U.S. Appl. No. 13/830,792, filed Mar. 14, 2013, including the USPTO electronic file for U.S. Appl. No. 13/830,792.
U.S. Appl. No. 13/949,459, filed Jul. 24, 2013, including the USPTO electronic file for U.S. Appl. No. 13/949,459.
U.S. Appl. No. 61/676,377, filed Jul. 27, 2012, including the USPTO electronic file for U.S. Appl. No. 61/676,377.
UC Davis School of Medicine, Unlikely Partners Turn Military Defense into Cancer Offense, Current Issue Summer 2008. Sacramento, California, pp. 1-2.
Umegaki et al., Development of an Advanced Proton Beam Therapy System for Cancer Treatment Hitachi Hyoron, 2003, 85(9):605-608 [Lang.: Japanese], English abstract, http://www.hitachi.com/ICSFiles/afieldfile/2004/06/0 I/r2003 _ 04_I 04.pdf or http://www.hitachi.com/rev/archive/2003/2005649_12606.html (full text) [Hitachi, 52(4), Dec. 2003].
Umezawa et al., Beam Commissioning of the new Proton Therapy System for University of Tsukuba, Proceedings of the 2001 Particle Accelerator Conference, vol. 1, Jun. 18-22, 2001, pp. 648-650.
Van Steenbergen, Superconducting Synchroton Development at BNL, Proceedings of the 8th International Conference on High-Energy Accelerators CERN 1971, 1971, pp. 196-198.
Van Steenbergen, The CMS, a Cold Magnet Synchrotron to Upgrade the Proton Energy Range of the BNL Facility, IEEE Transactions on Nuclear Science, Jun. 1971, 18(3):694-698.
Vandeplassche et al., 235 MeV Cyclotron for MGH's Northeast Proton Therapy Center (NPTC): Present Status, EPAC 96, Fifth European Partical Accelerator Conference, vol. 3, Jun. 10-14, 1996, pp. 2650-2852.
Vorobiev et al., Concepts of a Compact Achromatic Proton Gantry with a Wide Scanning Field, Nuclear Instruments and Methods in Physics Research, Section A., 1998, 406(2):307-310.
Vrenken et al., A Design of a Compact Gantry for Proton Therapy with 20-Scanning, Nuclear Instruments and Methods in Physics Research, Section A, 1999, 426(2):618-624
Wikipedia, Cyclotron http://en.wikipedia.om/wiki/Cyclotron (originally visited Oct. 6, 2005, Revisited Jan. 28, 2009), 7 pages.
Wikipedia, Synchrotron http://en.wikipedia.org/wiki/Synchrotron (originally visited Oct. 6, 2005, revisited Jan. 28, 2009), 7 pages.
Worldwide Patent Assignee Search, Jan. 24, 2005, 224 pages.
Worldwide Patent Keyword Search, Jan. 24, 2005, 94 pages.
Wu, Conceptual Design and Orbit Dynamics in a 250 MeV Superconducting Synchrocyclotron, Ph.D. Dissertation, Michigan State University, Department of Physics and Astronomy, 1990, 172 pages.
York et al., Present Status and Future Possibilities at NSCL-MSU, EP AC 94, Fourth European Particle Accelerator Conference, pp. 554-556, Jun. 1994.
York et al., The NSCL Coupled Cyclotron Project—Overview and Status, Proceedings of the Fifteenth International Conference on Cyclotrons and their Applications, Jun. 1998, pp. 687-691.
Yudelev et al., Hospital Based Superconducting Cyclotron for Neutron Therapy: Medical Physics Perspective, Cyclotrons and their applications 2001, 16th International Conference. American Institute of Physics Conference Proceedings, vol. 600, May 13-17, 2001, pp. 40-43.
Zherbin et al., Proton Beam Therapy at the Leningrad Synchrocyclotron (Clinicomethodological Aspects and Therapeutic Results), Aug. 1987, 32(8):17-22, (German with English abstract on pp. 21-22).
International Preliminary Report on Patentability for International Patent Application No. PCTUS2020/021343, Issued Sep. 23, 2021, (11 Pages).
Non-Final Office Action for U.S. Appl. No. 16/811,130, Issued Mar. 4, 2021, (27 Pages.).
Written Opinion for International Patent Application No. PCTUS2020/021343. Issued Jul. 8, 2020, (11 Pages).
International Search Report for International Patent Application No. PCTUS2020/021343. Issued Jul. 8, 2020, (7 Pages).
Written Opinion for International Patent Application No. PCT/US2020/021342. Issued Jul. 6, 2020, (12 Pages.).
International Search Report for International Patent Application No. PCT/US2020/021342. Issued Jul. 6, 2020, (8 Pages).
Notice of Reasons for Rejection for Japanese Patent Application No. 2021-553096, mailed Oct. 11, 2022, (with English translation), (18 pages).
Notice of Reasons for Rejection for Japanese Patent Application No. 2021-553099, mailed Oct. 11, 2022, (with English translation), (12 pages).
Non-Final Office Action for United States U.S. Appl. No. 17/712,313, mailed Dec. 9, 2022, (5 pages).
Notice of Reasons for Refusal in Japanese Application No. 2021-553096 dated May 1, 2023 [w/English translation], 7 pages.
Communication pursuant to Rules 161(1) & 162 EPC for EP Application No. 20717368.3 dated Oct. 19, 2021, 3 pages.
Boyer, A et al., "Basic Applications of Multi-leaf Collimators: Report of Task Group No. 50—Radiation Therapy Committee," AAPM Report No. 72, American Association of Physicists in Medicine by Medical Physics Publishing, 62 pages (2001).
Bues et al., "Therapeutic Step and Shoot Proton Beam Spot-Scanning with a Multi-Leaf Collimator: A Monte Carlo Study," Radiation Protection Dosimetry, 115(1-4):164-169 (2005).
Favaudon et al., "Radiotherapie << flash>> a tres haut debit de dose: un moyen d'augmenter l'indice therapeutique par minimisation des dommages aux tissus sains?" Cancer / Radiotherapie, v. 19, pp. 526-531 (2015), 6 pages (English abstract included).
Hyer et al., "A dynamic collimation system for penumbra reduction in spot-scanning proton therapy: Proof of concept," Medical Physics, 41(9):091701-1-091701-9 (2014).
Non-Final Office Action in U.S. Appl. No. 18/231,439 dated Apr. 3, 2024, 7 pages.
Office Action in Chinese Application No. 202080034492.X dated Nov. 30, 2023, [with English translation], 26 pages.
Search Report in Taiwan Application No. 109107555 dated Dec. 8, 2023 [English translation], 1 page.
Office Action in Taiwan Application No. 109107555 dated Dec. 8, 2023 [with English summary], 19 pages.
Office Action in Chinese Application No. 202080034487.9 dated Nov. 13, 2023 [with English translation], 20 pages.
Search Report in Taiwan Application No. 109107560 dated Dec. 8, 2023 [English translation], 1 page.
Office Action in Taiwan Application No. 109107560 dated Dec. 8, 2023 [with English summary], 15 pages.
Communication pursuant to Article 94(3) EPC in Application No. 20717368.3 dated Feb. 8, 2024, 5 pages.
Notice of Allowance for related CN Application No. 202080034487.9 dated May 21, 2024 with English-language translation (7 pgs.).
Second Office Action for related CN Application No. 202080034492.X dated Jun. 12, 2024 with English-language translation (18 pgs.).
Office Action for related CN Application No. 109107555 dated May 9, 2024 with English-language translation (5 pgs.).

(56) References Cited

OTHER PUBLICATIONS

Office Action for related CN Application No. 109107560 dated May 9, 2024 with English-language translation (5 Pages).
Office Action for related JP Application No. 2023-056084 dated May 28, 2024 with English-language translation (18 pgs.).
International Preliminary Report on Patentability issued Aug. 25, 2021, for related International Application No. PCT/US2020/021342 (34 pgs.).
Office Action issued Dec. 8, 2023, for related TW Application No. 109107555 with English-language translated (20 pgs.).
Office Action issued May 9, 2024, for related TW Application No. 109107555 with English-language translation (5 pgs.).
Notice of Allowance issued Jul. 25, 2024, for related U.S. Appl. No. 18/231,439 (9 pgs.).

* cited by examiner

COLLIMATOR AND ENERGY DEGRADER FOR A PARTICLE THERAPY SYSTEM

CROSS-REFERENCE TO RELATED APPLICATIONS

This application is a continuation of U.S. patent application Ser. No. 16/811,138 which was filed on Mar. 6, 2020, and which is titled "Collimator And Energy Degrader For A Particle Therapy System". U.S. patent application Ser. No. 16/811,138 is incorporated herein by reference. U.S. patent application Ser. No. 16/811,138 and, therefore this application, claims priority to, and the benefit of, U.S. Provisional Patent Application No. 62/815,721, which was filed Mar. 8, 2019, and which is titled "Delivery Of Radiation By Column". U.S. patent application Ser. No. 16/811,138 and, therefore this application, claims priority to, and the benefit, of U.S. Provisional Patent Application No. 62/853,387, which was filed on May 28, 2019, and which is titled "Energy Degrader Including Boron Carbide". U.S. patent application Ser. No. 16/811,138 and therefore this application, claims priority to, and the benefit, of U.S. Provisional Patent Application No. 62/889,825, which was filed on Aug. 21, 2019, and which is titled "Generating A Treatment Plan". U.S. patent application Ser. No. 16/811,138 and therefore this application, claims priority to, and the benefit, of U.S. Provisional Patent Application No. 62/889,861, which was filed on Aug. 21, 2019, and which is titled "Collimator For A Particle Therapy System". The contents of U.S. Provisional Patent Applications Nos. 62/815,721, 62/853,387, 62/889,825, and 62/889,861 are incorporated herein by reference.

TECHNICAL FIELD

This disclosure relates generally to a collimator and to an energy degrader for a particle therapy system.

BACKGROUND

Particle therapy systems use an accelerator to generate a particle beam for treating afflictions, such as tumors. In operation, particles are accelerated in orbits inside a cavity in the presence of a magnetic field and are removed from the cavity through an extraction channel. A magnetic field regenerator generates a magnetic field bump near the outside of the cavity to distort the pitch and angle of some orbits so that they move towards, and eventually into, the extraction channel. A beam, comprised of the particles, exits the extraction channel.

A scanning system is down-beam of the extraction channel. In this example, down-beam suggests closer to an irradiation target relative to the extraction channel. The scanning system moves the particle beam relative to the irradiation target to expose various parts of the irradiation target to the particle beam. For example, to treat a tumor, the particle beam may be scanned over different parts of the tumor to expose the different parts to radiation.

The scanning system may include an energy degrader to change an energy of the particle beam and therefore different depths of the tumor that the particle beam impacts. A collimator may be used to trim the particle beam. For example, the collimator may allow part of the particle beam to reach the patient while preventing a different part of the particle beam from reaching the patient.

SUMMARY

An example system includes a particle accelerator to produce a particle beam to treat a patient and a carrier having openings including a first opening and a second opening. The carrier includes a material that inhibits transmission of the particle beam and the carrier is located between the particle accelerator and the patient. A control system is configured to control movement of the particle beam to the first opening to enable at least part of the particle beam to reach the patient, to change an energy of the particle beam while the particle beam remains stationary at the first opening, and to control movement of the particle beam from the first opening to the second opening. The example system may include one or more of the following features, either alone or in combination.

The openings may include an array of holes, with the first opening being a first hole and the second opening being a second hole. The openings may include an array of slots, with the first opening being a first slot and the second opening being a second slot.

The system may include an energy degrader between the particle accelerator and the patient. The energy degrader may include structures configured to move into and out of path of the particle beam in order to change an energy of the particle beam. The control system may be configured to control movements of the structures into or out of a path of the particle beam to change the energy of the particle beam. The structures may include plates for changing the energy of the particle beam as the particle beam passes through one or more of the plates. The plates may be or include boron carbide. The particle accelerator may include a superconducting magnet having conductive coils. The control system may be configured to change a current through the conductive coils to change the energy of the particle beam.

The control system may be configured to change the energy of the particle beam so that the particle beam treats, through the first opening, a columnar portion of a target in the patient before the particle beam moves from the first opening to the second opening. While the particle beam is at the first opening, the particle beam may deliver a dose of radiation to the target that exceeds one Gray-per-second for a duration of less than five seconds. While the particle beam is at the first opening, the particle beam may deliver a dose of radiation to the target that is between 20 Gray-per-second and 100 Gray-per-second for a duration that is between 10 milliseconds and 5 seconds. While the particle beam is at the first opening, the particle beam may deliver a dose of radiation to the target that is between 40 Gray-per-second and 120 Gray-per-second for a duration of less than 5 seconds. While the particle beam is at the first opening, the particle beam may deliver a dose of radiation to the target at any ultra-high dose rate. While the particle beam is at the first opening, the particle beam may deliver, for a duration of less than 500 ms, for a duration that is between 10 ms and 5 s, or for a duration that is less than 5 s, a dose of radiation to the target that is greater than 100 Gray-per-second, that is greater than 200 Gray-per-second, that is greater than 300 Gray-per-second, that is greater than 400 Gray-per-second, or that is greater than 500 Gray-per-second.

The openings may include holes, with the first opening being a first hole and the second opening being a second hole. Controlling movement of the particle beam to the first hole and then to the second hole may include centering the particle beam at first hole then centering the particle beam at the second hole.

Following movement of the particle beam from the first opening to the second opening, the particle beam may never again move to the first opening.

The system may include a scanning magnet having conductive coils. The scanning magnet may be for generating a magnetic field to affect the movement of the particle beam. The control system may be configured to control movement of the particle beam by changing a current through the conductive coils of the scanning magnet to affect the magnetic field. The system may include a track on which the carrier is mounted for movement within a beam field of the particle beam. A motor may be configured to move the carrier along the track. The control system may be configured to control the motor to move the carrier along the track based on movement of the particle beam. The system may include a ridge filter to spread-out a Bragg peak of the particle beam.

The system may include a track on which the carrier is mounted for movement. A motor may be configured to move the carrier along the track in response to one or more commands from the control system. The control system may be configured to change an energy of the particle beam while the particle beam remains stationary at the second opening, and to control movement of the particle beam from the second opening to multiple additional openings, with the particle beam remaining stationary for a period of time at each of the multiple additional openings while the energy of the particle beam changes at each opening.

An example collimator includes a carrier having one or more openings. The carrier may be or include a material that inhibits transmission of a particle beam. Each of the one or more openings may have a size and a shape that are not changeable. Each of the one or more openings may have a size and/or a shape that are changeable. Some of the one or more openings may have a size and/or a shape that are changeable and some of the one or more openings may have a size and/or a shape that are not changeable. The collimator may include track on which the carrier is mounted for movement within a beam field of the particle beam. A motor is configured to move the carrier along the track based on movement of the particle beam. The example collimator may include one or more of the following features, either alone or in combination.

The one or more openings may be or include an array of holes. The one or more openings may be or include a single linear array of holes. The one or more openings may be or include one or more slots extending across a longitudinal dimension of the carrier. The one or more openings may be or include a single slot extending across a longitudinal dimension of the carrier. The carrier may be made of or include at least one of nickel, brass, or tungsten. The motor may be responsive to commands from a control system to move the carrier along the track.

The carrier may be a first carrier. The collimator may include a second carrier having an array of openings. The second carrier may be or include a material that inhibits transmission of a particle beam. The second carrier may be mounted for movement within the beam field of the particle beam. The motor may be configured also to move the second carrier along the track based on movement of the particle beam. The first carrier and the second carrier may be connected to each other physically. The first carrier and the second carrier may be configured for independent movement relative to each other. For example, the motor may be a first motor, and the collimator may also include a second motor configured to move the second carrier. The second motor may be configured to move the second carrier based on the movement of the particle beam.

An example system includes a particle accelerator to produce a particle beam to treat a patient and a carrier having an opening. The carrier may be or include a material that inhibits transmission of the particle beam. The carrier may be located between the particle accelerator and the patient. The system may include a control system to control movement of the particle beam to a first part of the opening to enable at least part of the particle beam to reach the patient, to change an energy of the particle beam while the particle beam remains stationary at the first part of the opening, and to control movement of the particle beam from the first part of the opening to a second part of the opening. The example system may include one or more of the following features, either alone or in combination.

The opening may be or include a slot that extends along the carrier. The control system may be configured to change an energy of the particle beam while the particle beam remains stationary at the second part of the opening, and to control movement of the particle beam from the second part of the opening to multiple additional parts of the opening, with the particle beam remaining stationary for a period of time at each of the multiple additional parts of the opening while the energy of the particle beam changes at each part of the opening.

The control system may be configured to change the energy of the particle beam so that the particle beam treats, through the first part of the opening, a columnar portion of a target in the patient before the particle beam moves from the first part of the opening to the second part of the opening. While the particle beam is at the first part of the opening, the particle beam may deliver a dose of radiation to the target that exceeds one Gray-per-second for a duration of less than five seconds. While the particle beam is at the first part of the opening, the particle beam may deliver a dose of radiation to the target that is between 20 Gray-per-second and 100 Gray-per-second for a duration that is between 10 milliseconds and 5 seconds. While the particle beam is at the first part of the opening, the particle beam may deliver a dose of radiation to the target that is between 40 Gray-per-second and 120 Gray-per-second for a duration of less than 5 seconds. While the particle beam is at the first part of the opening, the particle beam may deliver a dose of radiation to the target at an ultra-high dose rate.

The system may include an energy degrader between the particle accelerator and the patient. The energy degrader may include structures configured to move into and out of path of the particle beam in order to change an energy of the particle beam. The control system may be configured to control movements of the structures into or out of a path of the particle beam to change the energy of the particle beam. The structures may be or include plates for changing the energy of the particle beam as the particle beam passes through one or more plates. The one or more plates or structures may include boron carbide.

The particle accelerator may include a superconducting magnet comprising conductive coils. The control system may be configured to change a current through the conductive coils to change the energy of the particle beam.

The system may include a track on which the carrier is mounted for movement within a beam field of the particle beam. A motor may be configured to move the carrier along the track.

An example system includes a particle accelerator to provide a particle beam to treat a patient located in a treatment room. The system includes an energy degrader that includes multiple structures. Each structure of the multiple structures is for changing an energy of the particle beam as the particle beam passes through the structure. Each structure includes boron carbide. The system also includes actuators, each for controlling movement of a corresponding one of the multiple structures into or out of a path of the particle beam. The energy degrader is located in the treatment room. The system may include one or more of the following features, either alone or in combination.

Each structure may be a plate. Each structure may be a polyhedron. Each structure may be pure boron carbide. One or more of the multiple structures may include a composite material comprised of boron carbide and graphite.

The energy degrader may be located no more than three meters from the patient along a beam line of the particle beam. The energy degrader may be located no more than two meters from the patient along a beam line of the particle beam. The energy degrader may be located no more than one meter from the patient along a beam line of the particle beam. The system may include a scanning magnet to move the particle beam relative to the patient. The energy degrader may be located between the scanning magnet and the patient.

The particle beam may be applied to the patient at an ultra-high dose rate. The particle beam may be applied to the patient at a dose rate that exceeds 1 Gray-per-second for a duration of less than 5 seconds. The particle beam may be applied to the patient at a dose rate that is between 20 Gray-per-second and 100 Gray-per-second for a duration that is between 10 milliseconds and 5 seconds. The particle beam may be applied to the patient at a dose rate that is between 40 Gray-per-second and 120 Gray-per-second for a duration of less than 5 seconds.

The structures of the energy degrader may be controllable to move into or out of the particle beam while the particle beam remains stationary in order to treat a column of tissue within the patient using an ultra-high dose rate. The actuators may be linear motors or any other appropriate type of motors.

An example system includes a particle accelerator to provide a particle beam to treat a patient located in a treatment room. The system includes an energy degrader that includes multiple structures. Each structure of the multiple structures is for changing an energy of the particle beam as the particle beam passes through the structure. Each structure includes boron carbide. The system also includes actuators, each for controlling movement of a corresponding one of the multiple structures into or out of a path of the particle beam. The energy degrader is located no more than four meters from the patient along a beam line of the particle beam. The system may include one or more of the following features, either alone or in combination.

The structures may be controllable to move into or out of the particle beam while the particle beam remains stationary in order to treat a column of tissue within the patient using an ultra-high dose rate. The energy degrader may be located no more than three meters from the patient along a beam line of the particle beam. The energy degrader may be located no more than two meters from the patient along a beam line of the particle beam. The energy degrader may be located no more than one meter from the patient along a beam line of the particle beam.

The particle beam may be applied to the patient at an ultra-high dose rate. The particle beam may be applied to the patient at a dose rate that exceeds 1 Gray-per-second for a duration of less than 5 seconds. The particle beam may be applied to the patient at a dose rate that is between 20 Gray-per-second and 100 Gray-per-second for a duration that is between 10 milliseconds and 5 seconds. The particle beam may be applied to the patient at a dose rate that is between 40 Gray-per-second and 120 Gray-per-second for a duration of less than 5 seconds.

The structures of the energy degrader may be controllable to move into or out of the particle beam while the particle beam remains stationary in order to treat a column of tissue within the patient using an ultra-high dose rate. The actuators may be linear motors or other types of motors. One or more of the multiple structures may include a composite material comprised of boron carbide and graphite.

An example system includes a particle accelerator to provide a particle beam to treat a patient located in a treatment room, a scanning magnet to move the particle beam relative to the patient, and an energy degrader. The energy degrader includes multiple structures. Each structure of the multiple structures is for changing an energy of the particle beam as the particle beam passes through the structure. Each structure includes boron carbide. The system also includes actuators, each for controlling movement of a corresponding one of the multiple structures into or out of a path of the particle beam. The energy degrader is located between the scanning magnet and the patient. The system may include one or more of the following features, either alone or in combination.

The energy degrader may be located no more than one meter from the patient along a beam line of the particle beam. The particle beam may be applied to the patient at an ultra-high dose rate. The particle beam may be applied to the patient at a dose rate that exceeds 1 Gray-per-second for a duration of less than 5 seconds. The particle beam may be applied to the patient at a dose rate that is between 20 Gray-per-second and 100 Gray-per-second for a duration that is between 10 milliseconds and 5 seconds. The particle beam may be applied to the patient at a dose rate that is between 40 Gray-per-second and 120 Gray-per-second for a duration of less than 5 seconds. The structures of the energy degrader may be controllable to move into or out of the particle beam while the particle beam remains stationary in order to treat a column of tissue within the patient at an ultra-high dose rate of radiation.

The system may include an outer gantry on which the particle accelerator is mounted. The outer gantry may be controllable to move the particle accelerator at least partway around the patient. The system may include an inner gantry that is controllable to move in concert with the outer gantry. The inner gantry may include a nozzle that is extendible towards, and retractable away from, the patient. The energy degrader may be located in the nozzle. The energy degrader is located in a treatment room in which the particle beam is applied to the patient. The nozzle may be retractable fully into the inner gantry.

The particle beam may have a spot size of less than 1.2 centimeters (cm) sigma for a particle beam having an energy of 70 MeV or greater. The particle beam may have a spot size of less than 1.2 centimeters (cm) sigma. The particle beam may have a spot size of less than 0.5 centimeters (cm) sigma.

There may be no structures used to affect the particle beam between the energy degrader and the patient. The system may include a configurable collimator between the energy degrader and the patient. The configurable collimator may be controllable to trim the particle beam at a resolution as small as a single spot. The actuators may include linear motors. The actuators may include rotary motors that each drive a corresponding linear actuator to control movement of a corresponding structure.

One or more of the multiple structures in the energy degrader may include a composite material comprised of boron carbide and graphite. Each of the multiple structures in the energy degrader may be pure boron carbide.

Two or more of the features described in this disclosure, including those described in this summary section, may be combined to form implementations not specifically described herein.

Control of the various systems described herein, or portions thereof, may be implemented via a computer program product that includes instructions that are stored on one or more non-transitory machine-readable storage media and that are executable on one or more processing devices (e.g., microprocessor(s), application-specific integrated circuit(s), programmed logic such as field programmable gate array(s), or the like). The systems described herein, or portions thereof, may be implemented as an apparatus, method, or electronic system that may include one or more processing devices and computer memory to store executable instructions to implement control of the stated functions.

The details of one or more implementations are set forth in the accompanying drawings and the description below. Other features, objects, and advantages will be apparent from the description and drawings, and from the claims.

DESCRIPTION OF THE DRAWINGS

Like reference symbols in the various drawings indicate like elements.

DETAILED DESCRIPTION

Figure 1:
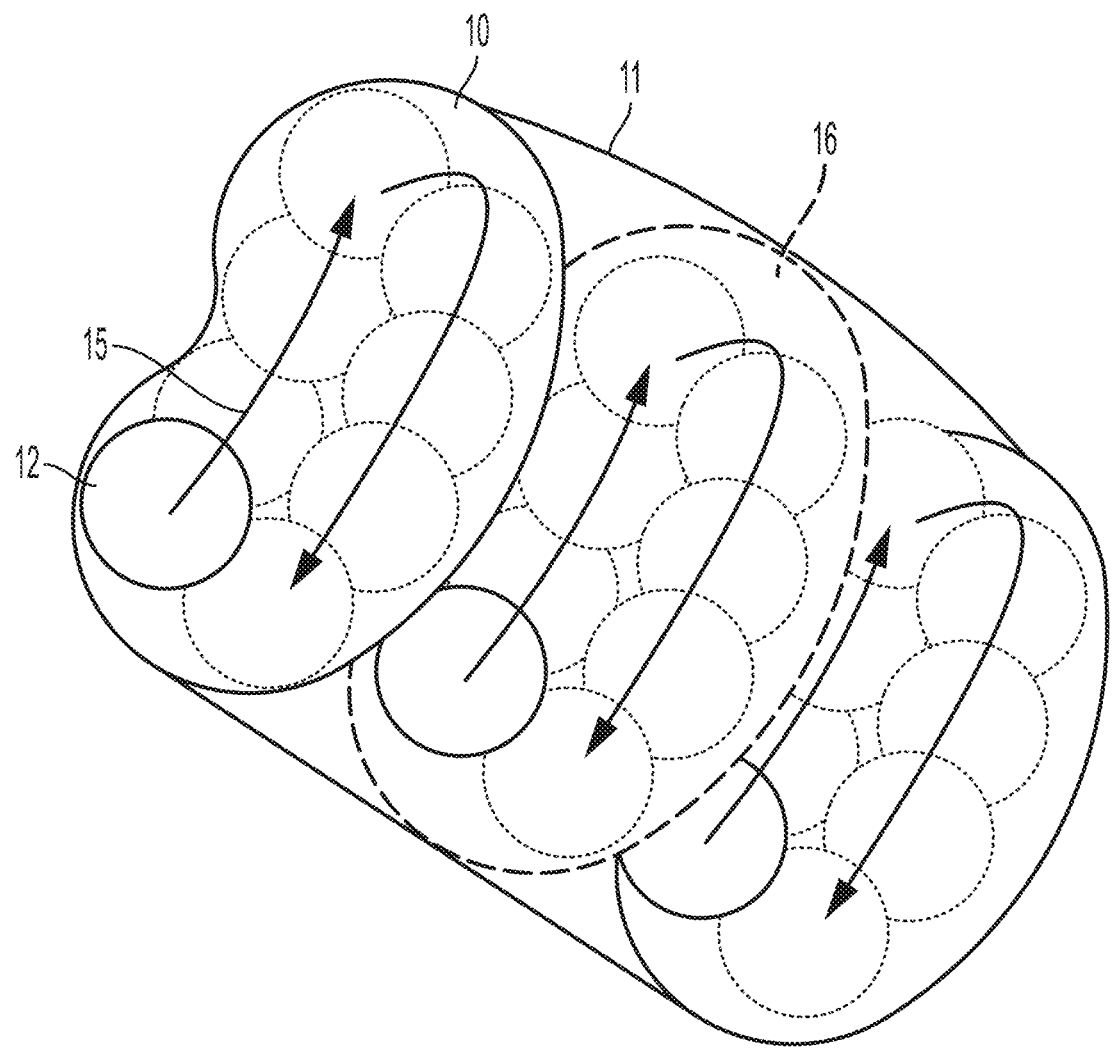
FIG. 1 is a perspective view of an example irradiation target treated by scanning a particle beam across entire layers sequentially.

Described herein are example implementations of particle therapy systems that include a collimator. The particle therapy systems are for treating an irradiation target ("target") in a patient, such as a tumor, using a particle beam such as a proton or ion beam. Some systems treat the target cross-sectional layer by layer. For example, the energy of the particle beam may be controlled to deliver a radiation dose ("dose") to a layer and then the particle beam may be moved across all or part of that layer. Thereafter, the energy of the particle beam may be changed to deliver dose to another layer. The particle beam may be moved across all or part of that other layer and so on until the entire target is treated. For example, FIG. 1 shows treating an entire layer 10 of a target 11 using a particle beam 12 having an energy sufficient to deliver dose to layer 10 by moving the particle beam across the layer along the directions of arrows 15. Then a different layer 16 of the target 11 is treated in the same manner using a particle beam having a different energy sufficient to deliver dose to layer 16, and so on. The treatment of the whole treatment volume on average is typically at relatively small dose rates, such as 0.1 Gray-per-second. The particle beam often penetrates healthy tissue before reaching the target. Any one location within this healthy tissue may be visited several times over the course of treatment. The dose at such a location is received over a time scale on the order of minutes.

By contrast, some particle therapy systems may treat three-dimensional columns of the target using ultra-high (FLASH) dose rates of radiation. These systems scale the ultra-high dose rate deliveries to targets using pencil beam scanning. In some examples, pencil beam scanning includes delivering a series of small beams of particle radiation that can each have a unique direction, energy, and charge. By combining doses from these individual beams, a three-dimensional target treatment volume may be treated with radiation. Furthermore, instead of organizing the treatment into layers at constant energies, the systems organize the treatment into columns defined by the direction of a stationary beam. The direction of the beam may be toward the surface of the target.

In some implementations, all or part of a column is treated before the particle beam is directed along another path through the irradiation target. In some implementations, a path through the target is all or part-way through the target. In an example, the particle beam may be directed along a path through a target and not deviate from that path. While directed along that path, the energy of the particle beam is changed. The particle beam does not move as its energy changes and, as a result, the particle beam treats all or a part of an interior portion of the target that extends along a length of the particle beam and along a width of the beam spot. The treatment is thus depth-wise along a longitudinal direction of the beam. For example, a portion of the target treated may extend from a spot of the beam at the surface of the target down through all or part of an interior of the target. The result is that the particle beam treats a three-dimensional columnar portion of the target using an ultra-high dose rate of radiation. In some examples, ultra-high dose rates of radiation include, for example, doses of radiation that exceed 1 Gray-per-second for a duration of less than 500 milliseconds (ms), that exceed 1 Gray-per-second for a duration of between 10 ms and 5 seconds (s), or that exceed 1 Gray-per-second for a duration of less than 5 s. Other examples are provided herein.

Figure 2:
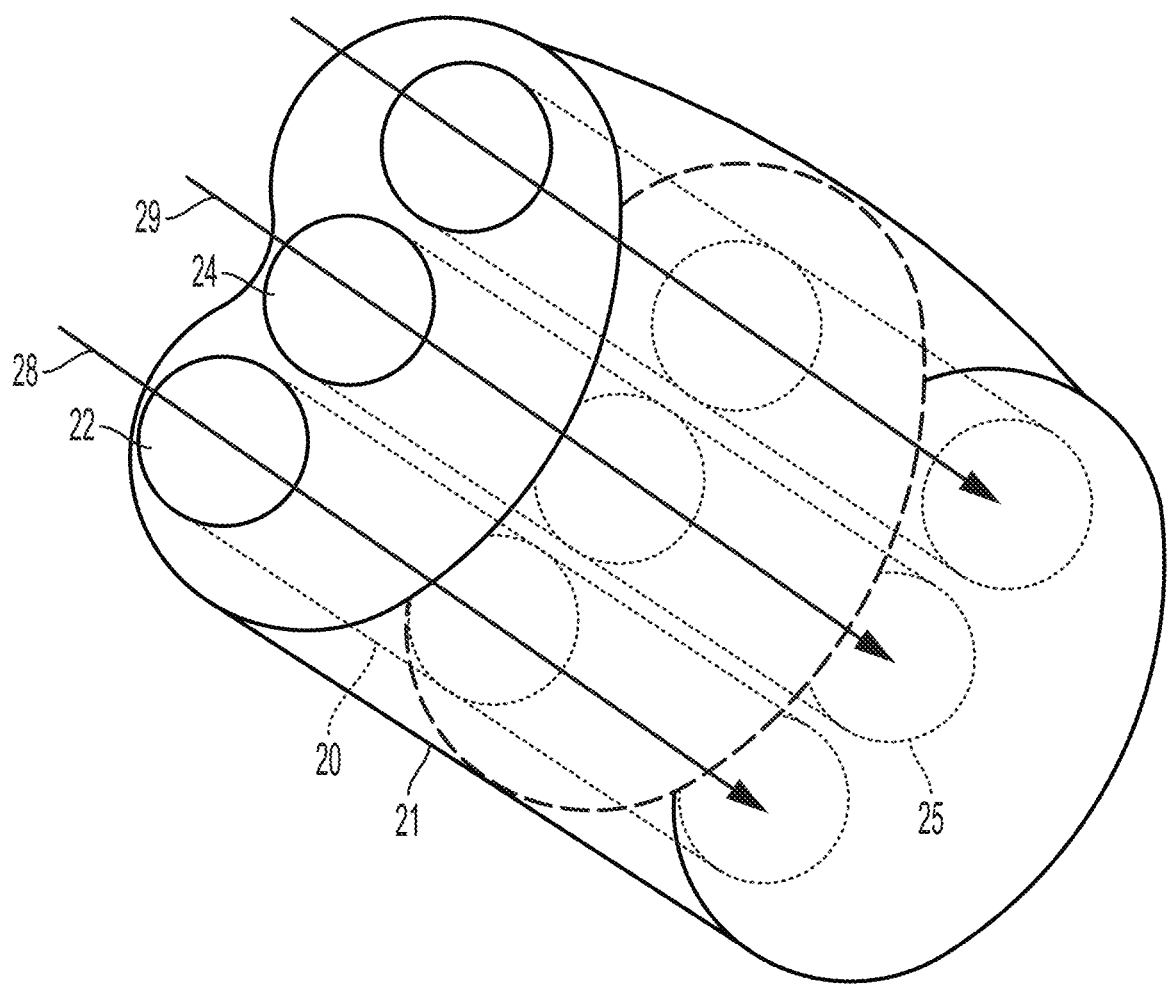
FIG. 2 is a perspective view of an example irradiation target treated by scanning a particle beam column-by-column across the target.

In some implementations, after a column of the target has been treated as described in the preceding paragraph, the particle beam is directed along a new, different path through the target. For example, as shown in FIG. 2, a column 20 of target 21 is treated by varying the energy of a particle beam 22 that proceeds along the direction of arrow 28. The particle beam is then directed along a new path 24 through target 21 where it proceeds along the direction of arrow 29. A column 25 is then treated along that new path by varying the energy of the particle beam while the particle beam is stationary. As noted, the column is located along the longitudinal extent of the beam. In some implementations, the particle beam is directed along each path through the target only once when treating columns of the target. As a result, healthy tissue above or below target 21 is exposed to the ultra-high dose rate of radiation once but not to multiple low doses of radiation as occurs when targets are treated layer-by-layer as in FIG. 1.

In other words, in some implementations the particle beam is directed along a new path and upstream tissue along that path is never visited again. In this way, each location within the target can be treated at a rate that is comparable to that of an individual pencil beam modulated with the layer switching time. The average dose rate over the entire treatment may be comparable to layer-by-layer radiation deliveries, but the localized dose rate for any one spot is at an ultra-high dose rate. In some cases, a reduction in damage to healthy tissue may occur when radiation is delivered at ultra-high dose rates. For example, when delivering radiation doses of 10 to 20 Gray in pulses of less than 500 ms—reaching effective dose rates of 20 to 100 Gray-per-second—healthy tissue may be less damaged than when irradiated with the same dose over a longer time scale, while the delivered radiation may treat tumors with the same level of effectiveness.

In some implementations, the operational speed of hardware used to produce and to condition the particle beam may affect the ability to deliver radiation at ultra-high dose rates. For example, in order to achieve ultra-high dose rates, the energy of the particle beam may be changed at a rate that exceeds changes of energy used for layer-by-layer scanning. For example, ultra-high dose rates applied to columns of a target may be achieved by switching beam energy in a duration of 50 ms. This may be achieved, for example, by controlling motion of the particle beam and motion of energy-absorbing plates containing boron carbide or other structures containing boron carbide into and out of the path of the particle beam. By way of example, a 5 centimeter (cm) deep column, which might require 5 layer switches, may require 250 ms of down-time during which particle beam is not delivered, allowing 250 ms of beam delivery during which 10 to 20 Gray of dose may be delivered. Faster motion of the energy-absorbing plates and/or additional coordination of beam motion may further decrease the layer switching time allowing even more time to deliver the required treatment dose while still meeting the requirement for a localized ultra-high dose rate.

Also described herein are example implementations of a collimator for use with the particle therapy system. Use of a collimation to isolate adjacent spots (e.g., FIG. 1) or adjacent columns (e.g., FIG. 2) from each other may enable the system to achieve FLASH dose rates or non-FLASH dose rates in localized regions, such as a spot or a column, without the radiation leaking into adjacent regions or with minimal acceptable amounts of the radiation leaking into adjacent regions.

In some implementations, the collimator may include a carrier having one or more openings, such as one or more holes or slots, through which a particle beam passes to the target in the patient. The carrier may be a plate, a polyhedron, or a curved three-dimensional (3D) structure that is made of a material that inhibits passage of the particle beam. For example, the carrier may be made of a metal such as nickel, brass, or tungsten having a thickness sufficient to prevent passage of radiation at a given energy. In some implementations, the sizes and shapes of one or more of the openings are fixed; for example, the sizes and shapes are not changeable or configurable. For example, the shape and content of the collimator may be static. The particle beam is movable within an opening or between openings. Each opening trims the particle beam by allowing part of the particle beam to pass through the opening to reach the target in the patient while preventing a different part of the particle beam from reaching the patient. The trimming may collimate the particle beam. For example, as a result of the trimming, the amount of dispersion along the beam path may be reduced.

A control system, such as a computing system, may be configured to control movement of the particle beam to a first hole (an example of an opening) of the collimator to enable at least part of the particle beam to reach the patient, to change an energy of the particle beam while the particle beam remains stationary at the first hole, and to control movement of the particle beam from the first hole to a second hole. The control system may also be configured to change an energy of the particle beam while the particle beam remains stationary at the second hole and to control movement of the particle beam from the second hole to multiple additional holes. At each of the multiple additional holes, the particle beam is controlled to remain stationary for a period of time while the energy of the particle beam changes. As a result, at each hole, the particle beam is trimmed and, by virtue of the energy change, the particle beam treats a three-dimensional column within the target.

The speed of operation of a collimator used in a particle therapy system may affect the system's ability to deliver radiation at ultra-high dose rates. The example collimator described herein may have limited or no configurability and therefore may reduce or eliminate the amount of time required to configure the collimator during treatment. As a result, the collimator may be particularly useful when delivering radiation at ultra-high (FLASH) dose rates. The collimator may, however, be used when delivering radiation at dose rates that are not ultra-high. In some implementations, a configurable collimator may be used.

Figure 3:
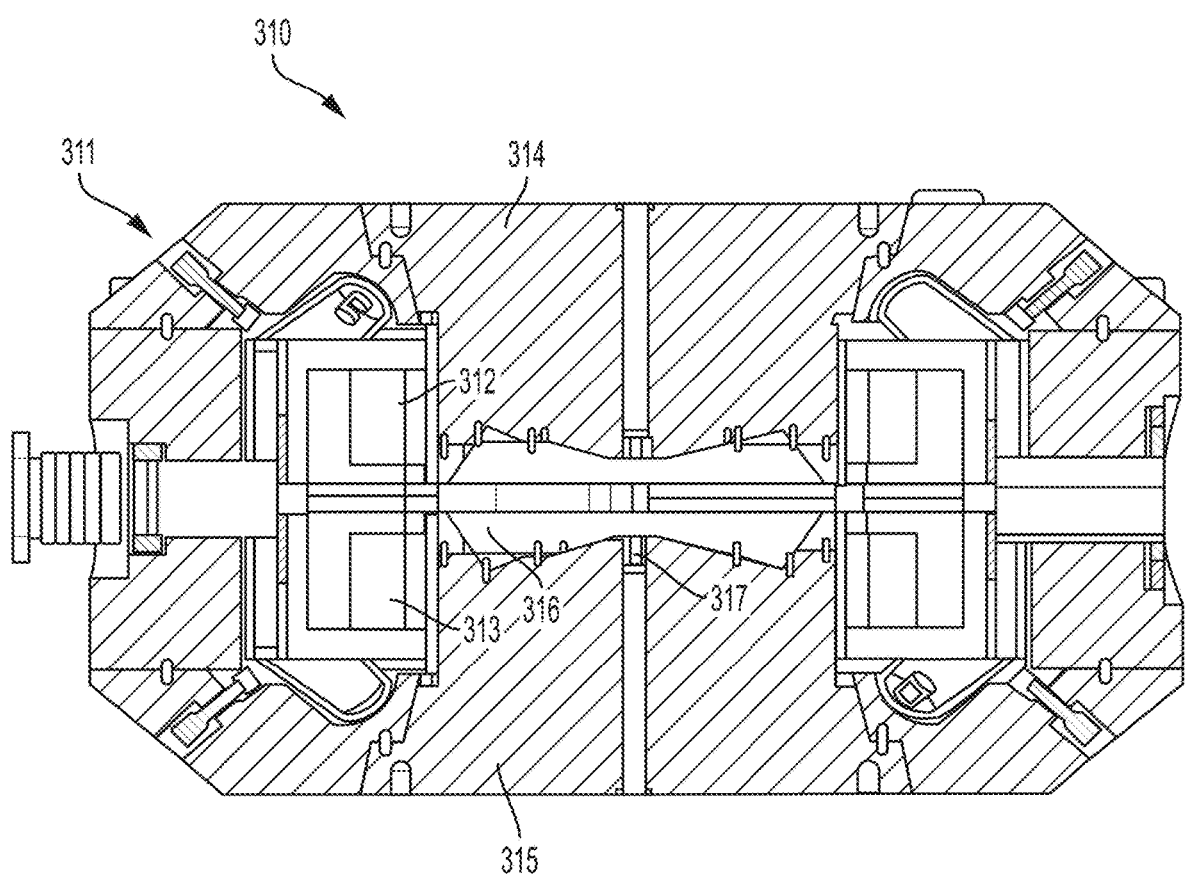
FIG. 3 is a cut-away view of part of an example particle accelerator that is usable in the particle therapy system described herein.

Described below are example implementations of a particle therapy system configured to deliver radiation at ultra-high dose rates through three-dimensional columns of a target. In an example implementation, the particle therapy system is a proton therapy system. As described herein, an example proton therapy system scans a proton beam in three dimensions across an irradiation target in order to destroy malignant tissue. FIG. 3 shows a cross-section of components 310 of an example superconducting synchrocyclotron that may be used to provide a particle (e.g., a proton) beam in the proton therapy system. In this example, components 310 include a superconducting magnet 311. The superconducting magnet includes superconducting coils 312 and 313. The superconducting coils are formed of multiple integrated conductors, each of which includes superconducting strands—for example, four strands or six strands—wound around a center strand which may itself be superconducting or non-superconducting. Each of the superconducting coils 312, 313 is for conducting a current that generates a magnetic field (B). The magnetic yokes 314, 315 or smaller magnetic pole pieces shape the magnetic field in a cavity 316 in which particles are accelerated. In an example, a cryostat (not shown) uses liquid helium (He) to conductively cool each coil to superconducting temperatures, e.g., around 4° Kelvin (K).

In some implementations, the particle accelerator includes a particle source 317, such as a Penning Ion Gauge—PIG source, to provide an ionized plasma column to cavity 316. Hydrogen gas, or a combination of hydrogen gas and a noble gas, is ionized to produce the plasma column. A voltage source provides a varying radio frequency (RF) voltage to cavity 316 to accelerate particles from the plasma column within the cavity. As noted, in an example, the particle accelerator is a synchrocyclotron. Accordingly, the RF voltage is swept across a range of frequencies to account for relativistic effects on the particles, such as increasing particle mass, when accelerating particles within the acceleration cavity. The RF voltage drives a dee plate contained within the cavity and has a frequency that is swept downward during the accelerating cycle to account for the increasing relativistic mass of the protons and the decreasing magnetic field. A dummy dee plate acts as a ground reference for the dee plate. The magnetic field produced by running current through the superconducting coils, together with sweeping RF voltage, causes particles from the plasma column to accelerate orbitally within the cavity and to increase in energy as a number of turns increases.

The magnetic field in the cavity is shaped to cause particles to move orbitally within the cavity. The example synchrocyclotron employs a magnetic field that is uniform in rotation angle and falls off in strength with increasing radius. In some implementations, the maximum magnetic field produced by the superconducting (main) coils may be within the range of 4 Tesla (T) to 20 T at a center of the cavity, which falls off with increasing radius. For example, the superconducting coils may be used in generating magnetic fields at, or that exceed, one or more of the following magnitudes: 4.0 T, 4.1 T, 4.2 T, 4.3 T, 4.4 T, 4.5 T, 4.6 T, 4.7 T, 4.8 T, 4.9 T, 5.0 T, 5.1 T, 5.2 T, 5.3 T, 5.4 T, 5.5 T, 5.6 T, 5.7 T, 5.8 T, 5.9 T, 6.0 T, 6.1 T, 6.2 T, 6.3 T, 6.4 T, 6.5 T, 6.6 T, 6.7 T, 6.8 T, 6.9 T, 7.0 T, 7.1 T, 7.2 T, 7.3 T, 7.4 T, 7.5 T, 7.6 T, 7.7 T, 7.8 T, 7.9 T, 8.0 T, 8.1 T, 8.2 T, 8.3 T, 8.4 T, 8.5 T, 8.6 T, 8.7 T, 8.8 T, 8.9 T, 9.0 T, 9.1 T, 9.2 T, 9.3 T, 9.4 T, 9.5 T, 9.6 T, 9.7 T, 9.8 T, 9.9 T, 10.0 T, 10.1 T, 10.2 T, 10.3 T 10.4 T, 10.5 T, 10.6 T, 10.7 T, 10.8 T, 10.9 T, 11.0 T, 11.1 T, 11.2 T, 11.3 T, 11.4 T, 11.5 T, 11.6 T, 11.7 T, 11.8 T, 11.9 T, 12.0 T, 12.1 T, 12.2 T, 12.3 T, 12.4 T, 12.5 T, 12.6 T, 12.7 T, 12.8 T, 12.9 T, 13.0 T, 13.1 T, 13.2 T, 13.3 T, 13.4 T, 13.5 T, 13.6 T, 13.7 T, 13.8 T, 13.9 T, 14.0 T, 14.1 T, 14.2 T, 14.3 T, 14.4 T, 14.5 T, 14.6 T, 14.7 T, 14.8 T, 14.9 T, 15.0 T, 15.1 T, 15.2 T, 15.3 T, 15.4 T, 15.5 T, 15.6 T, 15.7 T, 15.8 T, 15.9 T, 16.0 T, 16.1 T, 16.2 T, 16.3 T, 16.4 T, 16.5 T, 16.6 T, 16.7 T, 16.8 T, 16.9 T, 17.0 T, 17.1 T, 17.2 T, 17.3 T, 17.4 T, 17.5 T, 17.6 T, 17.7 T, 17.8 T, 17.9 T, 18.0 T, 18.1 T, 18.2 T, 18.3 T, 18.4 T, 18.5 T, 18.6 T, 18.7 T, 18.8 T, 18.9 T, 19.0 T, 19.1 T, 19.2 T, 19.3 T, 19.4 T, 19.5 T, 19.6 T, 19.7 T, 19.8 T, 19.9 T, 20.0 T, 20.1 T, 20.2 T, 20.3 T, 20.4 T, 20.5 T, 20.6 T, 20.7 T, 20.8 T, 20.9 T, or more. Furthermore, the superconducting coils may be used in generating magnetic fields that are outside the range of 4 T to 20 T or that are within the range of 4 T to 20 T but that are not specifically listed herein.

In some implementations, such as the implementations shown in FIG. 3, the relatively large ferromagnetic magnetic yokes 314, 315 act as returns for stray magnetic fields produced by the superconducting coils. In some systems, a magnetic shield (not shown) surrounds the yokes. The return yokes and the shield together act to reduce stray magnetic fields, thereby reducing the possibility that stray magnetic fields will adversely affect the operation of the particle accelerator.

In some implementations, the return yokes and shield may be replaced by, or augmented by, an active return system. An example active return system includes one or more active return coils that conduct current in a direction opposite to current through the main superconducting coils. In some example implementations, there is an active return coil for each superconducting main coil, e.g., two active return coils—one for each main superconducting coil. Each active return coil may also be a superconducting coil that surrounds the outside of a corresponding main superconducting coil concentrically.

By using an active return system, the relatively large ferromagnetic magnetic yokes 314, 315 can be replaced with magnetic pole pieces that are smaller and lighter. Accordingly, the size and weight of the synchrocyclotron can be reduced further without sacrificing performance. An example of an active return system that may be used is described in U.S. Pat. No. 8,791,656 entitled "Active Return System", the contents of which are incorporated herein by reference.

At or near the output of an extraction channel of the particle accelerator, there may be one or more beam shaping elements including a scanning system. Components of the scanning system may be mounted on, or otherwise attached to, a nozzle for positioning relatively close to the patient during treatment.

Figure 4:
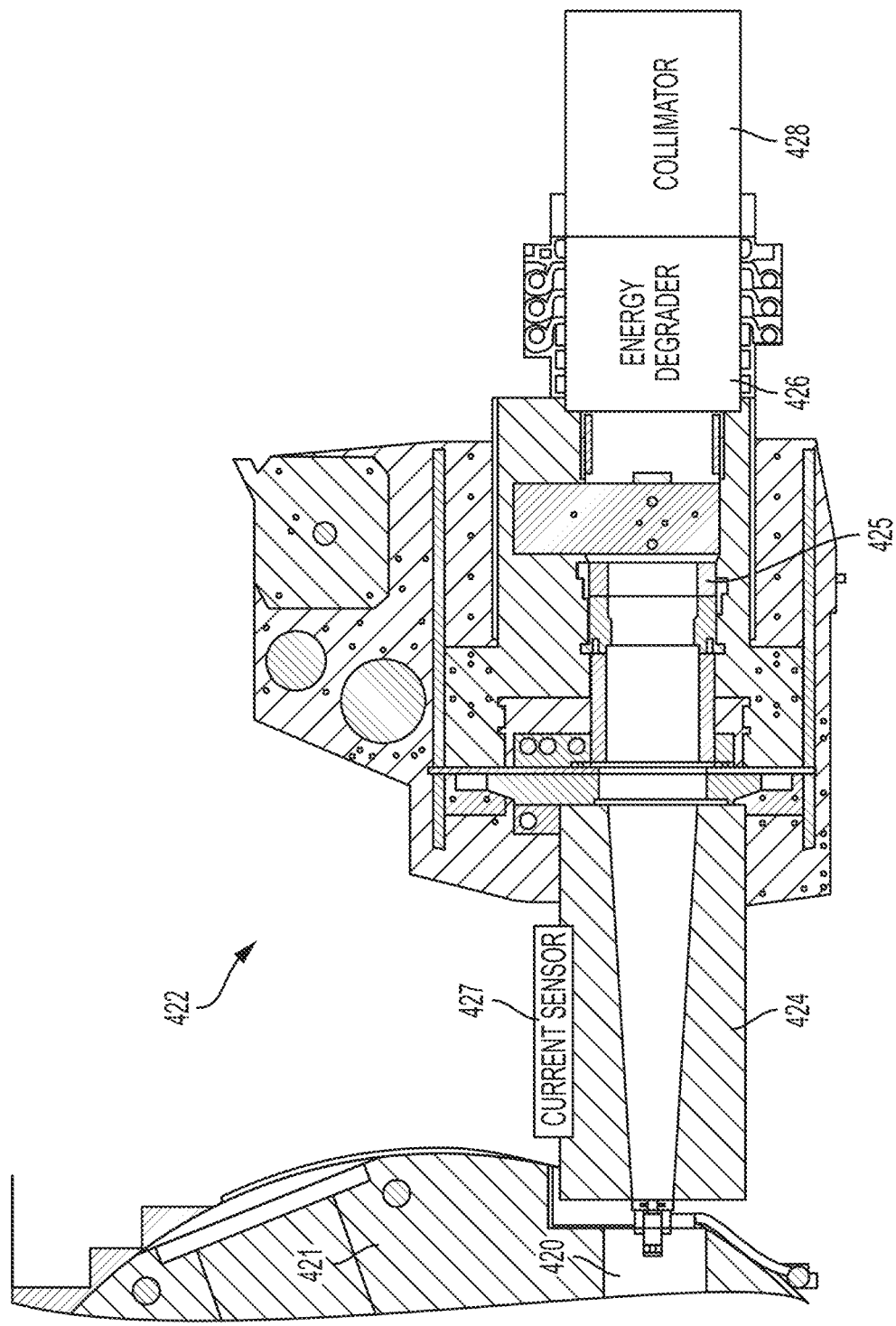
FIG. 4 is a side view of components of an example scanning system that is usable in the particle therapy system described herein.
Figure 5:
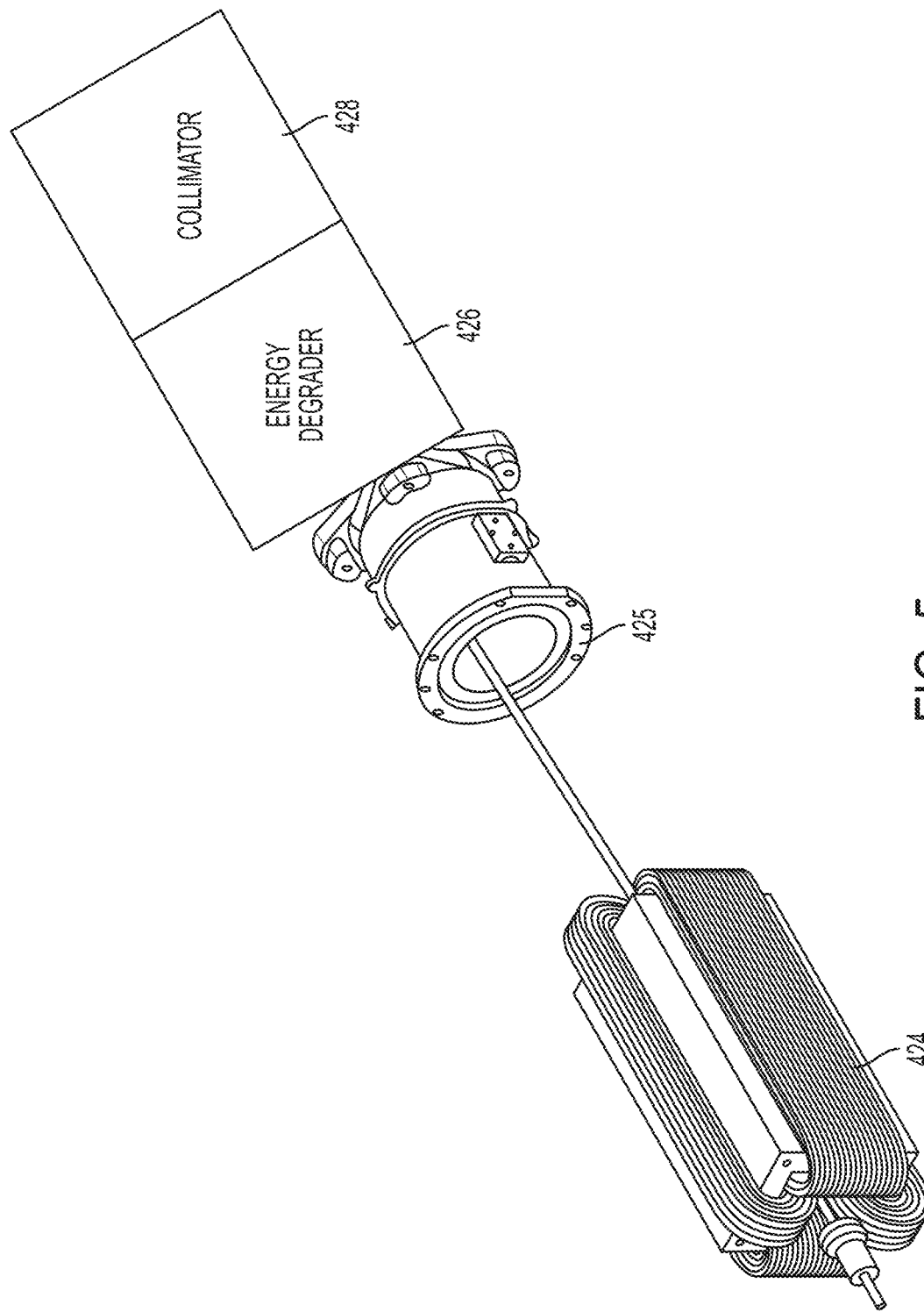
FIG. 5 is a perspective view of components of the example scanning system that is usable in the particle therapy system described herein.

Referring to FIG. 4, in an example implementation, at the output of extraction channel 420 of synchrocyclotron 421 (which may have the configuration of FIG. 3) are example scanning components 422 that may be used to move the particle beam three-dimensionally over and through an irradiation target. FIG. 5 also shows examples of the components of FIG. 4. These include, but are not limited to, one or more scanning magnets 424, an ion chamber 425, an energy degrader 426, and a collimator 428. Other components that may be down-beam of the extraction channel are not shown in FIG. 4 or 5 and may include, for example, one or more scattering devices for changing beam spot size. An example scattering device includes a plate or range modulator that disperses the particle beam as the particle beam passes through the scattering device.

In an example operation, scanning magnet 424 is controllable in two dimensions (e.g., Cartesian XY dimensions) to position the particle beam in those two dimensions and to move the particle beam across at least a part of an irradiation target. Ion chamber 425 detects the dosage of the beam and feeds-back that information to a control system to adjust beam movement. Energy degrader 426 is controllable to move structures into, and out of, the path of the particle beam to change the energy of the particle beam and therefore the depth to which dose of the particle beam will be deposited in the irradiation target. Examples of such structures include, but are not limited to, energy-absorbing plates; polyhedra such as wedges, tetrahedra, or toroidal polyhedra; and curved three-dimensional shapes, such as cylinders, spheres, or cones. In this way, the energy degrader can cause the particle beam to deposit doses of radiation in the interior of an irradiation target to treat columns of the target. In this regard, when protons move through tissue, the protons ionize atoms of the tissue and deposit a dose along their path. The Bragg peak is a pronounced peak on the Bragg curve which plots the energy loss of ionizing radiation during its travel through tissue. The Bragg peak represents the depth at which most protons deposit within tissue. For protons, the Bragg peak occurs right before the particles come to rest. Accordingly, the energy of the particle beam may be changed to change the location of its Bragg peak and, therefore, where a majority of the dose of protons will deposit in depth in the tissue.

Figure 6:
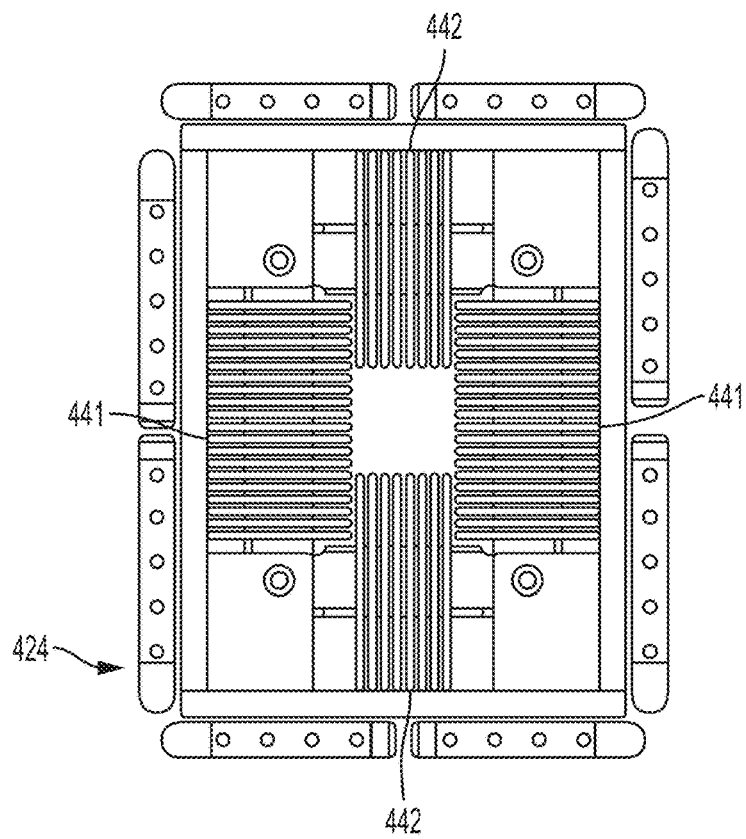
FIG. 6 is a front view of an example magnet for use in a scanning system of the type shown in FIGS. 4 and 5.
Figure 7:
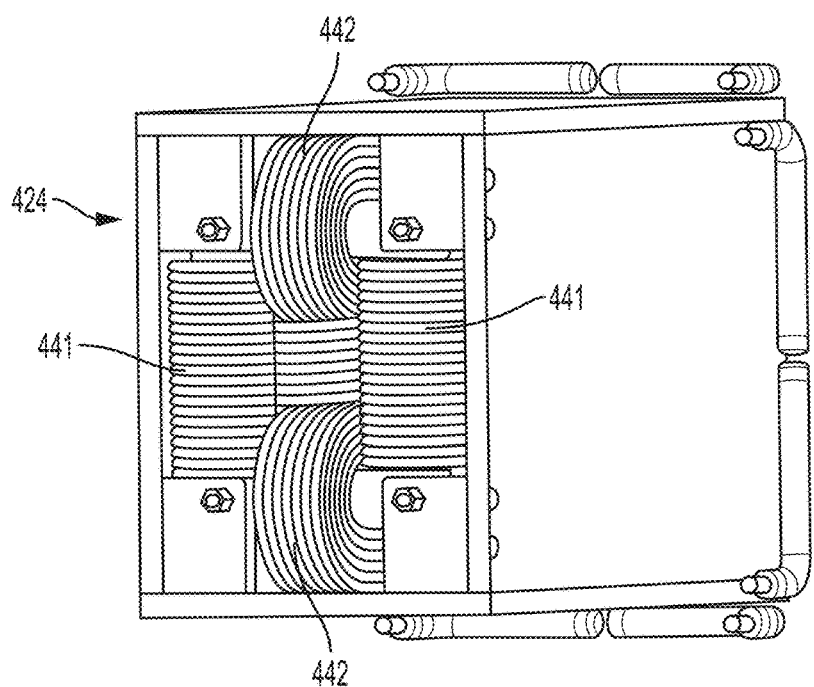
FIG. 7 is a perspective view of an example magnet for use in a scanning system of the type shown in FIGS. 4 and 5.

FIGS. 6 and 7 show views of an example scanning magnet 424. In this example, scanning magnet 424 includes two coils 441, which control particle beam movement in the X dimension, and two coils 442, which control particle beam movement in the Y dimension. Control is achieved, in some implementations, by varying current through one or both sets of coils to thereby vary the magnetic field(s) produced thereby. By varying the magnetic field(s) appropriately, the particle beam can be moved in the X and/or Y dimension across the irradiation target. The energy degrader described previously can move the beam in the Z dimension through the target, thereby enabling scanning in three dimensions.

Referring back to FIG. 4, a current sensor 427 may be connected to, or be otherwise associated with, scanning magnet 424. For example, the current sensor may be in communication with, but not connected to, the scanning magnet. In some implementations, the current sensor samples current applied to magnet 424, which may include current to the coil(s) for controlling beam scanning in the X dimension and/or current to the coil(s) for controlling beam scanning in the Y dimension. The current sensor may sample current through the magnet at times that correspond to the occurrence of pulses in the particle beam or at a rate that exceeds the rate that the pulses occur in the particle beam. The samples, which identify the magnet current, are correlated to detection of the pulses by the ion chamber described below. For example, the times at which pulses are detected using the ion chamber may be correlated in time to samples from the current sensor, thereby identifying the current in the magnet coil(s) at the times of the pulses. Using the magnet current, it thus may be possible to determine the location within the irradiation target where each pulse, and thus dose of radiation—that is, dose of particles—was delivered. The location of the dose delivered within the target may also be determined based on the configuration of the energy degrader, for example, based on the number of plates in the beam path.

During operation, the magnitude value of the magnet current may be stored for each location at which a dose is delivered, along with the amount (e.g., intensity) of the dose. A control system, which may be either on the accelerator or remote from the accelerator and which may include memory and one or more processing devices, may correlate the magnet current to coordinates within the irradiation target, and those coordinates may be stored along with the amount of the dose. For example, the location may be identified by depth-wise layer number and Cartesian XY coordinates or by Cartesian XYZ coordinates, with the depth-wise layer corresponding to the Z coordinate. In some implementations, both the magnitude of the magnet current and the coordinate locations may be stored along with the dose at each location. This information may be stored in memory either on, or remote from, the accelerator. This information may be used to track treatment of the target and to maintain a record of that treatment.

Ion chamber 425 detects dosage, such as one or more individual doses, applied by the particle beam to positions within the irradiation target by detecting the numbers of ion pairs created within a gas caused by incident radiation. The numbers of ion pairs correspond to the dose provided by the particle beam. That information is fed-back to the control system and stored in memory along with the time that the dose is provided. This information may be correlated to, and stored in association with, the location at which the dose was provided and/or the magnitude of the magnet current at that time, as described above.

Collimator 428 may be located down-beam of the scanning magnets and down-beam of the energy degrader, as shown in FIGS. 4 and 5. The collimator may trim the particle beam on a spot-by-spot basis during movement of the particle beam from path to path through the target. The collimator may also trim the particle beam while the particle beam is stationary on the target and when the energy of the stationary particle beam changes to impact different portions of the interior of the target. For example, the particle beam may spread along its diameter as it enters the interior of the target. The collimator may be configured—for example, constructed—to trim the particle beam to account for that spread. For example, the collimator may be configured to reduce beam dispersion to and through the target and thereby maintain a more constant spot size.

As described below, in some examples, the collimator may include one or more openings, through which the particle beam may be steered. For example, the collimator may include multiple holes, such as circular holes, arranged in a one-dimensional array or in a multi-dimensional array. The sizes and shapes of the holes are not changeable or configurable in some examples. The particle beam may be moved to the holes in a specified sequence to treat portions of the target in the patient. Each hole may trim and collimate the particle beam. The holes may be positioned sufficiently close to each other to limit the amount that individual spots of the particle beam overlap. This may be done in order to limit exposure of healthy tissue above and below the target to a single dose of ultra-high dose rate radiation. In some implementations, the holes may be formed through a carrier, such as a substrate that inhibits or blocks the radiation. The carrier itself may be movable within the beam field based, for example, on movement of the particle beam. For instance, a carrier having a linear array of holes may be configured to track motion of the particle beam across the beam field. However, because the holes themselves do not need to be configured, the amount of time required for movement of the carrier does not prevent delivery of radiation at ultra-high dose rates.

In some implementations, the collimator may include one or more slots through the carrier instead of, or in addition to, holes. For example, the collimator may include a single linear slot having a lateral dimension that is sufficient to trim the particle beam and a longitudinal dimension that extends across at least part of the radiation target and that can accommodate multiple particle beam spots. In some implementations, the collimator may include multiple linear slots arranged in an array. The sizes and shapes of the slots are not changeable or configurable in some examples. The particle beam may be moved to parts of each slot, which performs collimation in the lateral dimension (and in the longitudinal dimension at the slot endpoints). In some implementations, the slots may be formed through a carrier, such as a substrate that inhibits or blocks the radiation. The carrier itself may be movable within the beam field based, for example, on movement of the particle beam. For instance, a carrier having a single slot may be configured to track motion of the particle beam across the beam field. However, because the slot itself does not need to be configured, the amount of time required for movement of the carrier does not prevent delivery of radiation at ultra-high dose rates.

Figure 8:
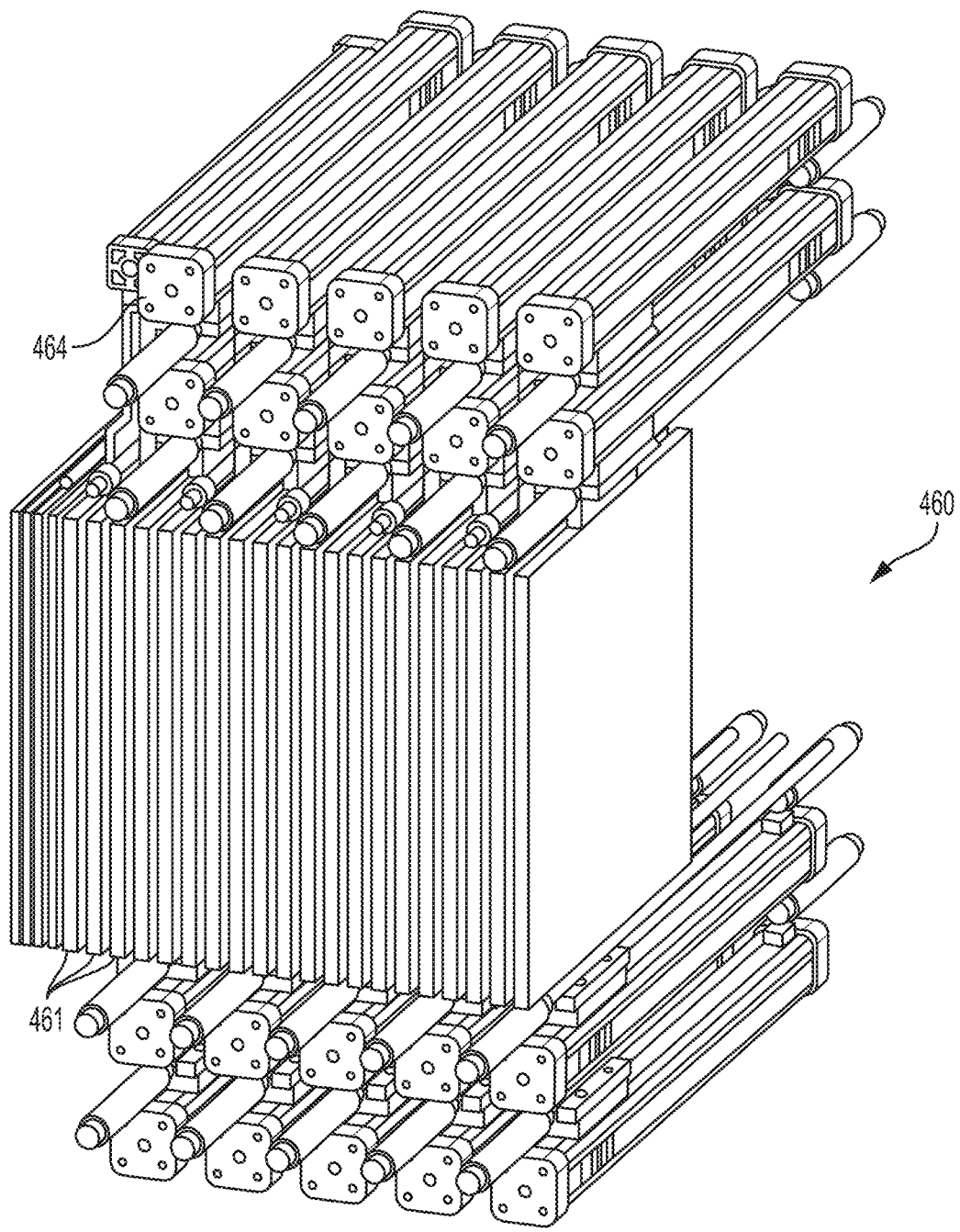
FIG. 8 is a perspective view of an example energy degrader (e.g., range modulator) for use in a scanning system of the type shown in FIGS. 4 and 5.

FIG. 8 shows an example range modulator 460, which is an example implementation of energy degrader 426. In some implementations, range modulator 460 may be located down-beam of the scanning magnets between the collimator and the patient. In some implementations, such as that shown in FIG. 8, the range modulator includes a series of plates 461. The plates may be made of one or more of the following example materials: polycarbonate such as LEXAN™, carbon, beryllium, boron carbide, a composite material comprised of boron carbide and graphite, or a material of low atomic number. Other materials, however, may be used in place of, or in addition to, these example materials. In other implementations of the energy degrader that include polyhedra such as wedges, tetrahedra, or toroidal polyhedra, or curved three-dimensional structures, such as cylinders, spheres, or cones, these structures may be made of one or more of the following example materials: polycarbonate such as LEXAN™, carbon, beryllium, boron carbide, a composite material comprised of boron carbide and graphite, or a material of low atomic number.

In some implementations, structures of the range modulator containing boron carbide may include only boron carbide; that is, the structures may be pure boron carbide. In some implementations, structures containing boron carbide may include boron carbide in combination with another material, such as graphite, polycarbonate, carbon, or beryllium. In some implementations, every structure—for example, plate, polyhedron, or curved three-dimensional structure—in the energy degrader may contain all or part boron carbide. In some implementations, different structures—for example, plates, polyhedra, or curved three-dimensional structures—in the energy degrader may include different materials. For example, one or more plates in the energy degrader may be made of pure boron carbide and one or more other plates of the same energy degrader may be made of or include one or more of polycarbonate, carbon, and/or beryllium. Other materials may also be used. For example, one or more plates or portions thereof in the energy degrader may be made of a composite material comprised of boron carbide and graphite.

Figure 9:
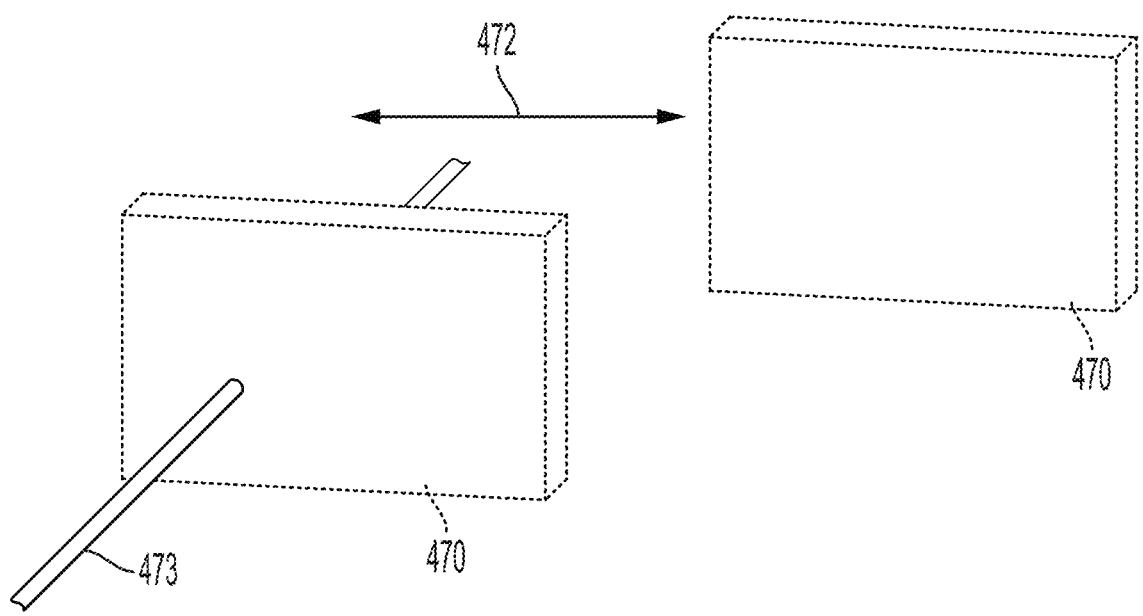
FIG. 9 is a perspective view of a process for moving a plate of the energy degrader into and out of the path of a particle beam.

One or more of the plates is movable into, or out of, the beam path to thereby change the energy of the particle beam and, thus, the depth at which most of the dosage of the particle beam is deposited within the irradiation target. Plates are moved physically into and out of the path of the particle beam. For example, as shown in FIG. 9, a plate 470 moves along the direction of arrow 472 between positions in the path of the particle beam 473 and outside the path of the particle beam. The plates are computer-controlled. Generally, the number of plates that are moved into the path of the particle beam corresponds to the depth at which scanning of an irradiation target is to take place. Thus, dosage from the particle beam can be directed into the interior of a target by appropriate control of one or more plates.

In some implementation, individual plates of range modulator 460 are each coupled to, and driven by, a corresponding motor 464. In general, a motor includes a device that converts some form of energy into motion. A motor may be rotary or linear, and may be electric, hydraulic, or pneumatic. For example, each motor may be an electrical motor that drives a lead screw to extend a plate into the beam field or to retract a plate out of the beam field, including to cause motion of the plate to track or to trail motion of the particle beam within the beam field. For example, each motor may be a rotary motor that drives a corresponding linear actuator to control movement of a corresponding structure. In some implementations, individual plates of range modulator 460 are each coupled to, and driven by, a corresponding actuator. In some examples, actuators include mechanical or electromechanical devices that provide controlled movements and that can be operated electrically by motors, hydraulically, pneumatically, mechanically, or thermally. In some examples, an actuator includes any type of motor that is operated by a source of energy, such as electric current, hydraulic fluid pressure, or pneumatic pressure, and that converts that energy into motion.

In some implementations, an energy degrader containing boron carbide structures (or structures comprised of other material) may be located in the treatment room where the particle beam is applied to the patient. For example, the energy degrader may be located between the scanning magnet and the patient. In an example, the energy degrader may be located in a nozzle on a system's inner gantry, examples of which are described with respect to FIGS. 26, 27, and 28.

The energy degrader may be located close to the patient so as to limit the amount that the particle beam is scattered or dispersed following passage through one or more plates or other structures. In some implementations, the energy degrader may be located no more than four meters from the patient along a beamline of the particle beam. In some implementations, the energy degrader may be located no more than three meters from the patient along a beamline of the particle beam. In some implementations, the energy degrader may be located no more than two meters from the patient along a beam line of the particle beam. In some implementations, the energy degrader may be located no more than one meter from the patient along a beamline of the particle beam. In some implementations, the energy degrader may be located no more than one-half a meter from the patient along a beamline of the particle beam. In some implementations, the energy degrader may be located within the nozzle no more than four meters from the patient along a beamline of the particle beam. In some implementations, the energy degrader may be located within the nozzle no more than three meters from the patient along a beamline of the particle beam. In some implementations, the energy degrader may be located within the nozzle no more than two meters from the patient along a beamline of the particle beam. In some implementations, the energy degrader may be located within the nozzle no more than one meter from the patient along a beam line of the particle beam. In some implementations, the energy degrader may be located within the nozzle no more than one-half a meter from the patient along a beam line of the particle beam.

In general, boron carbide may be cheaper and safer to use than some other materials that may be used to degrade the energy of the particle beam, such as beryllium. In general, boron carbide has a relatively low atomic weight and a high density and may compare favorably in its scattering properties to some other materials that may be used to degrade the energy of the particle beam, such as carbon (e.g., graphite) and polycarbonate. Reducing the beam scattering results in a reduced beam spot size; that is, the cross-sectional size of the beam. A reduced spot size provides for improved conformality in a pencil beam scanning system and higher localized dose rate. In other words, reducing the spot size reduces the area over which dose is deposited. As a result, the concentration of protons deposited within a single spot increases, thereby increasing the dose rate within the area of the single spot. Increasing the dose rate within the area of the single spot is desirable when performing scanning using ultra-high (or "FLASH") dose rates since it facilitates deposition of an ultra-high dose of protons within a prescribed period. Examples of periods during which ultra-high doses are applied are described herein.

Figure 29:
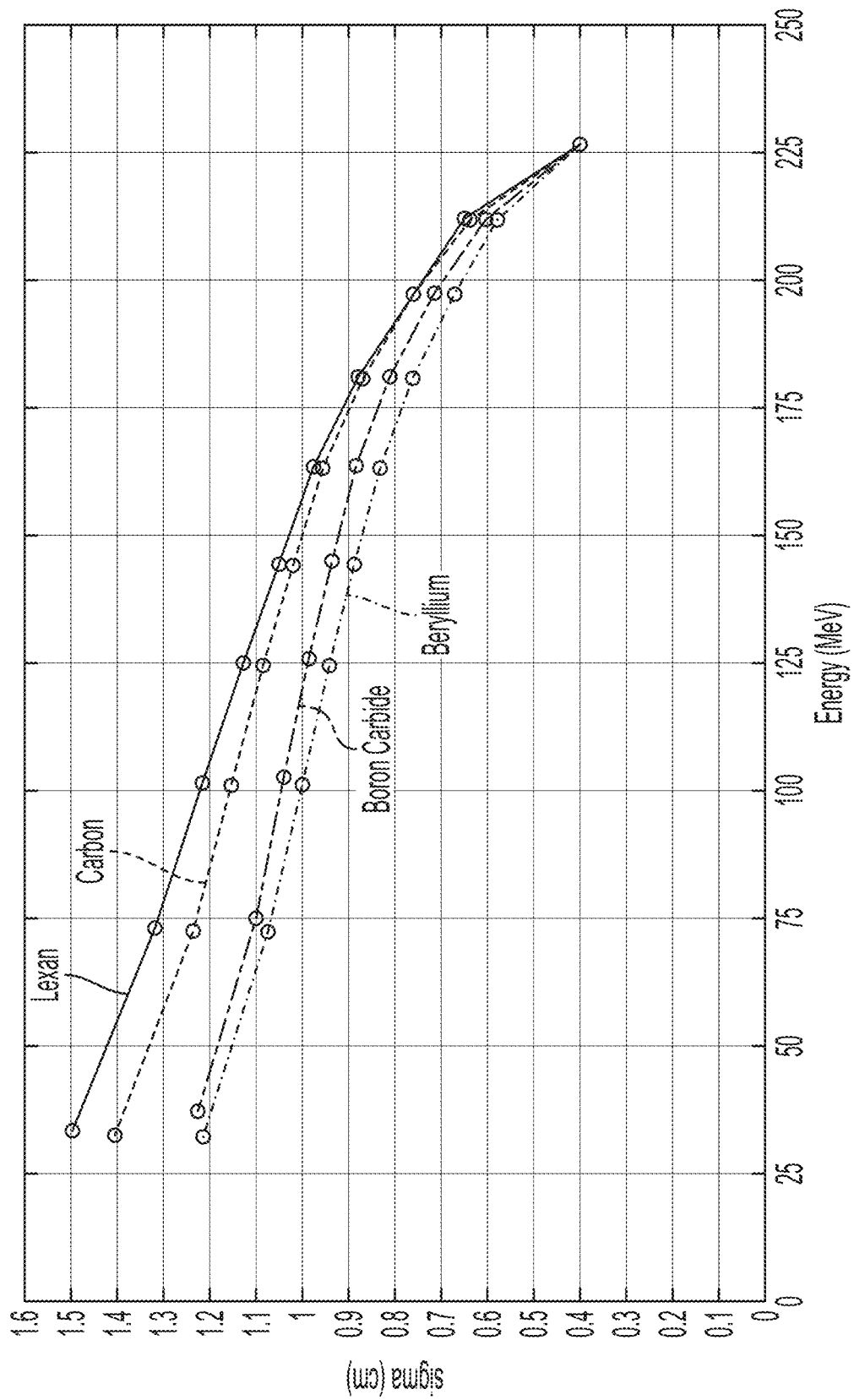
FIG. 29 is a graph showing changes in particle beam spot size for different particle beam energies for different materials used in the energy degrader to change the energy of the particle beam.

FIG. 29 is a graph showing the change in particle beam spot size for different particle beam energies for different materials used in the energy degrader to change the energy of the particle beam. In this example, LEXAN™, carbon (e.g., graphite), boron carbide, and beryllium are shown. According to the graph of FIG. 29, for example, a boron carbide degrader structure produces a particle beam having a spot size of less than 1.2 centimeters (cm) sigma at an energy of 70 MeV (Million electron Volts). In this example, the spot size is measured at the output of the degrader structure. The spot may scatter the farther the beam travels through the air, which will cause an increase in spot size. However, placing the degrader sufficiently close to the patient will limit scattering. In addition, in some but not all cases, a collimator may be placed between the energy degrader and the patient to collimate the particle beam and thereby limit effects caused by scattering.

In addition to the foregoing advantages, a boron carbide based energy degrader may be reduced in size relative to energy degraders that use polycarbonate, for example. That is, a boron carbide based energy degrader may achieve substantially the same effect as a polycarbonate based energy degrader, but the boron carbide based energy degrader may have a smaller form factor than the polycarbonate based energy degrader. This is because the density of boron carbide is greater than the density of polycarbonate. In some examples, an energy degrader comprised of pure boron carbide plates may be 30 centimeters (cm) to 40 cm thick along the beamline. The plates may have the same or varying thicknesses. The thickness of the plates and of the energy degrader itself will depend upon various factors such as the overall amount of energy change required and the number of layers to be treated, which may determine the number and thickness of each of the plates.

The reduced size of an energy degrader comprised of boron carbide makes the energy degrader less obtrusive in the treatment room. For example, an energy degrader comprised of all or some boron carbide structures may be housed within the nozzle on the inner gantry. The nozzle, including the energy degrader may be retracted fully within the inner gantry, thereby taking the energy degrader out of the way of a technician administering the treatment. In some implementations, the inner gantry may be flush with a wall of the treatment room, in which case retracting the nozzle and the energy degrader fully within the inner gantry causes the nozzle and energy degrader to retract fully within the wall.

Figure 10:
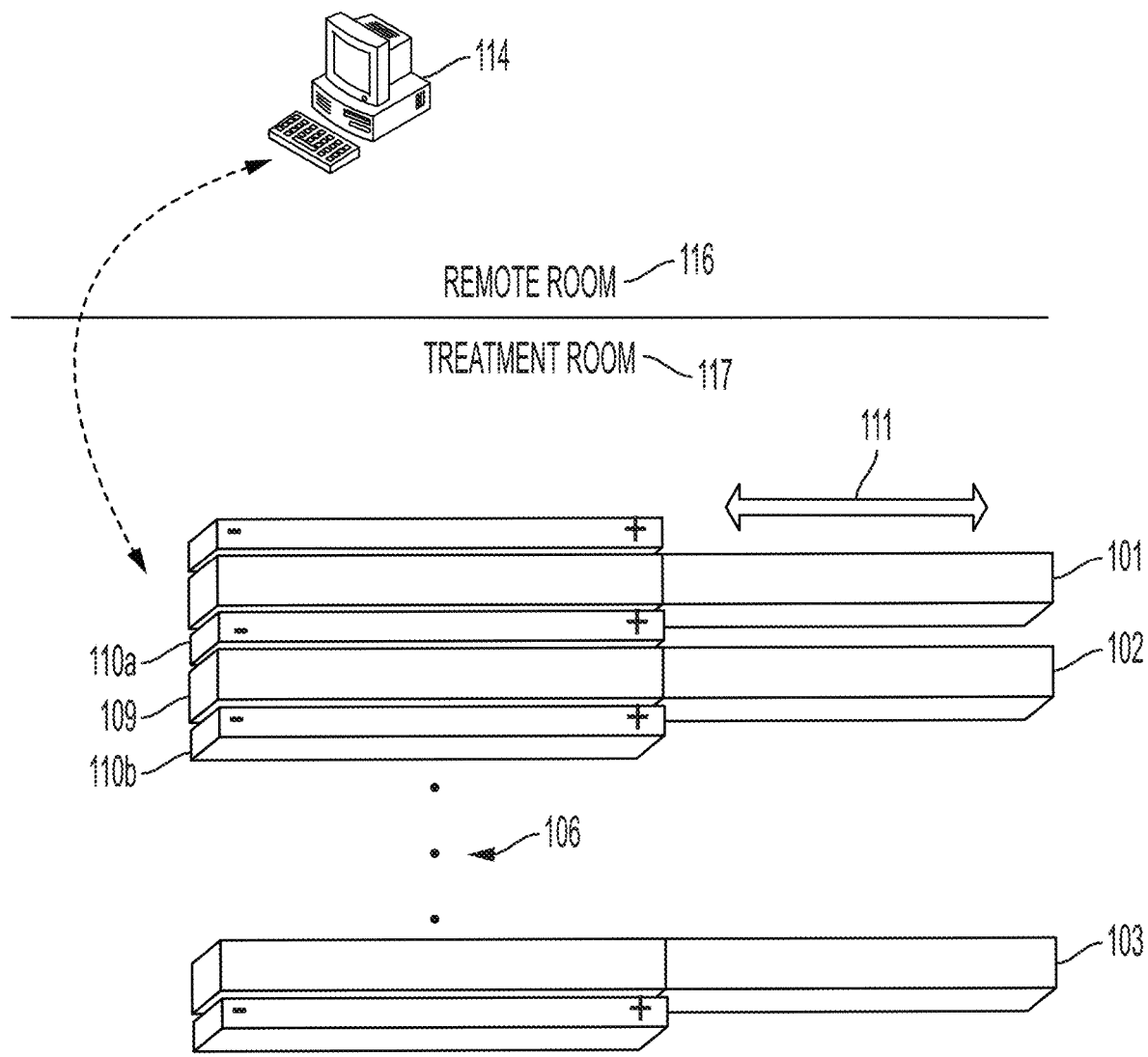
FIG. 10 is a block diagram of example linear motors and example plates of an energy degrader controlled thereby.

FIG. 10 shows an example implementation of a range modulator such as a boron carbide based range modulator that uses linear motors to control operations of energy-absorbing plates 101, 102, and 103. The range modulator of FIG. 10 may otherwise have the configuration of the range modulator of FIG. 8. Although only three plates are shown in the example of FIG. 10, any appropriate number of plates may be included, as illustrated by ellipses 106.

Taking plate 102 as an example, an example linear motor that controls operation of plate 102 includes a movable component and stationary component comprised of two parts—in this example, magnets 110*a* and 110*b*. The two magnets are arranged side-by-side, with their poles aligned. That is, as shown, the positive pole (+) of magnet 110*a* is aligned to the positive pole (+) of magnet 110*b*, and the negative pole (−) of magnet 110*a* is aligned to the negative pole (−) of magnet 110*b*. The movable component includes a coil-carrying plate 109 between magnets 110*a* and 110*b*. Coil-carrying plate 109 is connected physically to energy-absorbing plate 102 and controls movement of energy-absorbing plate 102 along the directions of arrow 111, e.g., into and out of the path of the particle beam.

As explained, coil-carrying plate 109 includes one or more conductive traces or other conductive structures that pass current in order to generate a magnetic field. The magnetic field is controlled by controlling the current through the coil-carrying plate in order to control movement of the coil-carrying plate, and thus of energy-absorbing plate 102. That is, current through the coils generates a magnetic field that interacts with the magnetic field produced by magnets 110*a* and 110*b*. This interaction causes movement of coil-carrying plate 109 and of energy-absorbing plate 102 along the direction of arrow 111, either into, or out of, the particle beam path. For example, larger magnetic fields generated by the coil-carrying plate 109 may cause the energy-absorbing plate to move into the particle beam path and smaller or opposite magnetic fields generated by the coil-carrying plate may cause the energy-absorbing plate to retract away from the particle beam path.

In some implementations, the conductive traces or other conductive structures on the coil-carrying plate may include three windings embedded in aluminum. In some implementations, the energy-absorbing plate may be physically attached to the coil-carrying plate and move with the coil-carrying plate. In some implementations, the number of windings and the materials used may be different than those described herein. In some implementations, the coil-carrying plate may be an integral part of the energy-absorbing plate. For example, the energy-absorbing plate itself may include the conductive structures or traces.

As shown in FIG. 10, in some implementations, the current through the coil-carrying plates may be controlled by signals received from a control system, such as computing system 114. The computing system may be susceptible to neutron radiation and, therefore, may be located in a remote room 116. In some implementations, remote room 116 may be shielded from neutron radiation produced by the particle accelerator. In some implementations, the remote room may be located far enough away from the treatment room 117 so as not to be affected by neutron radiation from the particle accelerator. In some implementations, the computing system may be located in the treatment room, but may be shielded from neutron radiation emitted by the particle accelerator. In some implementations, all computing functionality is shielded from neutron radiation and the electronics that are not shielded can still operate in the presence of neutron radiation. Encoders are examples of such electronics.

In this regard, encoders (not shown) may include or more of laser sensors, optic sensors, or diode sensors. The encoders detect movement of the coil-carrying plates, e.g., by detecting where markings or other indicia on the coil-carrying plates or on structures connected to, and that move with, the coil-carrying plates are located relative to the encoders. This information about where the coil-carrying plates are is fed back to the computing system and is used by the computing system to confirm the position of the coil-carrying plates during operation. The encoders may be located at any appropriate location. In some implementations, the encoders are located on a housing that includes the coil-carrying plates. As the plates move, markings or other indicia that move with the coil-carrying plates move past the encoders. The encoders then relay that information to computing system 114. Computing system 114 may use that information to control operation of the range modulator, including positioning its energy-absorbing plates.

Computing system 114, which may be comprised of one or more processing devices, may be programmed to control the proton therapy system, including components of the scanning system to implement ultra-high dose rate radiation treatment column-by-column in an irradiation target. For example, the computing system may be controllable to output one or more control signals to control one or more of the linear motors to extend or to retract one or more of the energy-absorbing plates during scanning. For example, the computing system may be controllable to output one or more control signals to control one or more electrical motors to extend or to retract one or more of the energy-absorbing plates during scanning. The computing system may include one or more processing devices, such as microprocessors, microcontrollers, field-programmable gate arrays (FPGAs), or applications-specific circuits (ASICs), for example.

Figure 11:
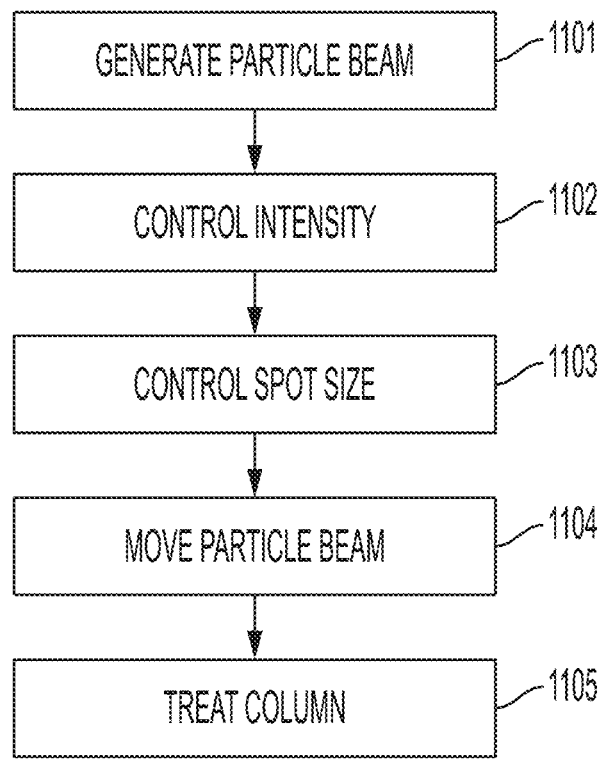
FIG. 11 is a flowchart showing an example process for treating an irradiation target by scanning a particle beam column-by-column across the target.

Referring to FIG. 11, the control system may be configured—for example, programmed—to implement a treatment plan for a target, such as tumor. The treatment plan may specify parameters including the dose rate of particle beam to use such as an ultra-high dose rate, the locations at which the dose is to be delivered to the target, and the sequence at which columns of the target are to be treated. Initially, the control system may control a particle accelerator—in this example, synchrocyclotron 310—to generate (1101) a particle beam having specified parameters, including beam current and intensity. In some implementations, the beam current of the particle beam is 100 nanoamperes (nA) of current or less. In some implementations, the beam current of the particle beam is 50 nA of current or less. Levels of beam current on the order of nanoamperes may reduce risks of injury to the patient, may reduce risks of damage to the accelerator or other electronics in the treatment room, or may reduce risks of both such injury and damage.

The intensity of the particle beam may also be controlled (1102), or modulated, to control or to change the dose applied to the target at different particle beam energies. Thus, intensity-modulated proton therapy (IMPT) may be delivered using the techniques described herein. In some implementations, the same irradiation target may be treated using beams having different or the same intensities from multiple different angles either at FLASH dose rates or at dose rates lower than FLASH dose rates. For example, an irradiation target may be treated at FLASH or non-FLASH dose rates by delivering radiation by columns at different angles. In such examples, because the radiation is delivered at different angles, healthy tissue that is not being treated may be subjected to radiation only once.

The beam intensity is based, at least in part, on the number of particles in the particle beam. For example, the beam intensity may be defined by the number of particles in the particle beam. The intensity of the particle beam may change from spot to spot of the particle beam. Additionally, the intensity of one spot of the particle beam may be independent of the intensity of one or more other spots of the particle beam, including immediately horizontally-adjacent spots or vertically-adjacent spots. Accordingly, in some examples, any spot in a three-dimensional volume may be treated to an arbitrary dose independent of the dose to one or more adjacent spots. The control system may control particle beam intensity using one or more techniques.

In an example technique, the intensity of the particle beam can be controlled by varying the time duration of the pulses of particles obtained from the plasma column. In more detail, the RF voltage sweeps from a starting (e.g., maximum) frequency (e.g., 135 megahertz (MHz)) to an ending (e.g., minimum) frequency (e.g., 90 MHz). The particle source is activated for a period of time during the RF sweep to produce a plasma column. For example, in some implementations, the particle source is activated at 132 MHz for a period of time. During that time, particles are extracted from the plasma column by the electric field produced by the RF voltage. The particles accelerate outwardly in expanding orbits as the RF voltage frequency drops, keeping pace with the decreasing magnetic field and increasing relativistic mass until the particles are swept out at a time (e.g., about 600 microseconds) later. Changing the duration for which the particle source is activated changes the width of the pulse of particles that are extracted from the plasma column during a frequency sweep. Increasing the pulse width causes an increase in the amount of particles extracted and thus an increase in the intensity of the particle beam. Conversely, decreasing the pulse width causes a decrease in the amount of particles extracted and thus a decrease in the intensity of the particle beam.

In another example technique, the intensity of the particle beam can be controlled by changing a voltage applied to cathodes in the particle source. In this regard, the plasma column is generated by applying a voltage to two cathodes of the particle source and by outputting a gas, such as hydrogen ($H_2$), in the vicinity of the cathodes. The voltage applied to the cathodes ionizes the hydrogen and the background magnetic field collimates the ionized hydrogen to thereby produce the plasma column. Increasing the cathode voltage causes an increase in the amount of ions in the plasma column and decreasing the cathode voltage causes a decrease in the amount of ions in the plasma column. When more ions are present in the plasma column, more ions can be extracted during the RF voltage sweep, thereby increasing the intensity of the particle beam. When fewer ions are present in the plasma column, fewer ions can be extracted during the RF voltage sweep, thereby decreasing the intensity of the particle beam.

In another example technique, the intensity of the particle beam can be controlled by varying the amount of hydrogen supplied to the particle source. For example, increasing the amount of hydrogen supplied to the particle source results in more opportunity for ionization in the plasma column in response to the cathode voltage. Conversely, decreasing the amount of hydrogen supplied to the particle source results in less opportunity for ionization in the plasma column in response to the cathode voltage. As noted above, when more particles are present in the plasma column, more particles are extracted during the RF voltage sweep, thereby increasing the intensity of the particle beam. When fewer particles are present in the plasma column, fewer particles are extracted during the RF voltage sweep, thereby decreasing the intensity of the particle beam.

In another example technique, the intensity of the particle beam can be controlled by varying the magnitude of the RF voltage used to extract particles from the plasma column. For example, increasing the magnitude of the RF voltage causes more particles to be extracted from the plasma column. Conversely, decreasing the magnitude of the RF voltage causes fewer particles to be extracted from the plasma column. When more particles are extracted, the particle beam has a greater intensity than when fewer particles are extracted.

In another example technique, the intensity of the particle beam can be controlled by varying the starting time during the frequency sweep at which the particle source is activated and, thus, during which particles are extracted. More specifically, there is a finite window during the frequency sweep during which particles can be extracted from the plasma column. In an example implementation, the frequency sweeps from about 135 MHz to about 90 MHz at a substantially constant rate. In this example, particles can be extracted at about the beginning of the downward slope between starting and ending frequencies, e.g., between 132 MHz and 131 MHz respectively, and the particle source can be activated for a period of time, e.g., for about 0.1 microseconds (µs) to 100 µs (e.g., 1 µs to 10 µs or 1 µs to 40 µs). Changing the frequency at which the particle source is activated affects the amount of particles that are extracted from the particle beam and therefore the intensity of the particle beam.

In another example technique, pulse blanking may be used to control the intensity of the particle beam. In this regard, the RF frequency sweep is repeated a number of times per second (e.g., 500 times/second). The particle source could be activated for each frequency sweep (e.g., every 2 ms). Pulse blanking reduces the number of particles extracted from the particle beam by not activating the particle source during every frequency sweep. To achieve maximum beam intensity, the particle source may be activated every frequency sweep. To reduce beam intensity, the particle source may be activated less frequently, e.g., every second, third, hundredth, etc. sweep.

In another example technique, the intensity of the particle beam can be controlled by applying a DC bias voltage to one or more dees used to apply the RF voltage to the particle accelerator cavity. In this regard, the particle accelerator includes an active dee plate that is a hollow metal structure having two semicircular surfaces that enclose a space in which the protons are accelerated during their rotation around the cavity enclosed by the magnet yokes. The active dee is driven by an RF signal that is applied at the end of an RF transmission line to impart an electric field into the space. The RF field is made to vary in time as the accelerated particle beam increases in distance from the geometric center. A dummy dee may include a rectangular metal wall with a slot that is spaced near to the exposed rim of the active dee. In some implementations, the dummy dee is connected to a reference voltage at the vacuum chamber and magnet yoke.

Applying RF voltage in the presence of a strong magnetic field can cause multi-pactoring, which can reduce the magnitude of the RF field and, in some cases, cause an electrical short. To reduce the amount of multi-pactoring, and thereby maintain the RF field, DC (direct current) bias voltage may be applied to the active dee and, in some implementations, also to the dummy dee. In some implementations, the differential DC bias voltage between the active dee and dummy dee may be controlled to reduce multi-pactoring and thereby increase beam intensity. For example, in some implementations, there may be a 50% differential between the DC bias voltage on the active dee and dummy dee. In an example implementation, there is a −1.9 KV DC bias voltage applied to the dummy dee and there is a −1.5 KV DC bias voltage be applied to the active dee.

In another example technique, the intensity of the particle beam can be controlled by controlling the rate at which the RF voltage is swept—for example, the slope of the decrease. By decreasing the slope, it is possible to increase the amount of time during which particles can be extracted from the plasma column. As a result, more particles can be extracted, thereby increasing the intensity of the particle beam. The converse is also true, e.g., by increasing the slope, the amount of time during which particles can be extracted from the plasma column can be decreased, which can result in a decrease in particle beam intensity.

Implementations of the foregoing techniques for controlling the particle beam intensity are described in U.S. Pat. No. 9,723,705 entitled "Controlling Intensity Of A Particle Beam", the contents of which are incorporated herein by reference.

The control system may also control (1103) the spot size of the particle beam. As indicated above, one or more scattering devices may be moved into the path of the particle beam to change its spot size. In some implementations, the native spot size of the synchrocyclotron is the smallest spot size that is produced by the system. Since beam intensity is also a function of spot size, this spot size also produces the greatest beam intensity. In some implementations, the spot size that is producible by the system is less than 2 millimeters (mm) sigma. In some implementations, the spot size that is producible by the system is at least 2 mm sigma. In some implementations, the spot size that is producible by the system is between 2 mm sigma and 20 mm sigma. In some implementations, the spot size that is producible by the system is greater than 20 mm sigma. In some implementation, operation 1103 may be omitted.

The control system controls (1104) the scanning magnet to move the particle beam in accordance with the treatment plan to a path 24 through target 21, as shown in FIG. 2 for example. Controlling the scanning magnet may include controlling the current through the coils of the scanning magnet (FIGS. 6 and 7) that control movement of the particle beam in the Cartesian X dimension, controlling the current through coils of the scanning magnet that control movement of the particle beam in the Cartesian Y dimension, or both. At that location, the system delivers an ultra-high dose rate of radiation to a column that extends along the beam path through the target. In this example, the column includes interior portions of the target that are located along a direction 29 of the particle beam (FIG. 2). Column 25 is three dimensional in that it extends radially from the center of the beam spot to a perimeter of the spot and the column extends downward through the target. In some implementations, the column extends through the entirety of the target as shown in FIG. 2. In some implementations, the column extends only part-way through the target. In some implementations the column is entirely within an interior of the target. In some implementations, the column starts at one surface of the target and extends to an interior of the target but does not reach the other surface of the target. In some implementations, parts of adjacent columns overlap.

The column is treated (1105) using an ultra-high dose rate of radiation. Examples of ultra-high dose rates of radiation are described herein and include, but are not limited to, 1 Gray-per-second or more for a duration of less than 5 s. The control system controls the energy of the particle beam while the particle beam is stationary so that the particle beam treats the column in the target. Treating the column in the target includes changing the energy of the particle beam so that, for each change in energy a majority of a dose of protons in the particle beam (its Bragg peak) deposits at a different depth within the target. As described herein, the energy of the particle beam may be changed by moving structures, which may be made of boron carbide or other particle energy degrading material, into or out of the path of the particle beam, as described with respect to the examples of FIGS. 12 to 19 and 35 to 44. All or some of the operations of FIG. 11 may be repeated to treat different columns on an irradiation target. For example operations 1102, 1103, 1104, and 1105 may be repeated for each column to be treated on an irradiation target.

Figure 12:
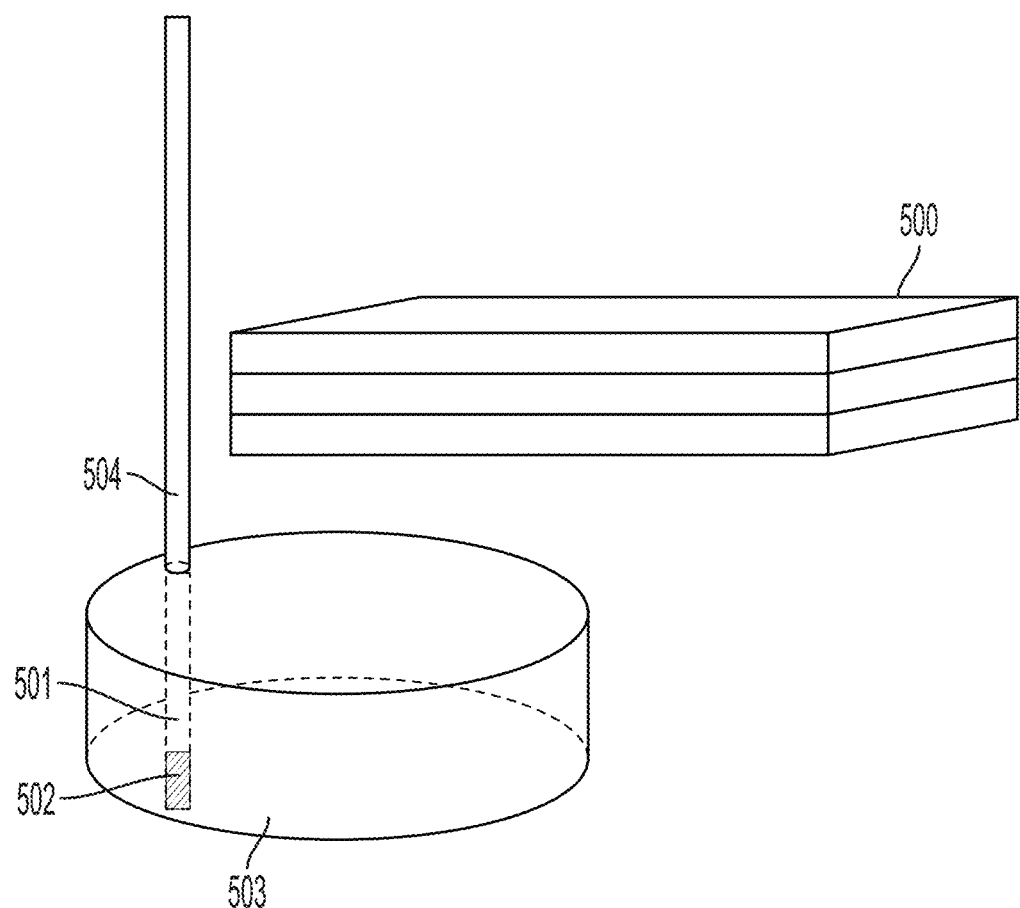
FIGS. 12, 13, 14, and 15 are perspective block diagrams illustrating treatment of a column of an irradiation target by moving energy-absorbing plates sequentially into a path of a stationary particle beam.

In implementations described below that use a variable-energy synchrocyclotron (or other type of variable energy particle accelerator), the energy of the particle beam may be changed by changing the current through the main coils of the synchrocyclotron. In some implementations, the energy of the particle beam is changed by moving structures, such as the energy-absorbing plates of range modulator 460, into and out of the path of the particle beam. In this regard, since the treatment plan specifies the locations of the columns on the target, the energy-absorbing plates of the range modulator may be pre-positioned proximate to those locations so as to reduce the time it takes for those plates to move into and out of position. Referring to FIG. 12, for example, plates 500—which may be made from pure boron carbide or a boron carbide-graphite composite, for example—may be positioned proximate to column 501 in target 503 before treatment of column 501 with radiation begins. The plates may be moved from that location into the particle beam, thereby reducing the distance that the plates need to travel. That is, plates 500 may be configured to retract fully into the range modulator. The plates may be extended partially or fully prior to treatment and, as a result, need not travel from their fully retracted position in order to reach the path of the particle beam.

One or more of the plates may be controlled to move into and out of the path of the particle beam to change the energy of the particle beam, as noted. In an example, each of the one or more plates is movable into or out of the path of the particle beam in a duration of 100 ms or less. In an example, each of the one or more plates is movable into or out of the path of the particle beam in a duration of 50 ms or less. In an example, each of the one or more plates is movable into or out of the path of the particle beam in a duration of 10 ms or less. In an example, each of the one or more plates is movable into or out of the path of the particle beam in a duration of 20 ms or less or in a duration of 10 ms or less. Use of linear motors, as described previously, may promote rapid movement of the plates, although electrical motors may be used as well. In this example, rapid movement includes movement on the order of tens of milliseconds.

Figure 13:
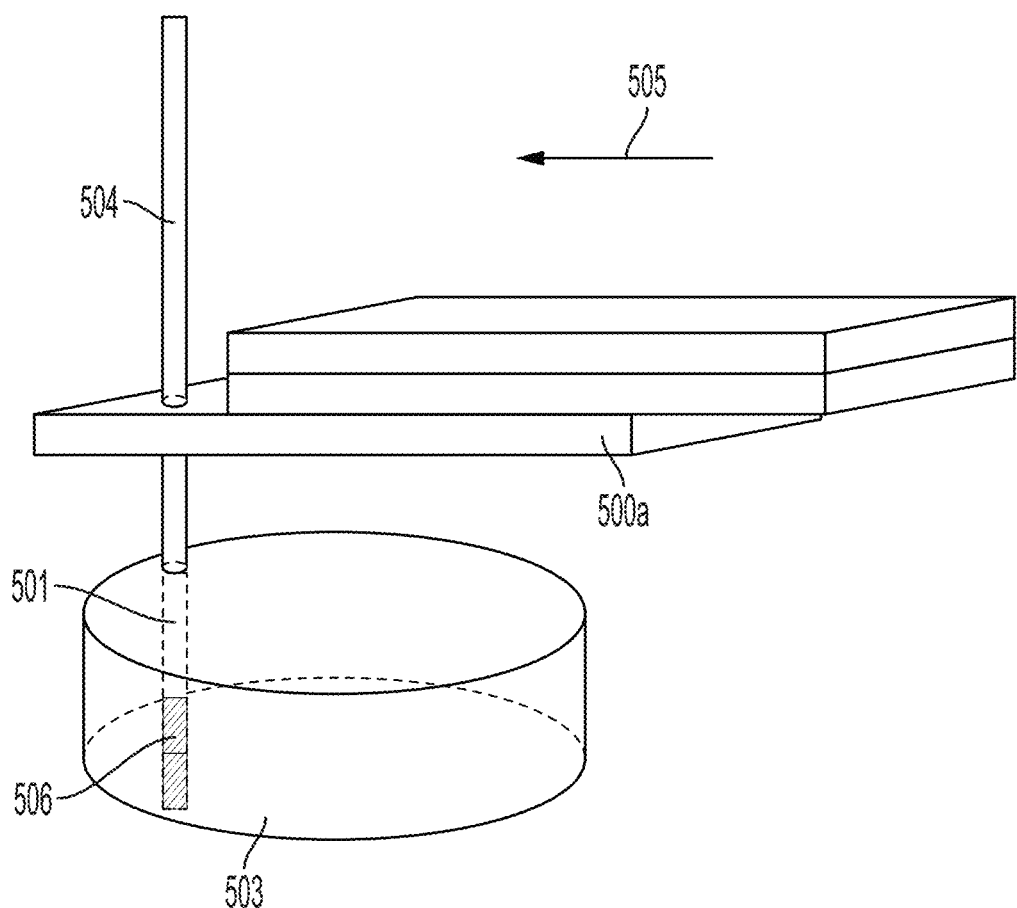
Figure 14:
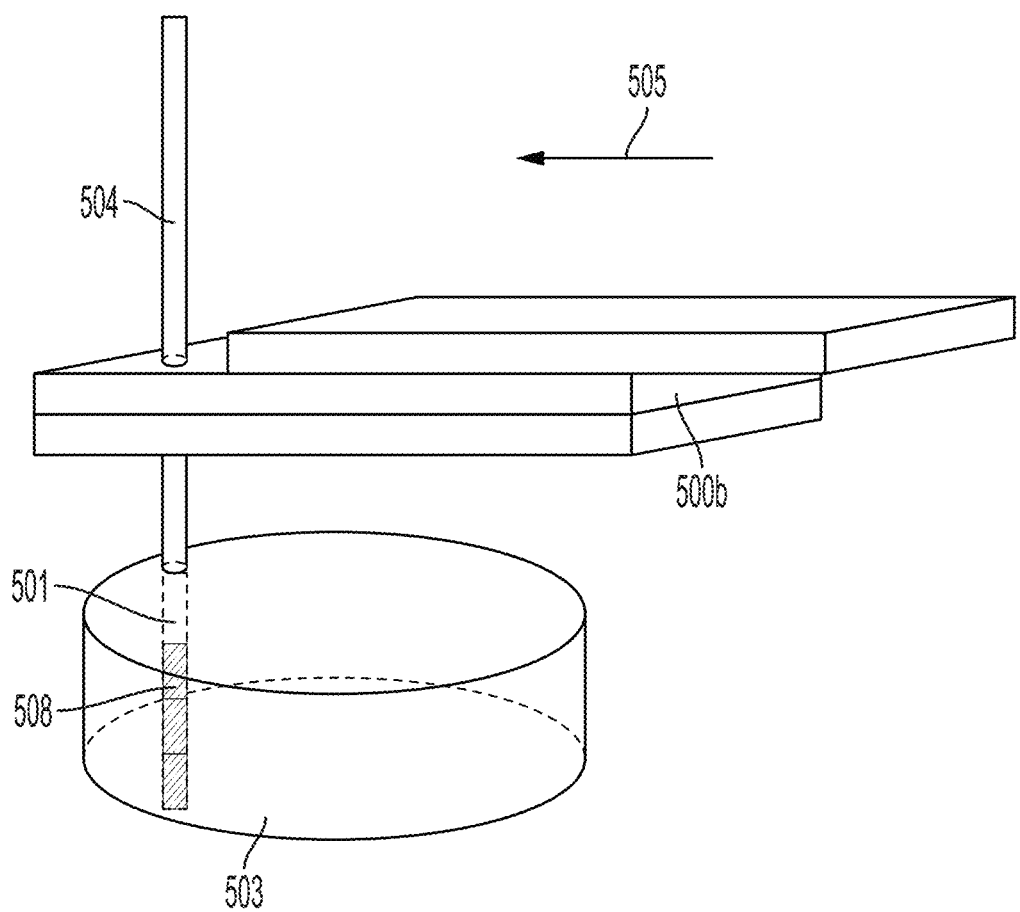
Figure 15:
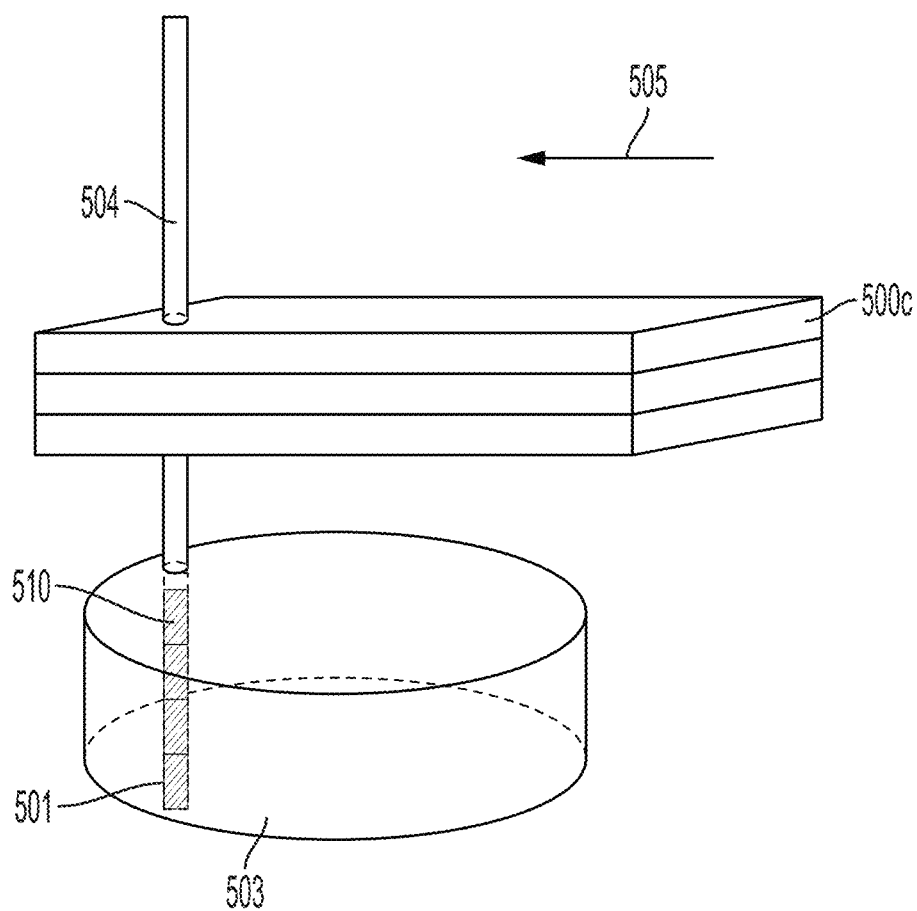

One or more of the plates may be moved into and out of the path of the particle beam based on sequences defined in the treatment plan. For example, referring to FIGS. 12, 13, 14, and 15, a particle beam 504 is positioned by the scanning system to treat column 501 of target 503 at an ultra-high dose rate. In this example, to treat progressively shallower portions of column 501, treatment initially is performed with no plate in the path of the particle beam. This is shown in FIG. 12. The deepest part 502 of column 501 therefore is treated. In FIG. 13, plate 500a proceeds into the path of particle beam 504 along the direction of arrow 505 to reduce the energy of the particle beam. In this plate configuration, the second deepest part 506 of column 501 is treated. In FIG. 14, plate 500b also proceeds into the path of particle beam 504 along the direction of arrow 505 to reduce further the energy of the particle beam. In this plate configuration, the third deepest part 508 of column 501 is treated. In FIG. 15, plate 500c also proceeds into the path of particle beam 504 along the direction of arrow 505 to reduce further the energy of the particle beam. In this plate configuration, the shallowest part 510 of column 501 is treated. By changing the energy of particle beam 504 while particle beam 504 is stationary, the entirety of column 501 may be delivered ultra-high dose rate radiation. Examples of ultra-high dose rates are provided herein.

Figure 16:
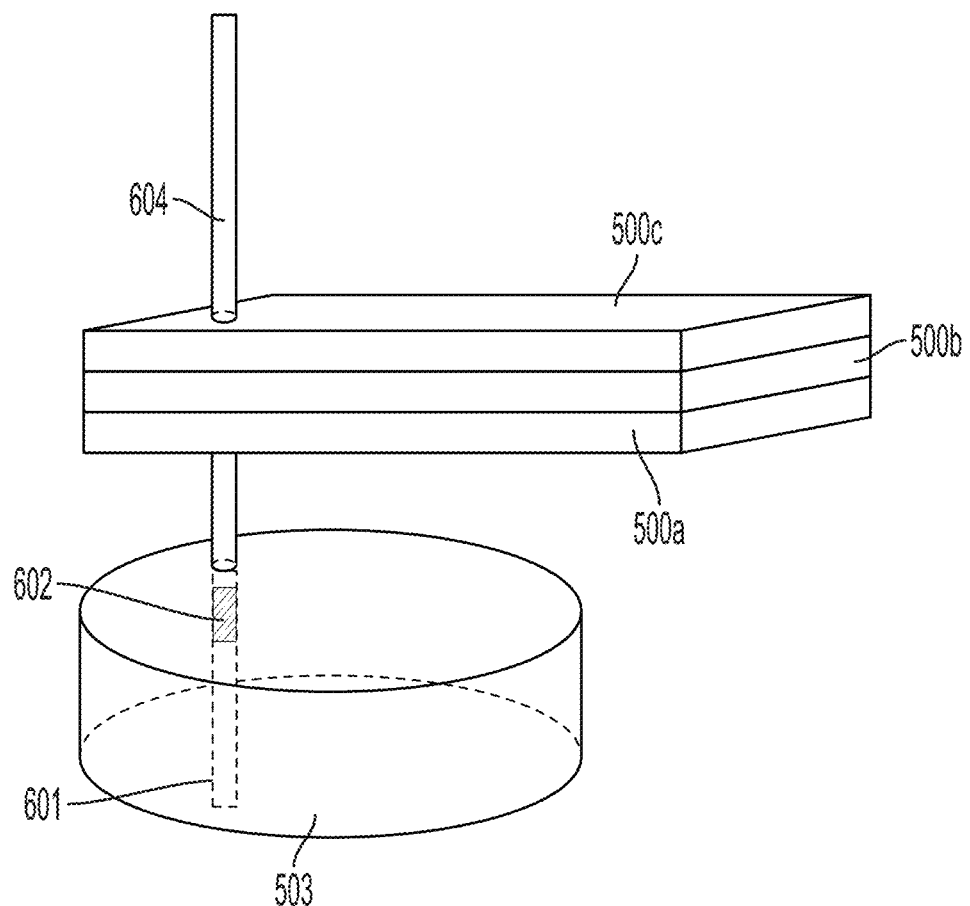
FIGS. 16, 17, 18, and 19 are perspective block diagrams illustrating treatment of a column of an irradiation target by moving energy-absorbing plates sequentially out of a path of a stationary particle beam.
Figure 17:
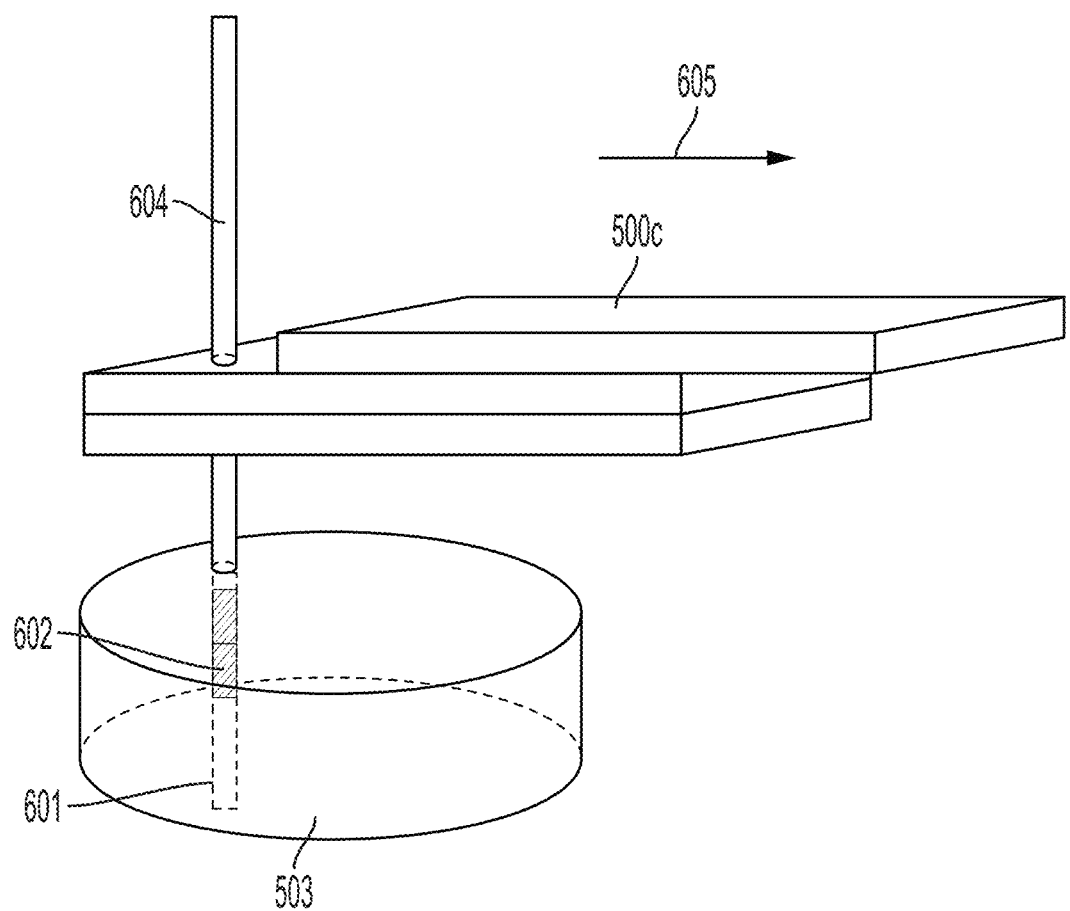
Figure 18:
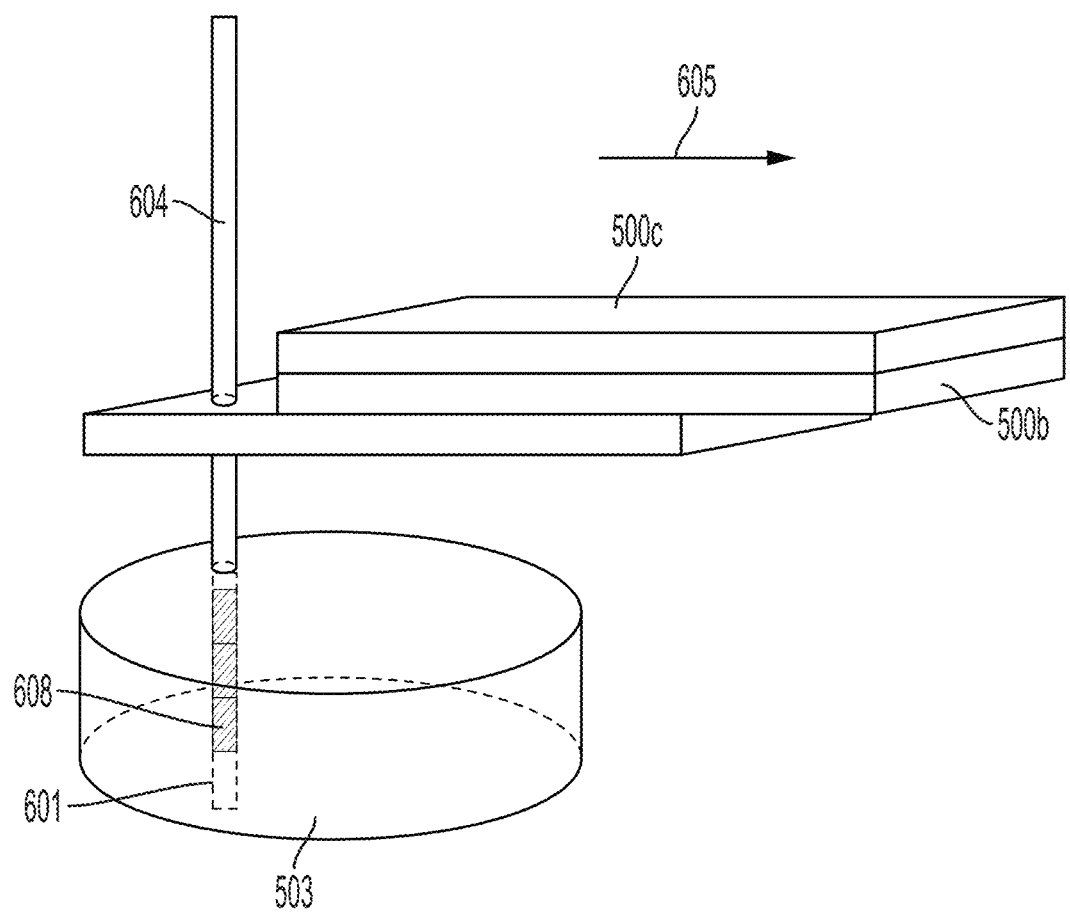
Figure 19:
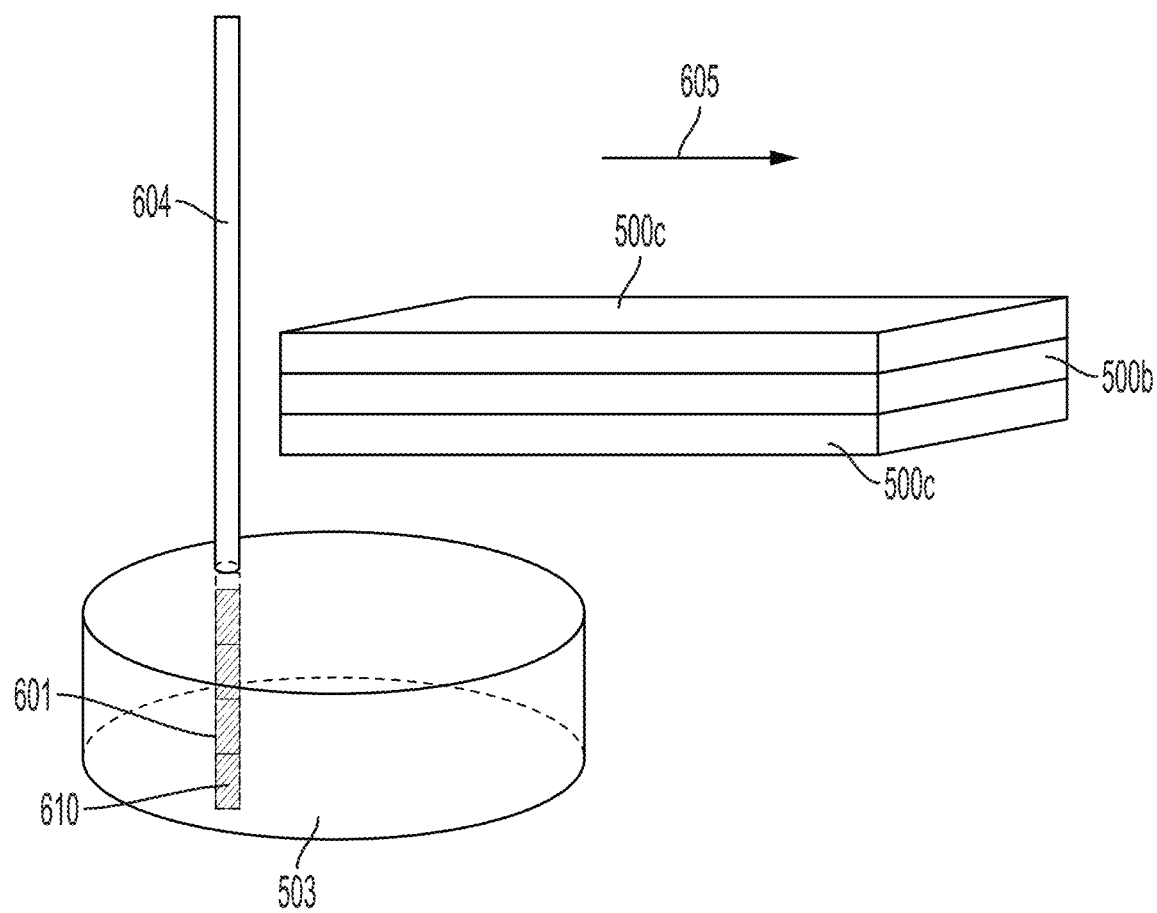

The particle beam may be directed by the scanning magnet to a new path through the target to treat a different column of target 503. The different column may be immediately adjacent to column 501 or may not be immediately adjacent to column 501. In some implementations, spots of the beam may overlap in part or not. For example, referring to FIGS. 16, 17, 18, and 19, a particle beam 604 is positioned by the scanning system to treat column 601 of target 503 at an ultra-high dose rate. In this example, to treat progressively deeper portions of column 601, treatment initially is performed with all plates 500a, 500b, and 500c in the path of the particle beam. This is shown in FIG. 16. The shallowest part 602 of column 601 therefore is treated first. In FIG. 17, plate 500c moves out of the path of particle beam 604 along the direction of arrow 605 to increase the energy of the particle beam. In this plate configuration, the second shallowest part 602 of column 601 is treated. In FIG. 18, plate 500b also moves out of the path of particle beam 604 along the direction of arrow 605 to increase further the energy of the particle beam. In this plate configuration, the third shallowest part 608 of column 601 is treated. In FIG. 19, plate 500c also moves out of the path of particle beam 604 along the direction of arrow 605 to increase further the energy of the particle beam. In this plate configuration, the deepest part 610 of column 601 is treated. By changing the energy of particle beam 604 while particle beam 604 is stationary, the entirety of column 601 may be delivered ultra-high dose rate radiation.

In some implementations, the plates need not be sequenced in order to treat a column. For example, plate 500a could be moved into the path of the particle beam first, followed by plate 500c, followed by plate 500b.

During delivery of ultra-high dose rate radiation to column 501 or 601, the intensity of particle beam 504 or 604 may be changed as necessary in order to deliver the ultra-high dose rate radiation specified in the treatment plan. Notably, the particle beam is stationary during delivery of the ultra-high dose rate radiation to each column. For example, while the ultra-high dose rate radiation is being delivered to different depths within the column, the path of the particle beam does not change relative to the target and the particle beam does not move. After the ultra-high dose rate radiation is delivered to the column, the particle beam is directed on a new path through the target. An ultra-high dose rate of radiation is then applied at that new path in the same manner as described with respect to FIG. 11. This process is repeated until all of the target is treated using the ultra-high dose rate radiation or until a designated part of the target is treated using the ultra-high dose rate radiation. In some implementations, the columns may be parallel as shown in the figures, with some or no overlap. In some implementations, at least some of the columns may not be in parallel resulting in overlap. In some implementations, sets of columns may be applied to the same target or microvolume from different angles, thereby treating the target multiple times with radiation while preventing healthy tissue from being impacted by radiation more than once.

In some implementations, the particle beam is never again directed along paths that have already been treated using the ultra-high dose rate radiation. For example, the particle beam steps from path to path through target 503. In this example, each column extending into the target along a path is treated using the ultra-high dose rate radiation only once. Columns are not revisited and treated again. By treating columns only once using ultra-high dose rate radiation, healthy tissue above, and in some cases below, the target is less susceptible to damage from the radiation. Notably, however, the example systems described herein are not limited to treating each column only once using the ultra-high dose rate radiation. For example, in some implementations, each column may be revisited any appropriate number of times and subjected to one or more additional doses of ultra-high dose rate radiation. Furthermore, the example systems described herein are not limited to treating each column using only ultra-high dose rate radiation. For example, columns of a target may be treated as described herein using dose rates of radiation that are less than what would be considered an ultra-high dose rate. For instance, columns of a target may be treated as described herein using dose rates of radiation such as 0.1 Gray-per-second for a duration of one or more minutes. In some implementations, column-by-column treatment such as that shown in FIG. 2 may be combined with layer-by-layer treatment such as that shown in FIG. 1. For example, the target may be treated column-by-column followed by layer-by-layer or treated layer-by-layer followed by column-by-column. In some implementations, part of the target may be treated column-by-column and part of the target may be treated layer-by-layer in each case with ultra-high dose rate radiation or less.

In some implementations, energy-absorbing plates of the range modulator may be sequenced differently for different columns on the target in order to reduce treatment time. For example, for a column 501, the plates may be moved sequentially into the particle beam as explained with respect to FIGS. 12 to 15. Then, the particle beam may be directed to treat an adjacent—or other—column 601 of the target. If the plates already cover that path of the particle beam, they may be moved sequentially out of the path of the particle beam as described with respect to FIGS. 16 to 19. If the plates do not already cover that path of the particle beam, the plates may be moved together to cover that path of the particle beam and then moved sequentially out of the path of the particle beam. Accordingly, for a first column, the plates may be moved sequentially to treat progressively shallower portions—for example, layers—of the first column. For a second column that is adjacent to the first column, the plates may be moved sequentially to treat successively deeper portions—for example, layers—of the second column. This process may be repeated throughout the target for adjacent paths of the particle beam. In some implementations, movements of the plates may be incremental in the beam field; for example, based on the spot size (e.g., on the order of millimeters) rather than from their fully retracted position. For example, the plates may be moved from particle beam path to adjacent particle beam path rather than being fully retracted and extended for each column.

In some implementations, the energy-absorbing plates are movable across all or part of the beam field. In some examples, the beam field is the maximum extent that the beam can be moved across a plane parallel to the treatment area on a patient. One or more of the plates may track the particle beam as it moves from particle beam to adjacent particle beam. For example, one or more of the plates may move along with movement of the particle beam such that the particle beam passes through one or more of the plates while the plates move.

In some implementations, a dose of radiation that is less than an ultra-high (or FLASH) dose rate of radiation may be applied to the target layer-by layer using an energy degrader having structures such as plates, polyhedra, or curved three-dimensional shapes that are made of boron carbide. For example, referring to FIG. 1, an entire layer 10 of a target 11 may be treated using a particle beam 12 having an energy sufficient to deliver dose to layer 10 by moving the particle beam across the layer along the directions of arrows 15. The energy degrader may then be reconfigured—for example, a plate made of boron carbide may be moved out of the beam path to increase an energy level of the particle beam. Then a different layer 16 of the target 11 may be treated in the same manner using a particle beam having a different energy sufficient to deliver dose to layer 16, and so on.

In some implementations, FLASH doses of radiation may be delivered along a single column, with the beam direction fixed at a single spot at an isocenter of the particle accelerator. In some implementations, FLASH doses of radiation may be delivered using slightly larger localized volumes—referred to as micro-volumes—rather than columns aimed at a single spot. A micro-volume may be a voxel, part of a voxel, or include multiple voxels as specified in the treatment plan. FIGS. 35 to 44 show an example of delivery of radiation by column using FLASH dose rates to micro-volumes of an irradiation target. Examples of FLASH dose rates are described herein. In some implementations, delivery of radiation by column to the micro-volumes of FIGS. 35 to 44 may be at non-FLASH dose rates or combined FLASH dose rates and non-FLASH dose rates.

Figure 35:
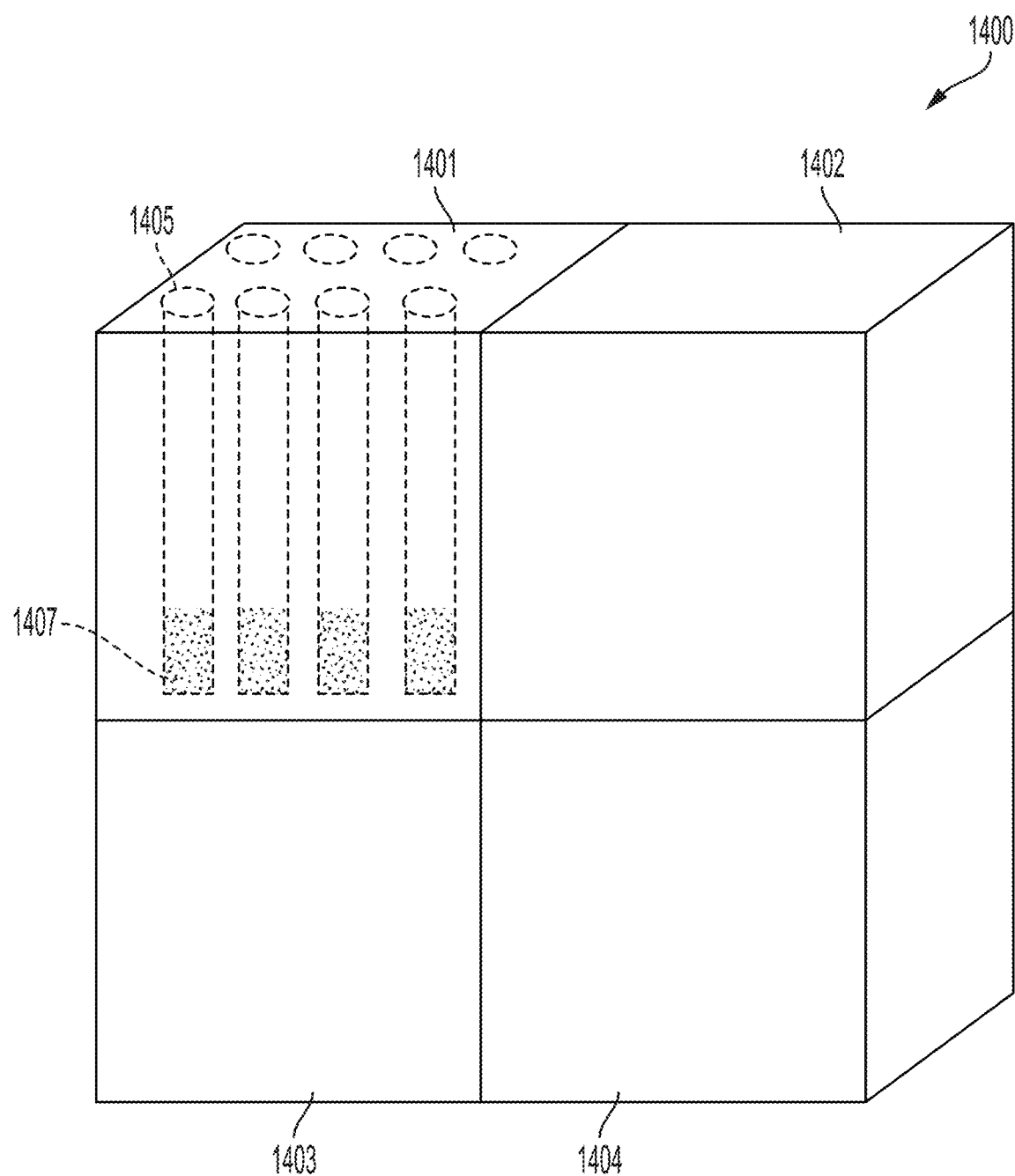
FIGS. 35 to 44 are perspective block diagrams illustrating example processes for treating columns of an irradiation target by micro-volume.

FIG. 35 shows an example of part 1400 of an irradiation target, such as a tumor in a patient. Part 1400 is broken into four micro-volumes 1401, 1402, 1403, and 1404. Although cubical micro-volumes are shown, the micro-volumes may have any appropriate shape, such as three-dimensional orthotopes, regular curved shapes, or amorphous shapes. In this example, each micro-volume is treated through delivery of radiation by column in the manner described herein, for example with respect to FIGS. 12 to 19. For example, column depths of a micro-volume may be treated with radiation by using energy degrader plates to change the beam energy or by controlling a variable-energy synchrocyclotron to change the beam energy. After an individual micro-volume has been treated, the next micro-volume is treated, and so forth until the entire irradiation target has been treated. Treatment of the micro-volumes may be in any appropriate order or sequence.

In the example of FIGS. 35 to 46, only eight columns 1405 are shown. However, any appropriate number of columns may be treated per micro-volume. In some examples 10 to 20 spots, and thus columns, may treat a micro-volume. In addition, although each spot corresponds to a column of radiation, only the front columns are shown in the figures for clarity. Furthermore, although the example described herein treats the micro-volumes from the most deep part of the column to the most shallow part of the column, that need not be the case. For example, energy degrader plates may be controlled to treat one micro-volume from the most deep part of columns to the most shallow part of the columns and then treat the neighboring micro-volume from the most shallow part of the columns to the most deep part of the columns and so forth, as described with respect to FIGS. 12 to 19. In other examples, different column depths may be treated non-sequentially.

Figure 36:
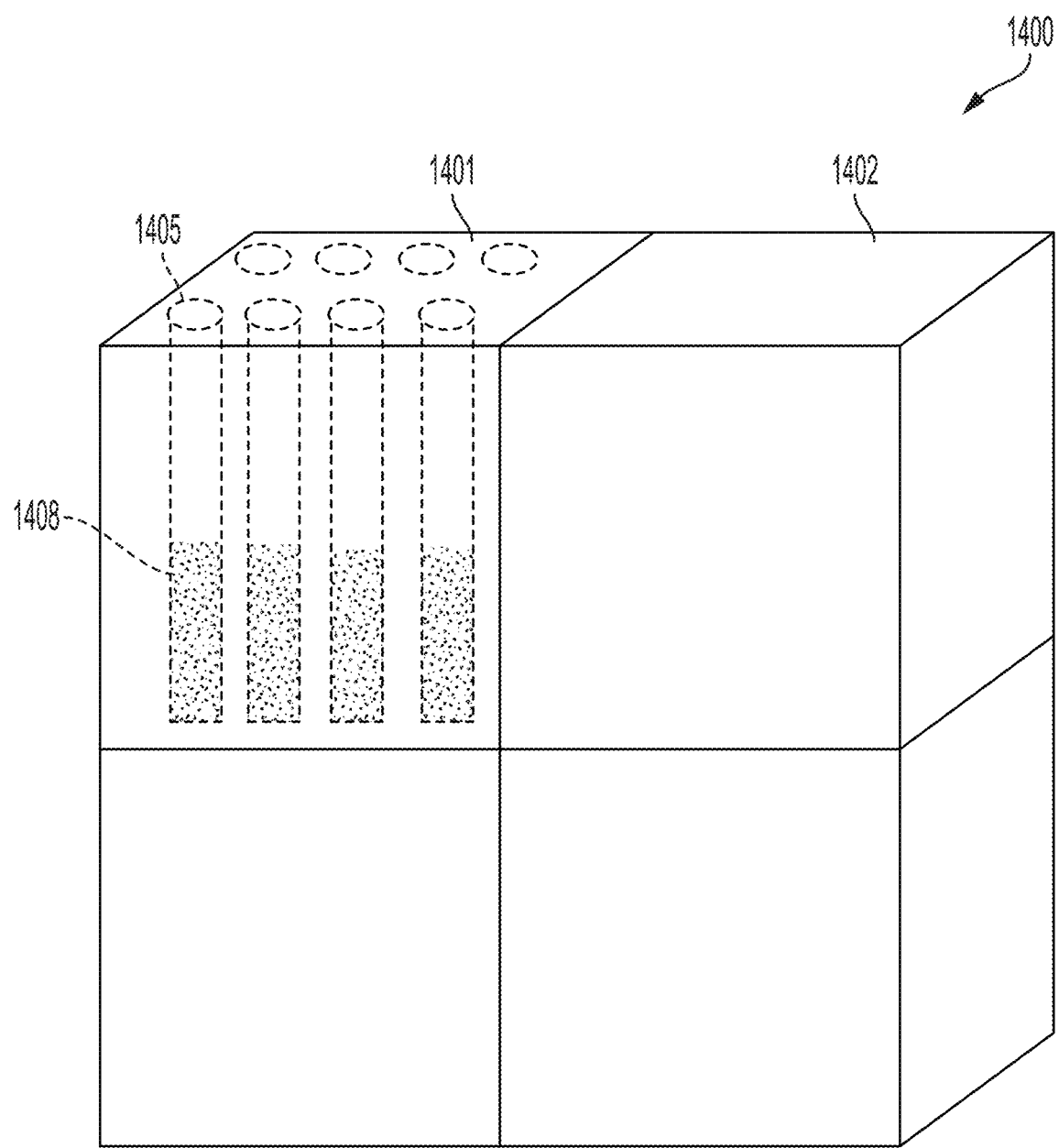
Figure 37:
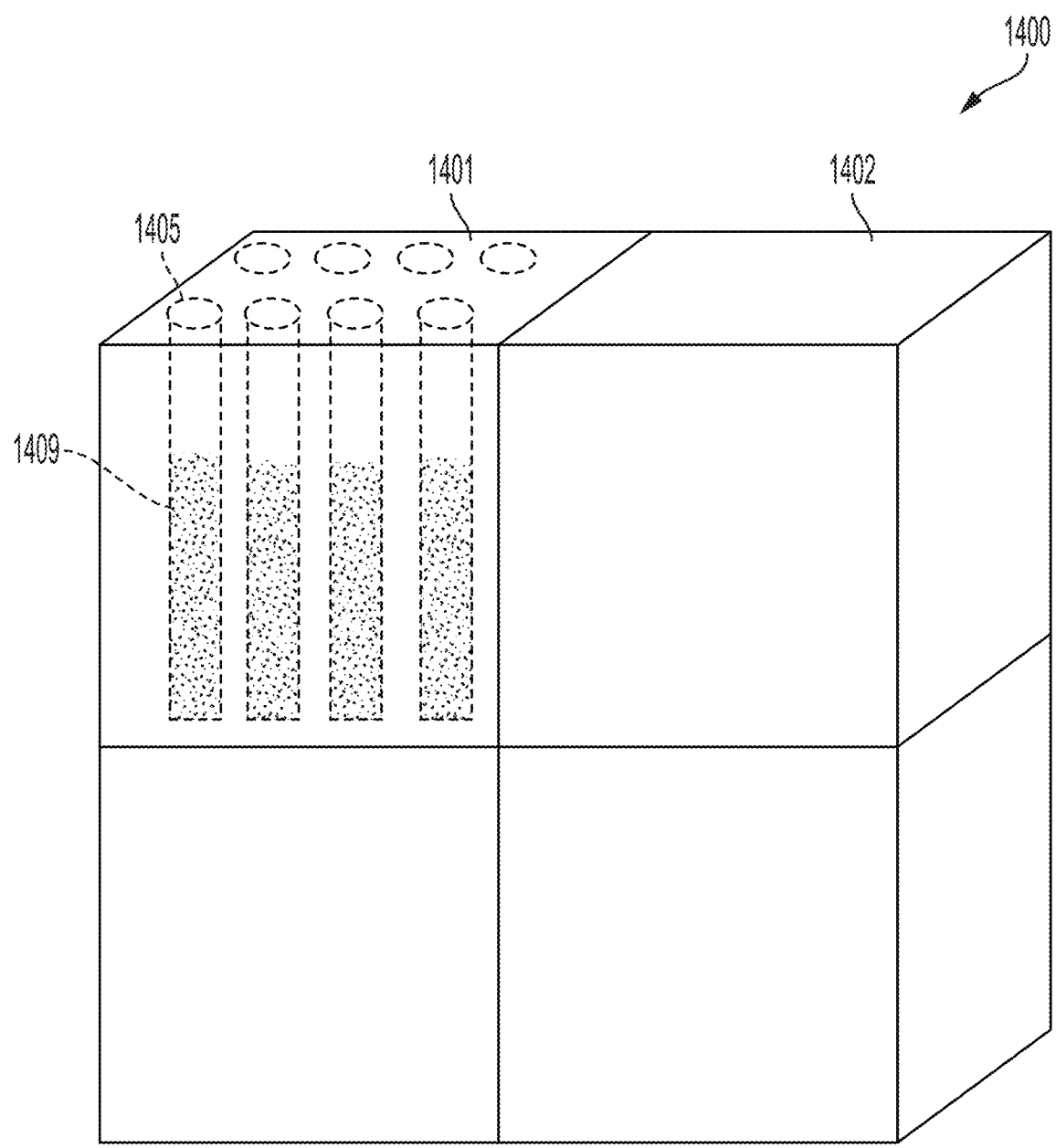
Figure 38:
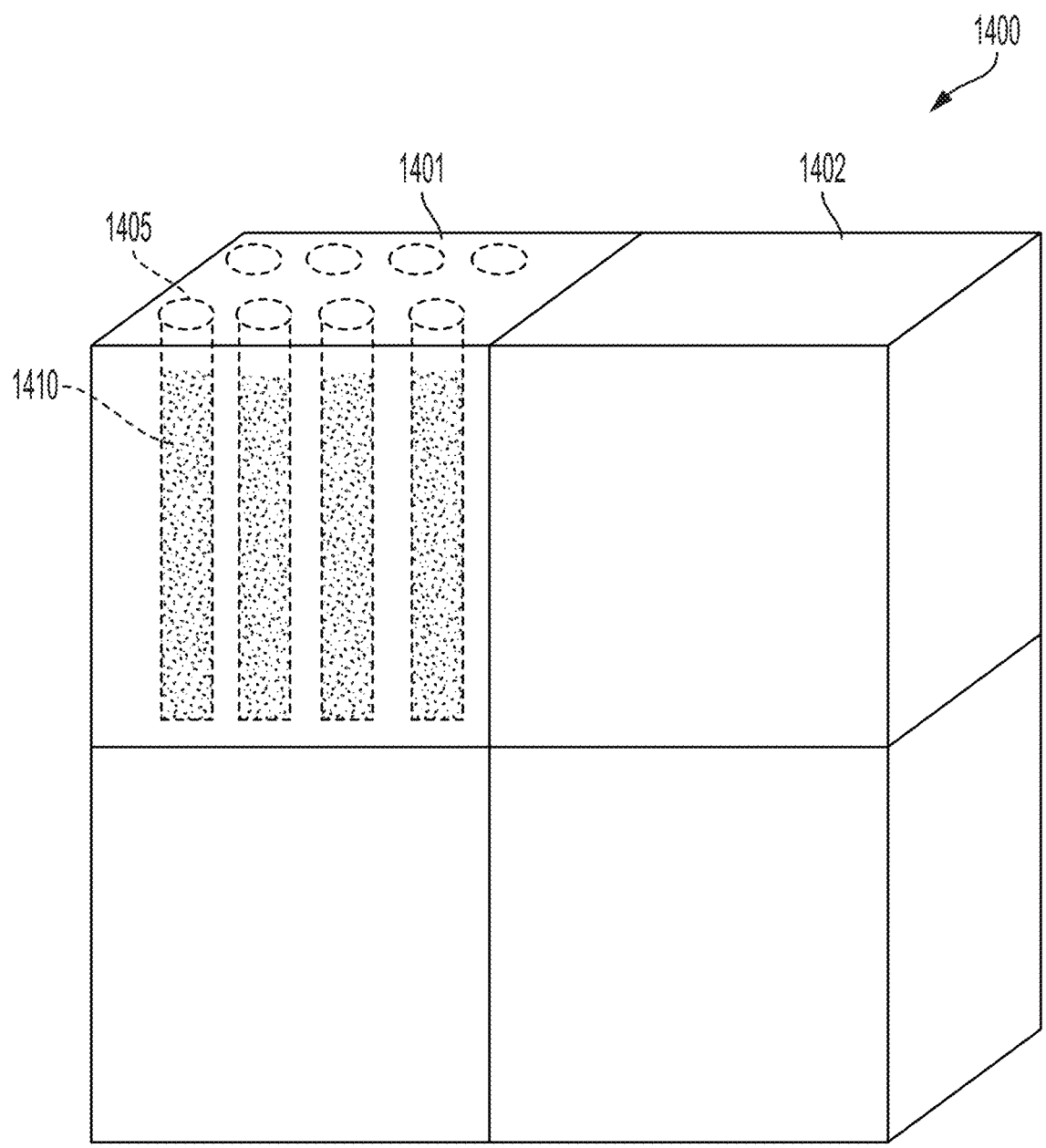
Figure 39:
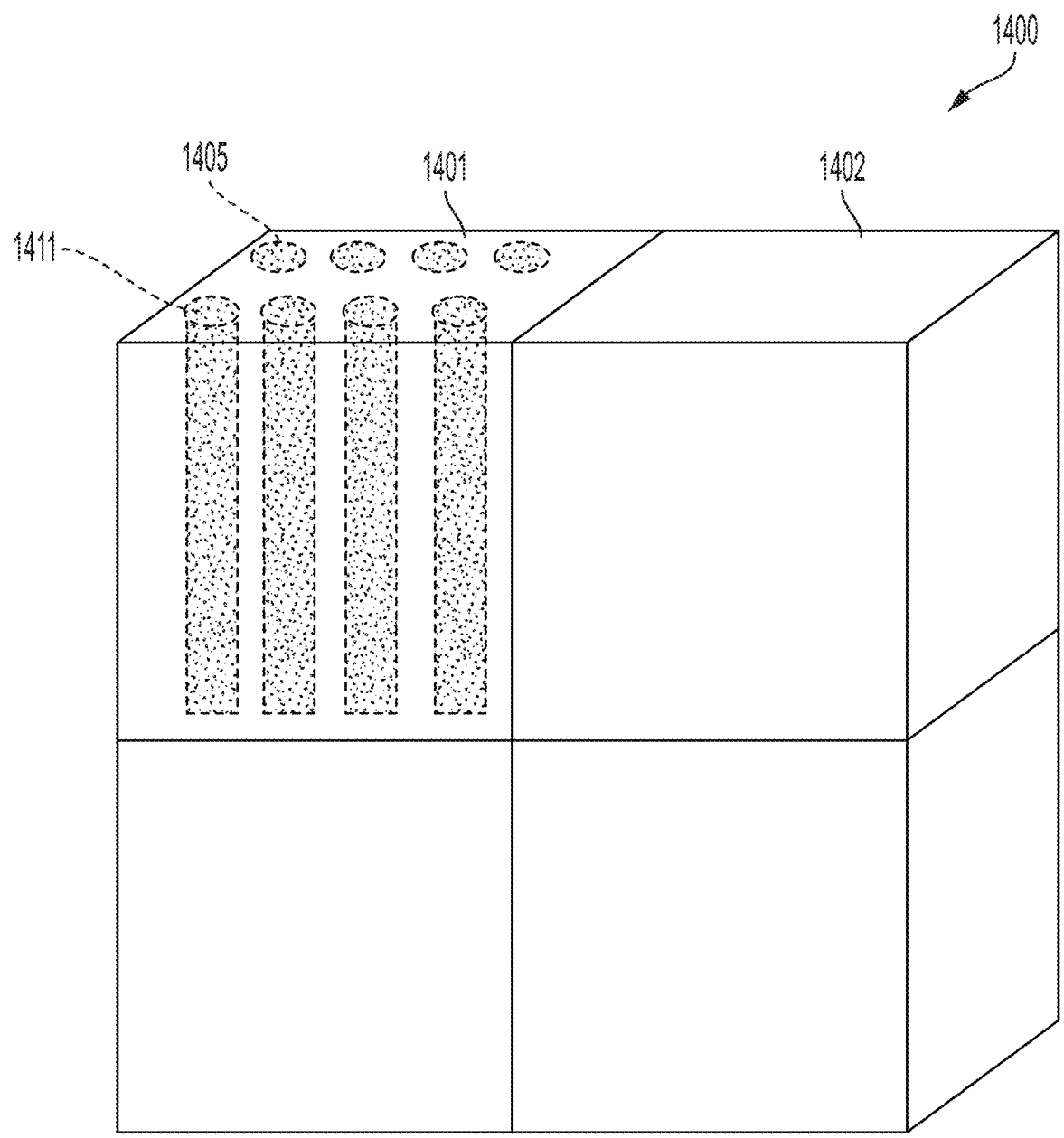

In FIG. 35, the deepest parts 1407 of columns 1405 are treated. Treated parts of the columns are shaded and untreated parts are not shaded, as is the convention herein. In FIG. 36, the next deepest parts 1408 of columns 1405 are treated. In FIG. 37, the next deepest parts 1409 of columns 1405 are treated. In FIG. 38, the next deepest parts 1410 of columns 1405 are treated. In FIG. 39, the shallowest parts 1411 of columns 1405 are treated, thereby completing treatment of micro-volume 1401. In this regard, although the columns are separated for clarity, the columns may actually overlap at least in part as is the case with respect to FIGS. 12 to 19 to ensure that the entire micro-volume is treated with radiation.

Figure 40:
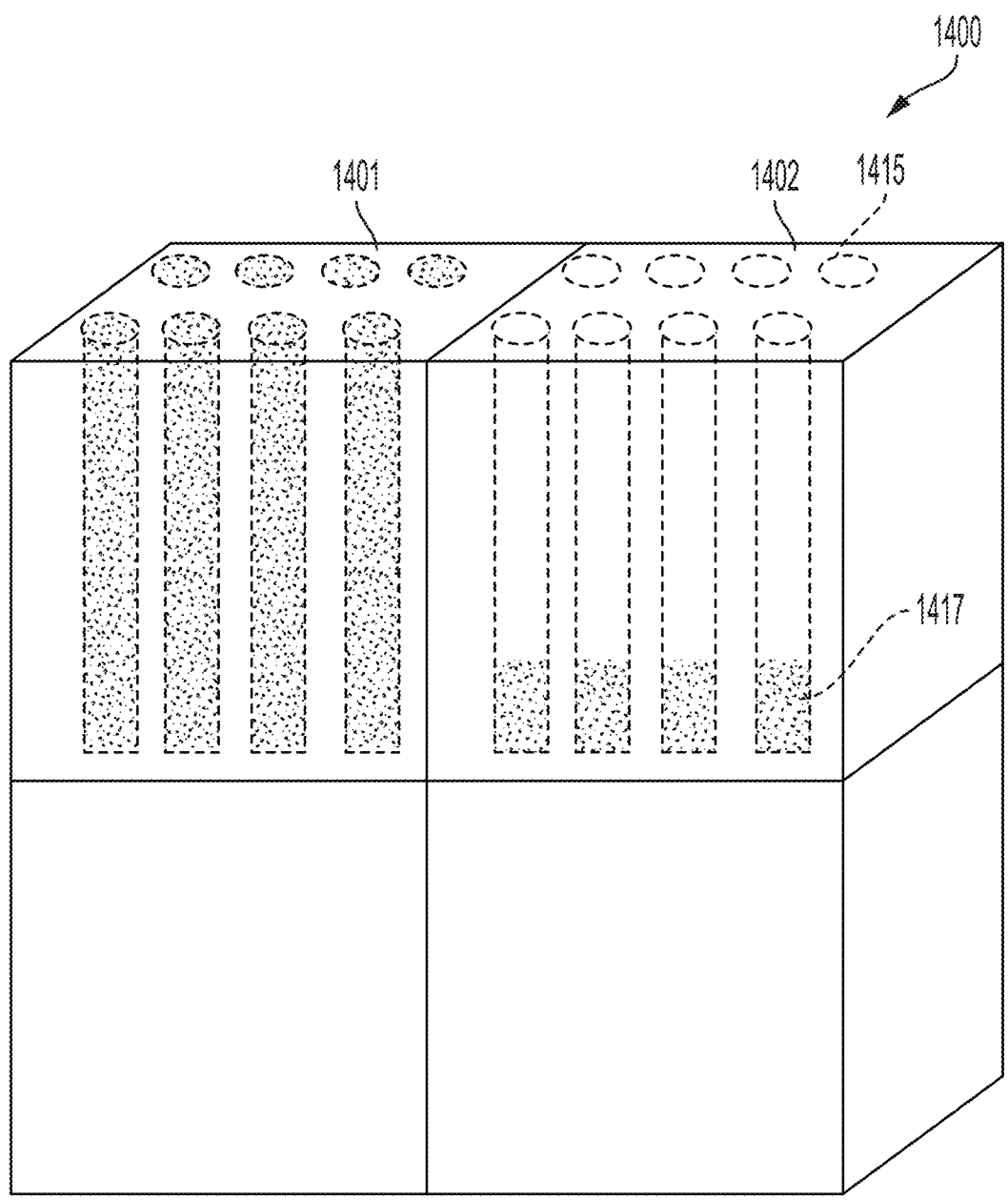
Figure 41:
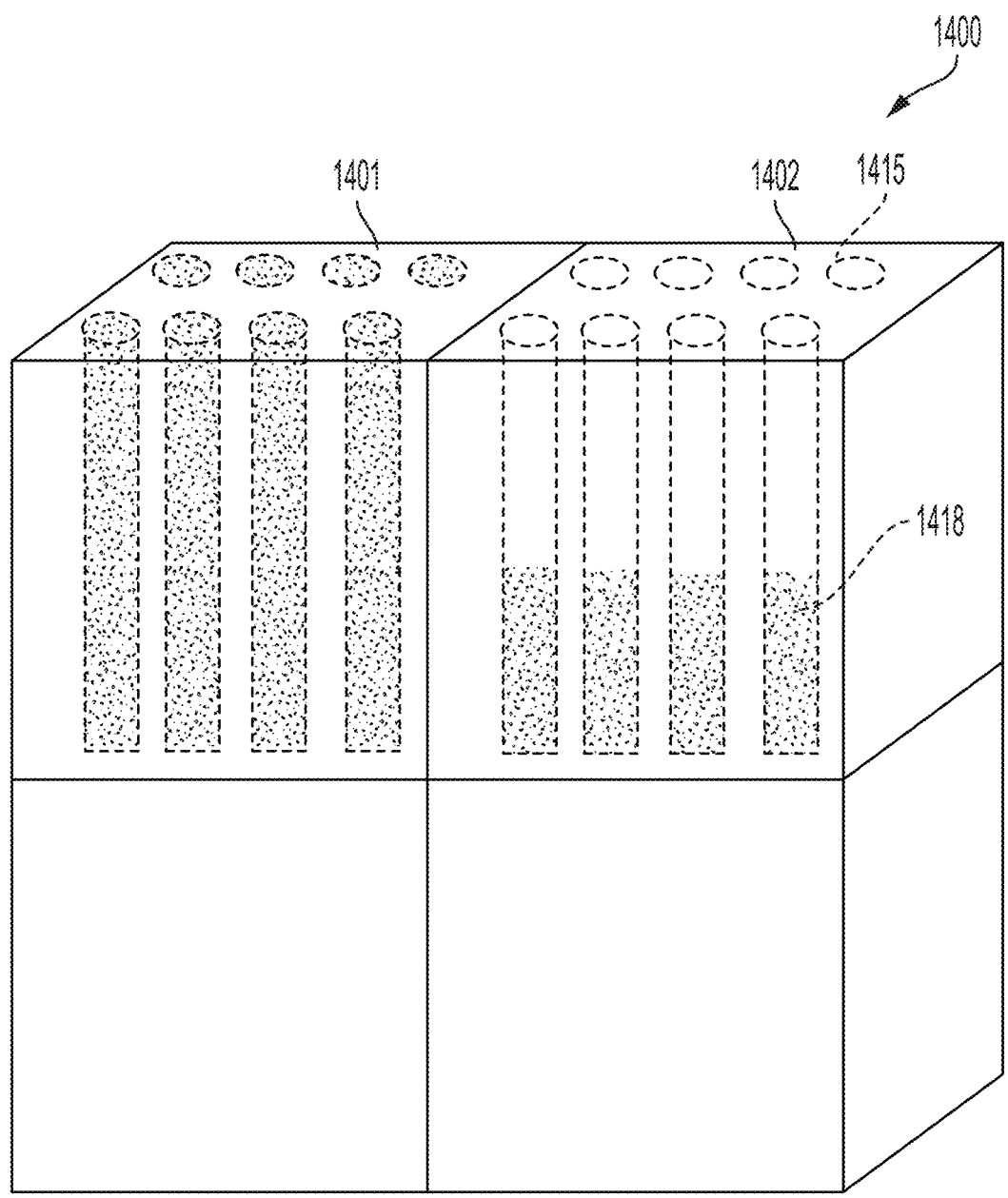
Figure 42:
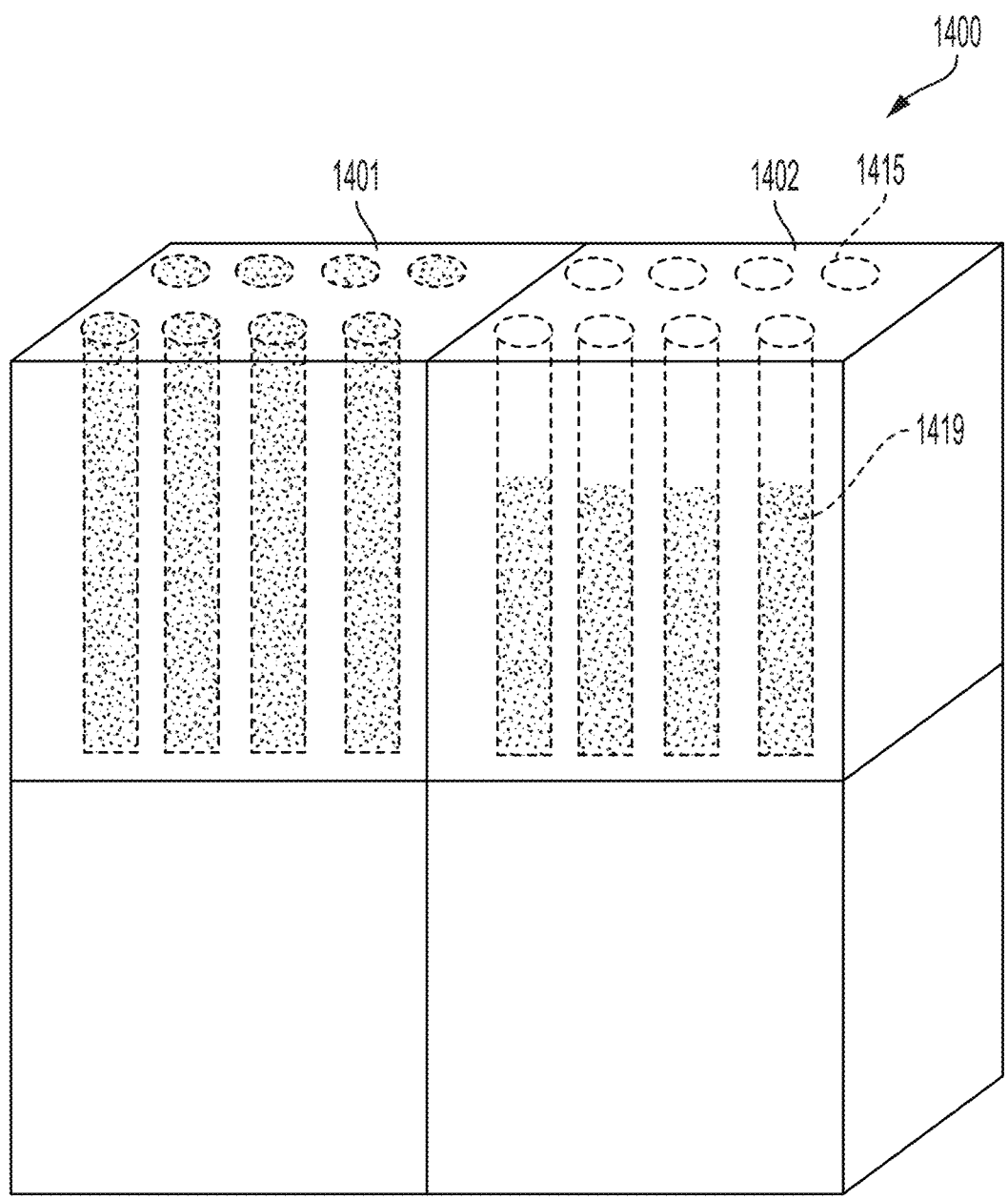
Figure 43:
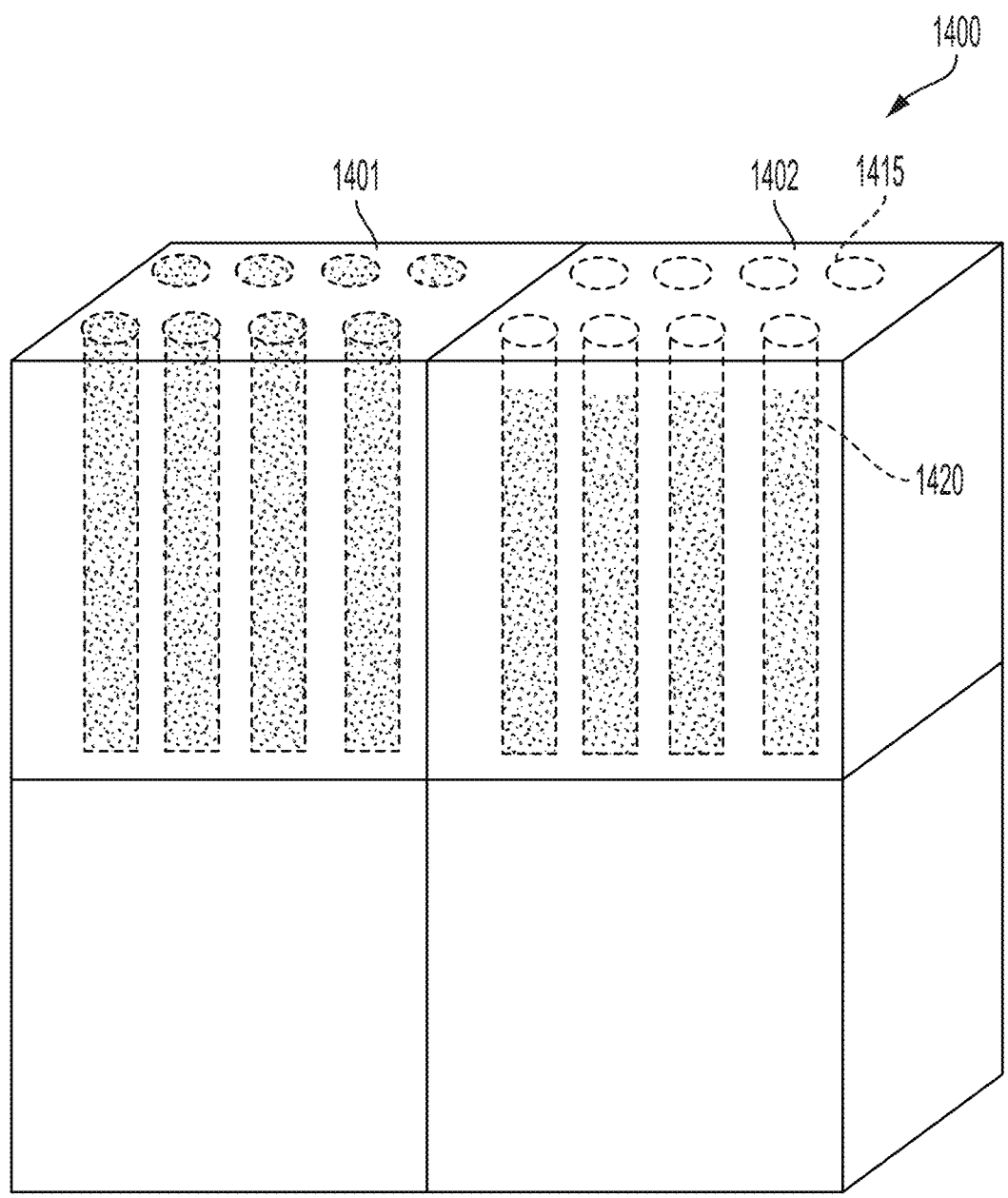
Figure 44:
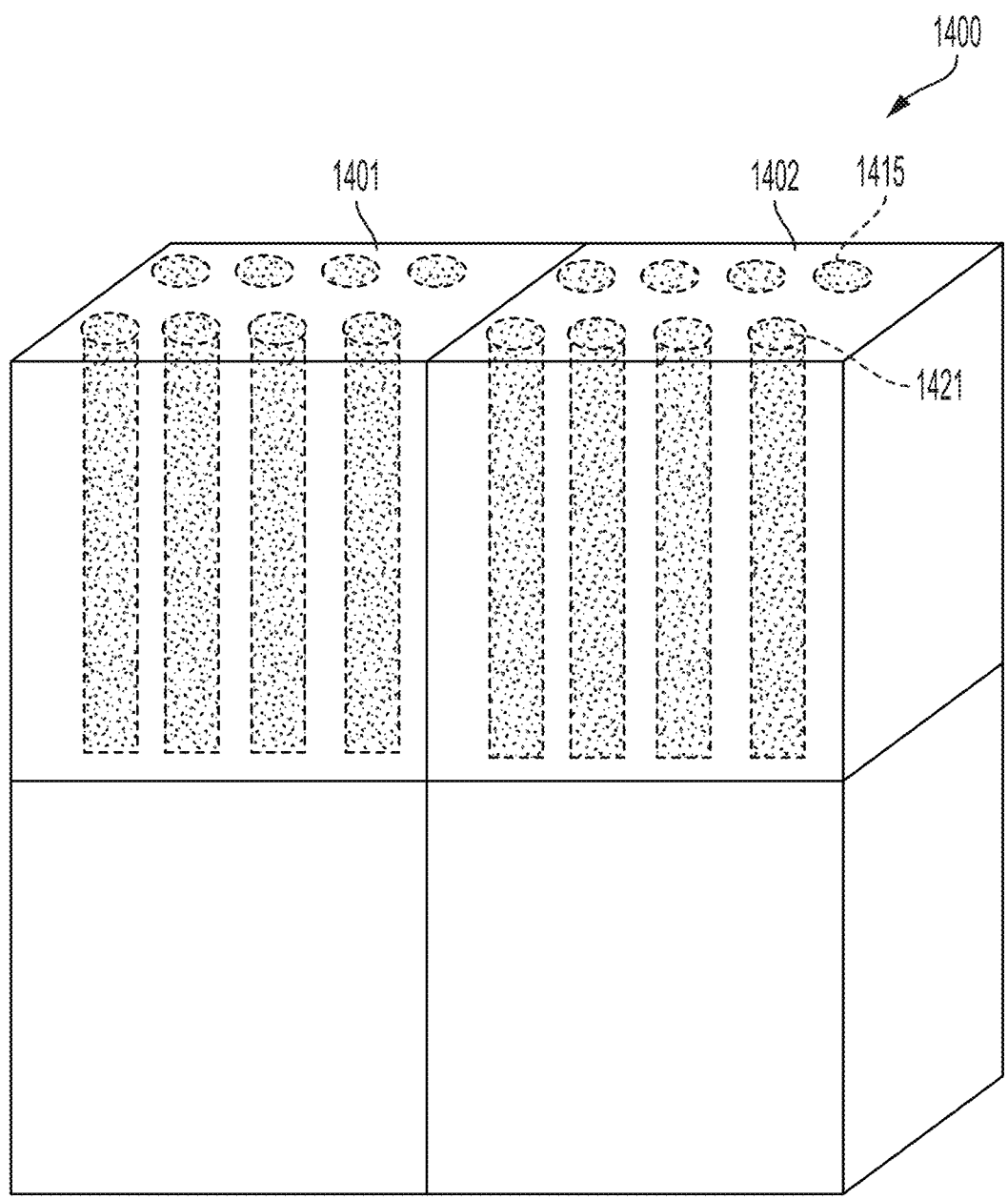

After micro-volume 1401 is treated, the next micro-volume 1402 is treated in a similar manner. In FIG. 40, the deepest parts 1417 of columns 1415 are treated. In FIG. 41, the next deepest parts 1418 of columns 1415 are treated. In FIG. 42, the next deepest parts 1419 of columns 1415 are treated. In FIG. 43, the next deepest parts 1420 of columns 1415 are treated. In FIG. 44, the shallowest parts 1421 of columns 1415 are treated, thereby completing treatment of micro-volume 1402. As was the case above, although the columns are separated for clarity, the columns may actually overlap at least in part as is the case with respect to FIGS. 12 to 19 to ensure that the entire micro-volume is treated with radiation.

After micro-volume 1402 is treated, the remaining micro-volumes may be treated in a similar manner. The micro-volumes may be treated in any order or sequence and using any appropriate number and placement of columns. In addition, as described herein, individual columns may be treated using different bean intensities. These intensities may vary from column-to-column, from micro-volume-to-micro-volume or both from column-to-column and from micro-volume-to-micro-volume. Furthermore, each micro-volume may be treated from multiple different angles as part of intensity-modulated proton therapy treatment (IMPT).

Figure 45A:
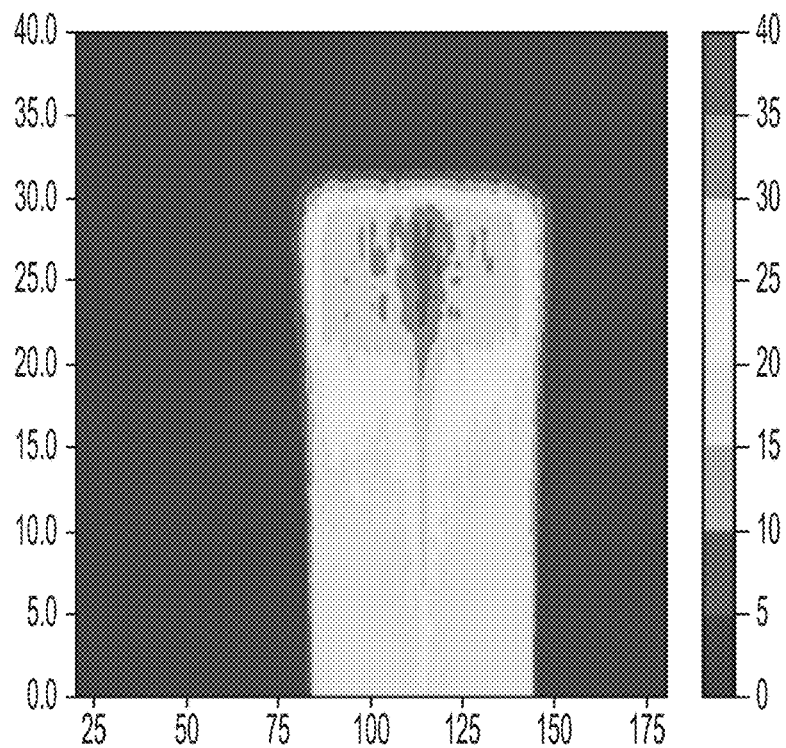
FIGS. 45A and 45B are plots showing results of Monte Carlo simulations that calculate radiation dose delivered to a treatment volume and the time it takes for each voxel in that dose calculation to reach a final dose.
Figure 45B:
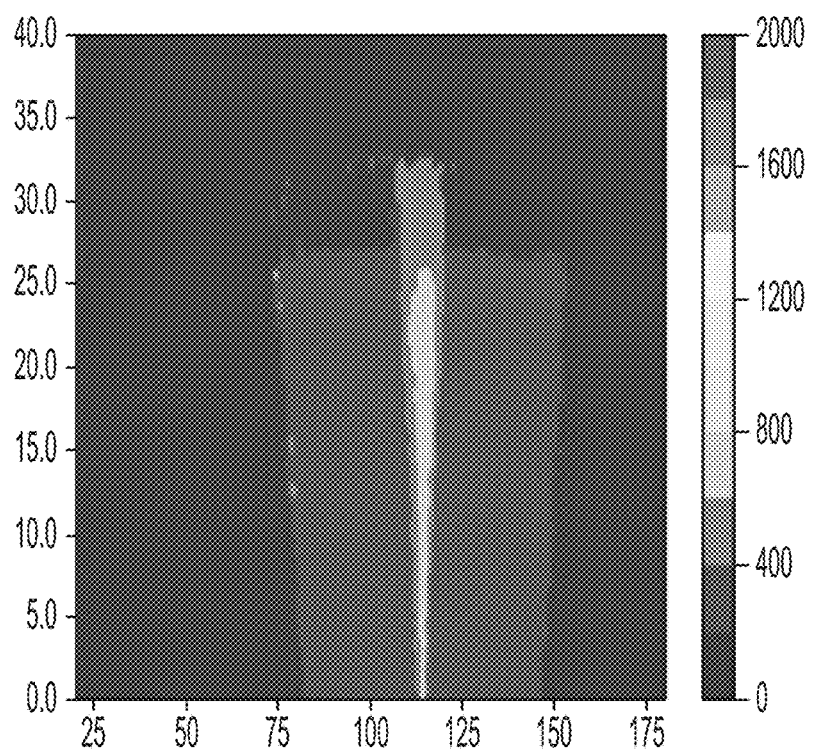

In an example, plots of FIGS. 45A and 45B show the results of Monte Carlo simulations that calculate radiation dose delivered to a treatment volume as well as the time it takes for each voxel in that dose calculation to reach the final dose. In an example, applying performance modifications to some parameters of a synchrocyclotron—for example, 10 ms layer switching time instead of 50 ms layer switching time, increasing the beam current, and enhancing pulse-pulse stability—spots delivered on a cube that is 3 cm on each side can be delivered with every part of the treatment volume receiving its dose in less than 500 ms. These small cubes were not strictly delivered in columns where each energy layer has a single spot, but rather in micro-volumes where each layer has a few (e.g., 10 to 20) spots. In addition, collimation may be used to isolate one micro-volume from another, allowing these volumes to be delivered in a reasonable amount of total treatment time. For example, the collimators described herein or any other appropriate collimating device, including standard multi-leaf collimators (MLC), may be used.

In some implementations, each micro-volume may be treated in the manner described with respect to FIGS. 12 to 19. For example, the entirety of a column in a micro-volume may be treated before moving on to a next column in the same micro-volume. Once all columns are treated in a micro-volume are treated, then treatment proceeds to the next micro-volume. There, treatment is repeated until all columns of the micro-volume are treated. Treatment then proceeds to the next micro-volume and so on until the entire irradiation target is treated. These implementations differ from the implementations of FIGS. 35 to 44 in which an entire depth—or micro-layer—of each column in a micro-volume is treated at once for every column in that micro-volume. Thereafter, treatment proceeds to the next depth and so forth until all columns in the micro-volume have been treated.

Delivering radiation at ultra-high dose (FLASH) rates to all or part of a column as described herein may be implemented to deposit doses of radiation in any random manner. For example, referring to FIG. 34, an example column 1299 in a radiation target may be comprised of multiple depths. Each depth may comprise a micro-layer of the target that has about the diameter of a spot of the particle beam. Using delivery or radiation by column as described herein, radiation may be delivered to each of depths 1301, 1302, and 1303 at ultra-high dose (FLASH) rates. Doses may be delivered in any manner established by the treatment plan. For example, a higher dose of radiation may be applied to depth 1303 than to depths 1301 or 1302. In another example, the highest dose may be applied to depth 1303, the next highest dose may be applied to depth 1302, and the lowest dose may be applied to depth 1302. In another example, the highest dose may be applied to depth 1301, the next highest dose may be applied to depth 1303, and the lowest dose may be applied to depth 1302. Thus, doses may be applied without regard to—for example, independent of—the shape of a Bragg peak produced by summing the multiple doses. In other words, in some cases, the doses may not be configured to obtain a spread-out Bragg peak along a column of radiation delivered to an irradiation target at ultra-high dose (FLASH) rates or at lower dose rates.

Figure 34:
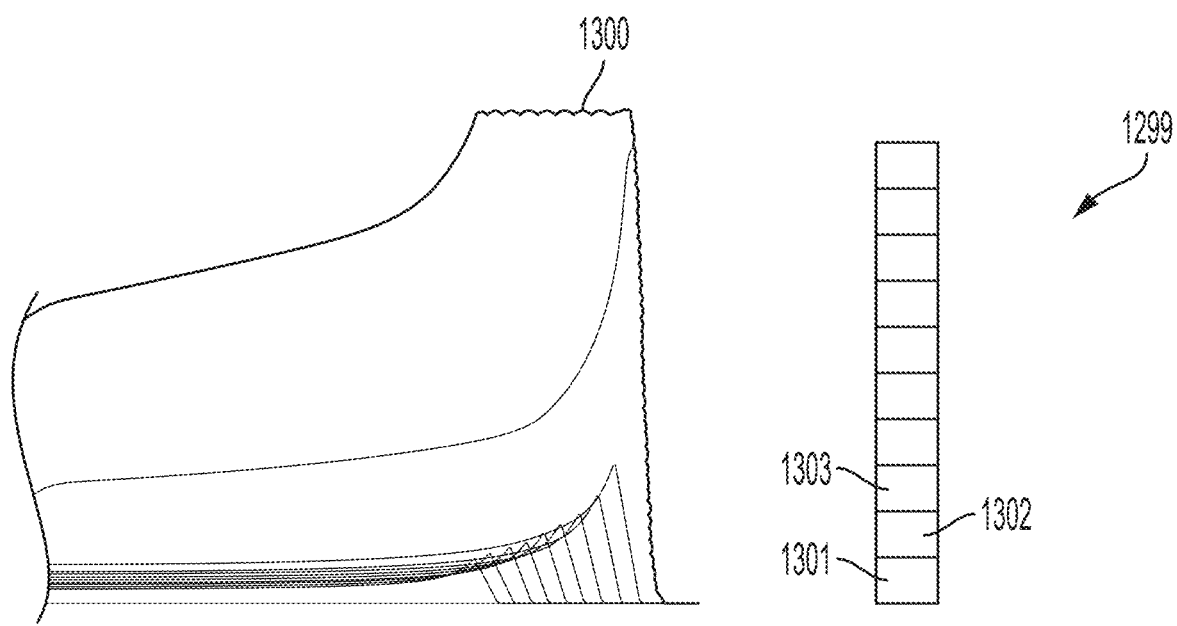
FIG. 34 is a diagram showing an example spread-out Bragg peak (SOBP) and a column that is part of example irradiation target.

In some implementations, one or more ridge filters or range modulator wheels may be added into the path of the particle beam to spread out—for example, to elongate—the Bragg peak of the particle beam. An elongated or spread-out Bragg peak is created by using a uniform depth-dose curve. That is, the dose is calibrated based on the depth in the tissue to which the dose is to be delivered in order to achieve an elongated Bragg peak that is flat or substantially flat. Referring to FIG. 34, for example, to achieve a spread-out Bragg peak such as 1300 using delivery of radiation by column, a full (100%) dose may be applied to depth 1301 in column 1299 of an irradiation target for a period of time. Next, an 80% dose may be applied to depth 1302 for a period of time. Depth 1302 is up-beam (that is, more shallow) than depth 1301. Next, a 66% dose may be applied to depth 1303 for a period of time. Depth 1303 is up-beam (that is, more shallow) than depth 1302. This may be repeated until spread-out Bragg peak 1300 is achieved.

Motors may control movement of the one or more ridge filters or range modulator wheels into or out of the path of the particle beam. The motors may be responsive to command of the control system. Spreading out the Bragg peak of the particle beam may be used for both columnar treatment as shown in FIGS. 12 to 19 or layer-by-layer treatment as shown in FIG. 1. In some implementations, the intensity of the particle beam may be increased using techniques such as those described herein when the Bragg peak is spread-out.

In some implementations, a range modulator wheel may be robotically controlled to move in two dimensions or in three dimensions within the beam field so as to track movement of the particle beam. For example, the range modulator wheel may be robotically controlled to move in the Cartesian X, Y, and/or Z dimensions. The range modulator wheel may have varying thicknesses and may spin to change the Bragg peak of the particle beam and thus the depth within the target at which a majority of the particles are deposited. In some implementations, the range modulator wheel may include steps that define its various thicknesses. In some implementations, the intensity of the particle beam may be controlled in order to control the dose delivered at each location on the range modulator wheel. This may be done in order to control depth-dose distributions.

Figure 20:
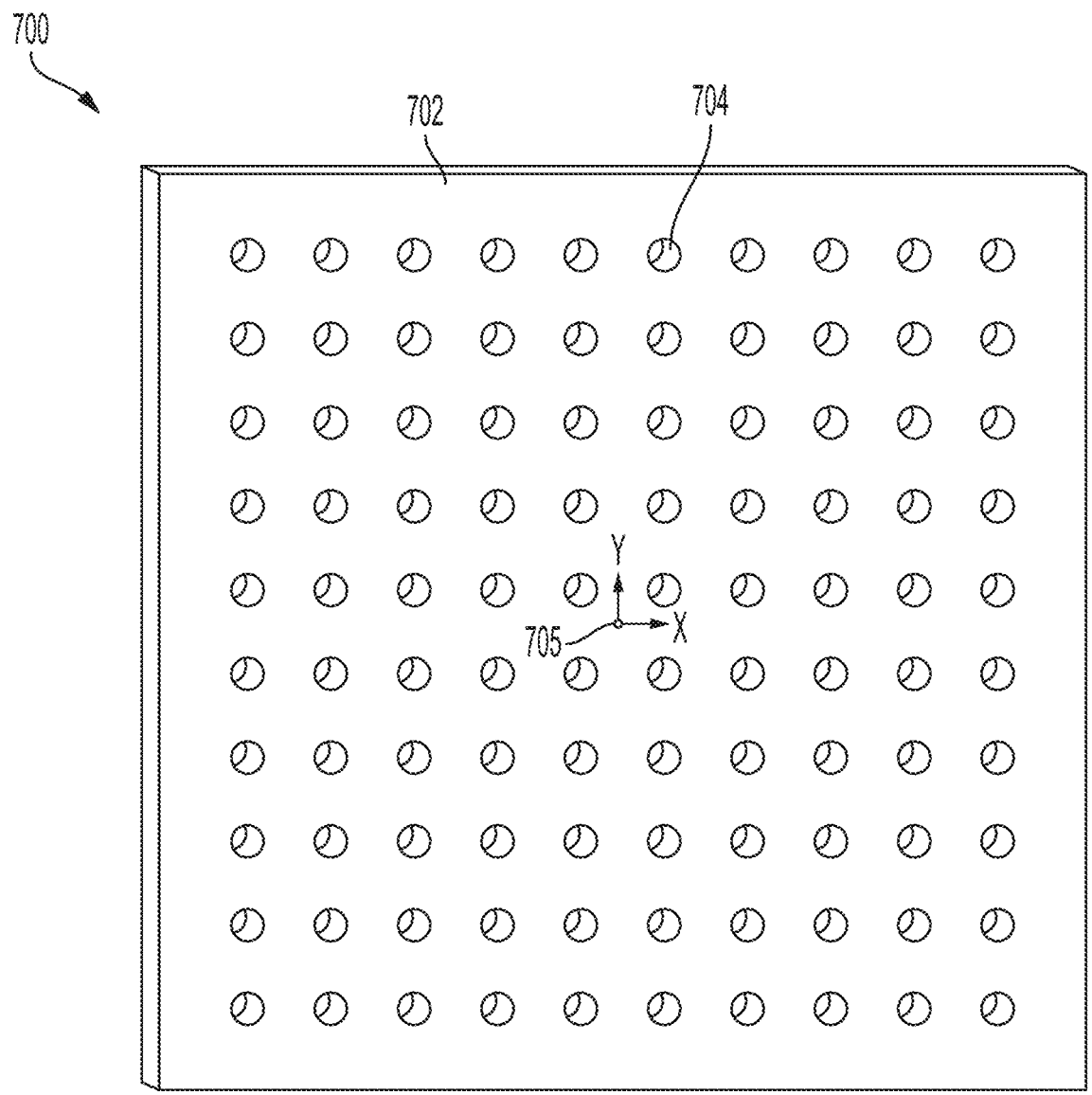
FIG. 20 is a front view of an example collimator containing a two-dimensional array of holes.

As explained above, the scanning system includes a collimator. The collimator may be controlled by the control system to trim the particle beam prior to the particle beam reaching the target in the patient. FIG. 20 shows an example implementation of a collimator 700 that may be used with a particle therapy system such as those described herein. Collimator 700 includes a carrier 702. In this example, the carrier is a plate; however, the carrier may have any appropriate structure, such as a polyhedron or a three-dimensional curved structure such as cylinder, cone, or sphere. As previously explained, the carrier may be made of a metal or other material such as nickel, brass, or tungsten having a thickness sufficient to prevent passage of radiation at a given energy. For example, the carrier may be constructed—for example, have a thickness and a composition—to prevent passage of a proton beam having an energy of 100 MeV, 150 MeV, 200 MeV, 250 MeV, or 300 MeV. In this example, the openings 704 in the carrier include a two-dimensional 705 array of holes. The holes are circular in this example; however, any appropriately shaped hole may be used. For example, the holes may be oval, square, polygonal, or any other appropriate shape. The holes may be sized based on the size of the particle beam at the location of the collimator and based on the amount of trimming and collimation to be produced. In this regard, in some implementations, the spot size that is producible by the system is between 2 mm sigma and 20 mm sigma. The holes may be formed to produce collimation in this range. As explained previously, in some implementations, the sizes and/or shapes of the holes are not changeable or configurable. This may reduce the amount of time needed reconfigure the system when delivering ultra-high dose rate radiation. In some implementations, the sizes and/or shapes of the holes are configured to allow a pre-defined amount of bream spreading post collimation.

Figure 21:
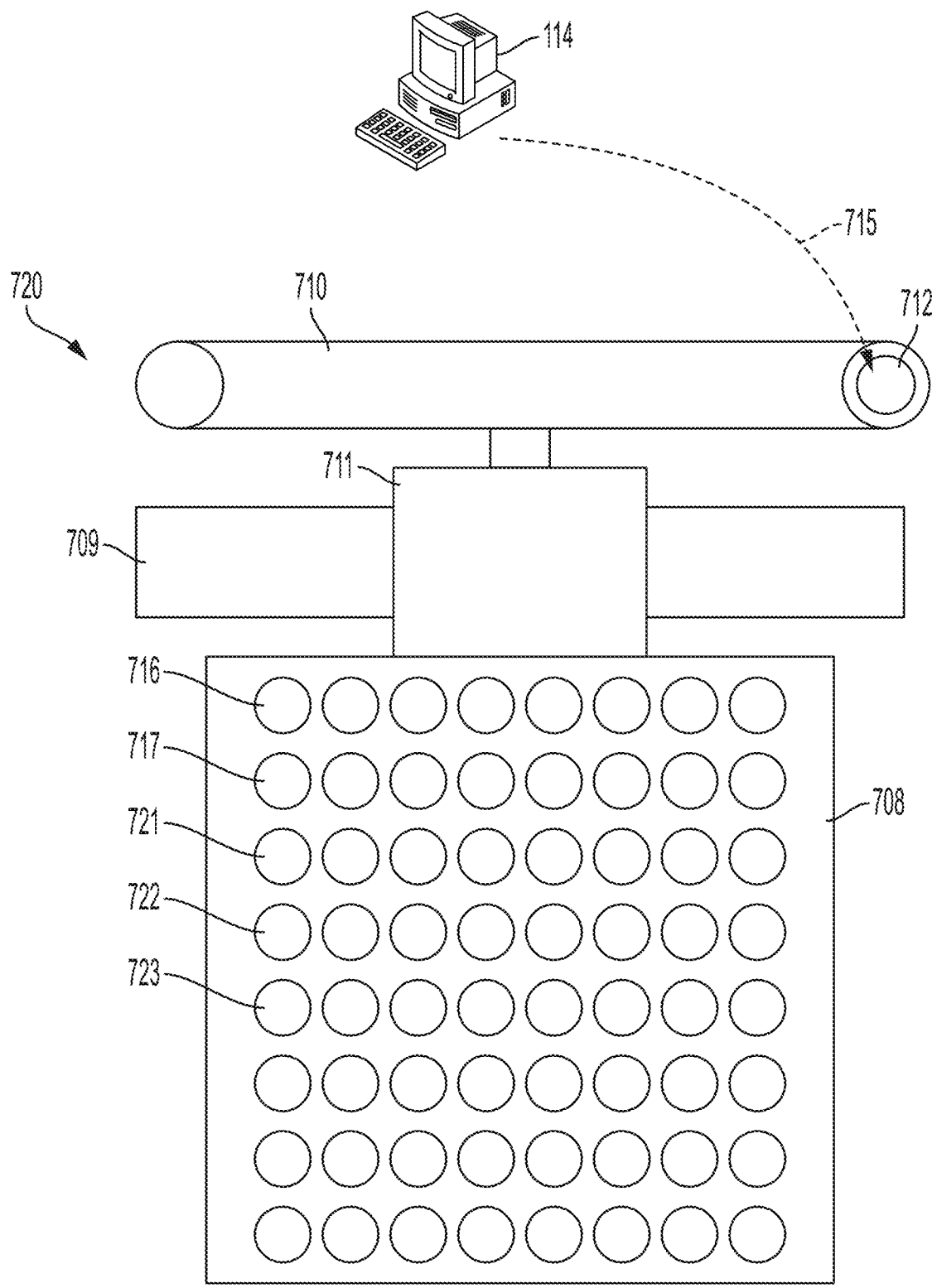
FIG. 21 is a front view of an example collimator containing a two-dimensional array of holes and control components for the collimator.

In some implementations, the carrier may be movable within, or across the entirety of, the beam field. As previously explained, in some examples, the beam field is the maximum extent that the particle beam can be moved across a plane parallel to the treatment area on a patient. In example collimator 720 of FIG. 21, carrier 708 may be mounted to a track 709 and connected to a belt 710 via physical couplings 711. A rotary motor 712 may drive belt 710 to move the carrier along the track to position the carrier within the beam field. For example, rotary motor 712 may be responsive to commands (shown as dashed line 715) from the control system 114 to position the carrier prior to treatment and to leave the carrier in place during treatment. In alternative implementations, the motor may be a rotary motor that drives a corresponding linear actuator to control movement of carrier across at least part of the beam field. In some implementations, the carrier may be moved during treatment. For example, the carrier may be moved based on movement of the particle beam. For instance, if the treatment area exceeds the dimensions of the collimator, the collimator may be moved by motor 712 in between treatment of columns to position the collimator to treat additional parts of the target. In another example, the collimator may be moved in concert with—that is, track—movement of the particle beam as the particle beam traverses the beam field.

In some implementations, the carrier may be movable in one, two, or three dimensions within the beam field. For example, as described above, the carrier may be mounted on a track to move through the beam field in one dimension. In some implementations, the carrier may be robotically controlled to move in two or three dimensions within the beam field. In some implementations, the track (and its associated assembly, such as the motor and the belt) to which the carrier is connected may itself be connected to a carriage (not shown) that is controllable to move in a dimension that is orthogonal to the track. For example, the carriage may be controlled by a motor that is responsive to one or more commands from the control system. The control system may therefore instruct movement of the carrier along the track and movement of the track via the carriage, thereby implementing two dimensional movement of the carrier within the beam field.

In some implementations, motion of the carrier may be monitored or determined using one or more encoders. In some examples, encoders include electronic devices that are connected to the carrier or to an assembly or structure that moves along with the carrier. The encoders may include or more of laser sensors, optic sensors, or diode sensors. The encoders detect movement of the carrier, e.g., by detecting where markings or other indicia on the carrier, or on structures that are connected to and that move with the carrier, are located relative to the encoders. Information about a location of the carrier is fed back to the control system and is used by the control system to confirm the position of the carrier and, in some implementations, to change its position. The encoders may be, or include, simple electronic sensors that are not particularly sensitive to neutron radiation and that, therefore, may be located in the treatment room.

As explained previously, in some implementations the collimator is used in implementing a treatment plan to deliver ultra-high dose rate radiation to columns of a target in a patient. To this end, the control system may be configured to control movement of the particle beam to a first hole 716 of collimator 720 to enable at least part of the particle beam to reach the patient through the first hole, to change an energy of the particle beam while the particle beam remains stationary at the first hole, and to control movement of the particle beam from first hole 716 to a second hole 717. In some implementations, the center of the particle beam spot—for example, the cross-sectional area of the particle beam—is positioned at the center of each hole. The energy of the particle beam may be changed by moving energy-absorbing structures into or out of the path of the particle beam or by changing a current through a superconducting magnet used in a variable-energy particle accelerator, as described herein. The motion (or "steering") of the particle beam may be controlled by varying or not varying the current through the scanning magnet described with respect to FIGS. 4 to 7. The control system may also be configured to change an energy of the particle beam while the particle beam remains stationary at second hole 717 and to control movement of the particle beam from second hole 717 to multiple additional holes in a sequence that may be defined by the treatment plan. At each of the multiple additional holes, such as 721, 722, and 723 and so forth the particle beam is controlled to remain stationary for a period of time while the energy of the particle beam changes. As a result, at each hole, the particle beam is trimmed and, by virtue of the energy change, the particle beam treats a three-dimensional column within the target as described with respect to FIGS. 2, 12 to 19, and 35 to 44. As previously explained, the openings such as the holes of FIG. 21 may be positioned relative to one another to achieve a desired amount of overlap, or no overlap, between adjacent columns in the target.

Figure 26:
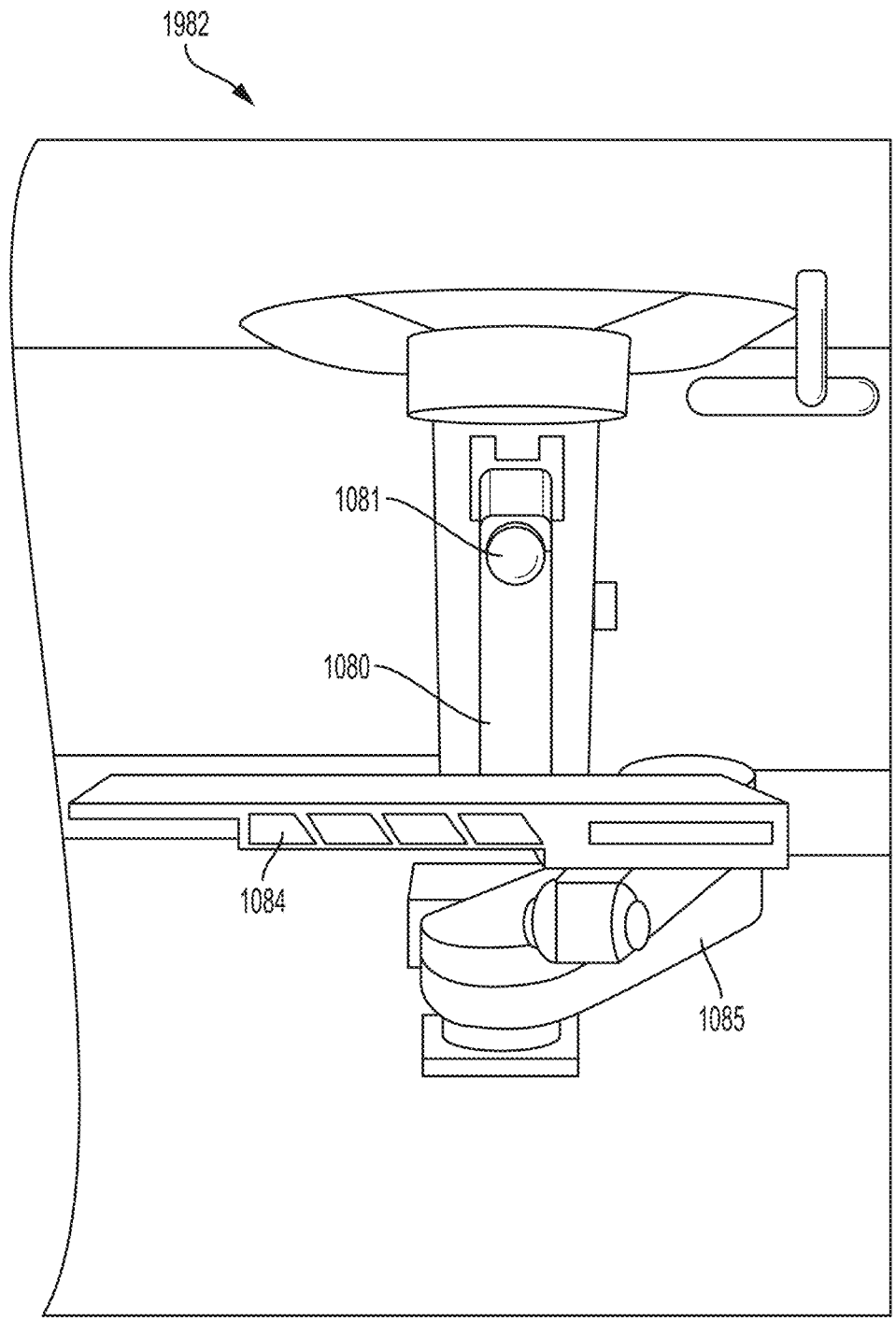
FIGS. 26 and 27 are front and perspective views, respectively, of an example particle therapy system.
Figure 27:
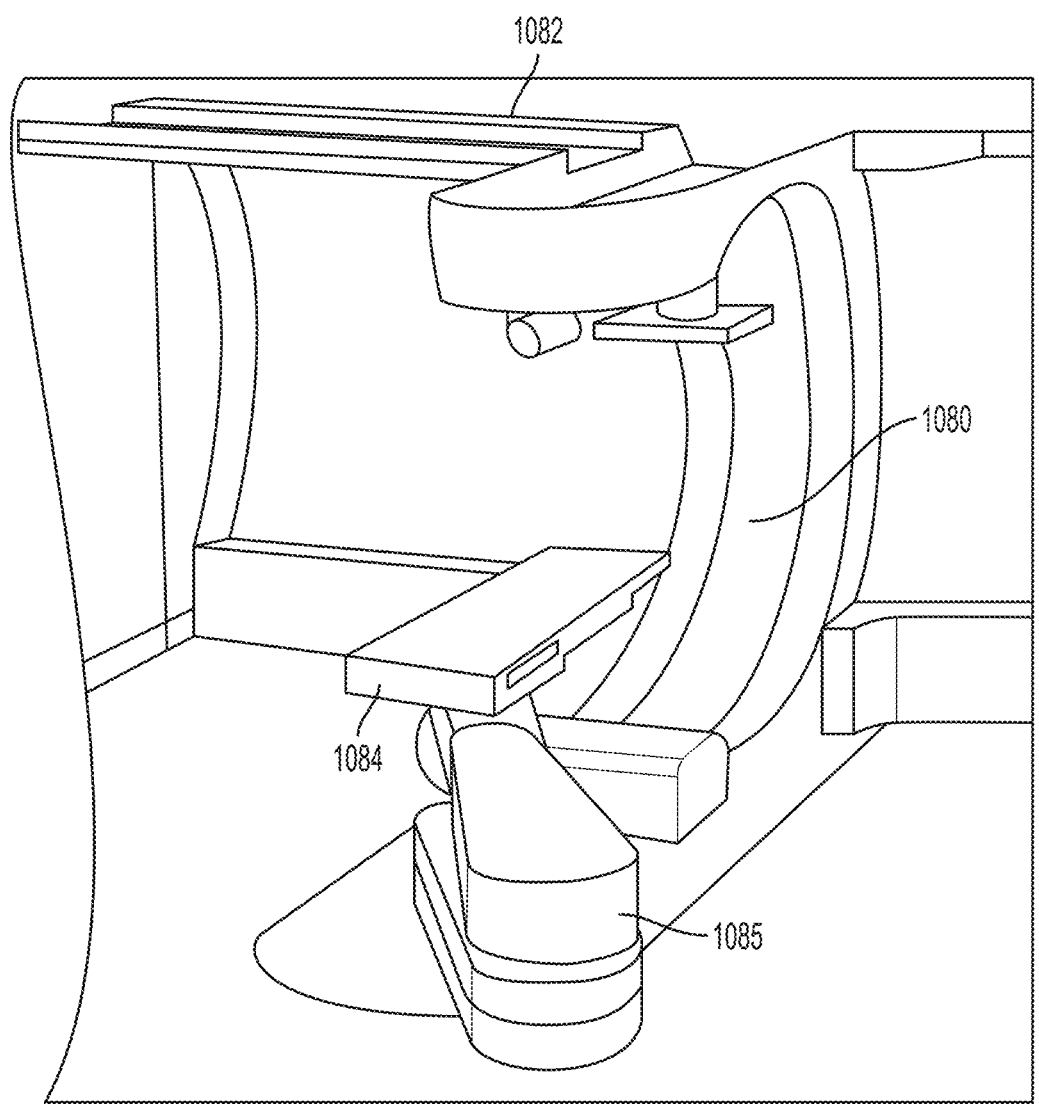
Figure 28:
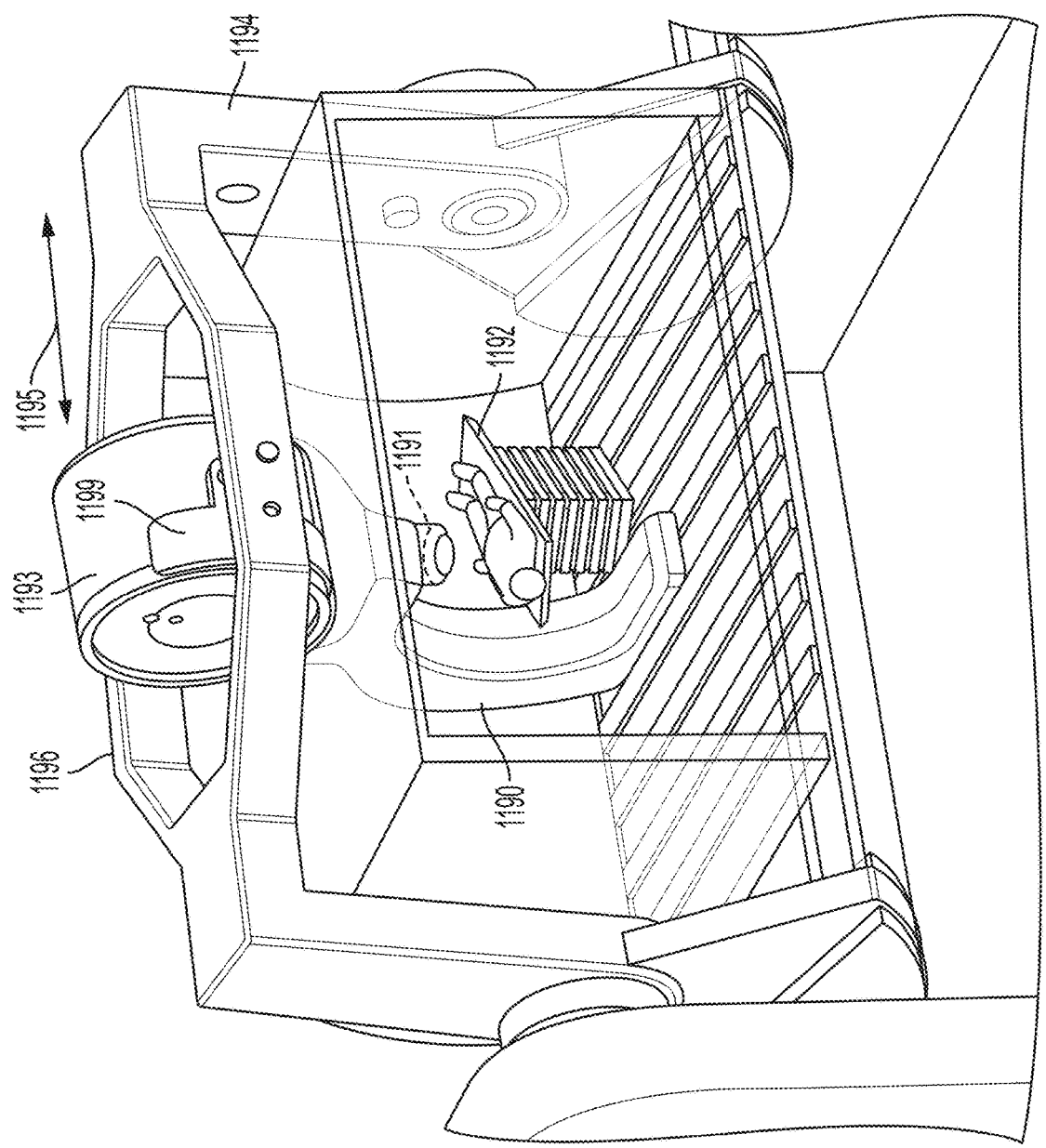
FIG. 28 is a perspective view of an example particle therapy system.

In some implementations, the collimator may be mounted within a nozzle on a system's inner gantry, examples of which are described with respect to FIGS. 26, 27, and 28. In this regard, the collimator may be located down-beam of the energy degrader relative to the particle accelerator. In other words, the collimator may be located more near to the patient than the energy degrader. This is because the energy degrader may cause some dispersion of the particle beam and that dispersion may be reduced or corrected by the collimator. The nozzle may be configured to move the collimator towards or away from the patient. In addition, the nozzle, including the collimator, may be retracted fully within the inner gantry, thereby taking the collimator out of the way of a technician administering the treatment. In some implementations, the inner gantry may be flush with a wall of the treatment room, in which case retracting the nozzle and the collimator fully within the inner gantry causes the nozzle and collimator to retract fully within the wall.

Figure 22:
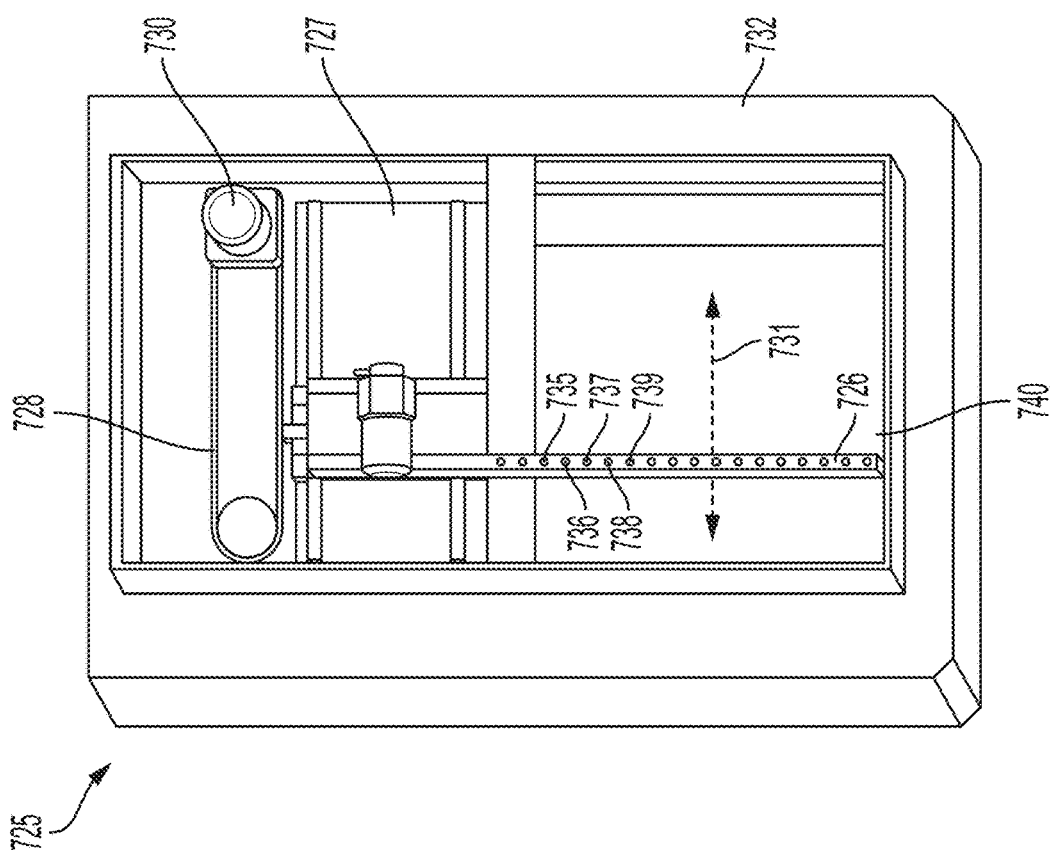
FIG. 22 is a perspective view of an example collimator containing a single linear array of holes.

FIG. 22 shows an example implementation of a collimator 725 that includes a single linear array of holes. Except for the arrangement of the holes in the single linear array, the composition of collimator 725 and the structure of the holes may be the same as those of collimator 720. In this example, the carrier 726 that includes the holes is mounted to track 727 and connected to belt 728. Rotary motor 730 drives belt 728 either clockwise or counterclockwise, which causes carrier 726 to move in either direction of arrow 731 within frame 732. Motor 730 may be responsive to commands from the control system to cause carrier 731 to move when the particle beam is to move to an area adjacent to carrier 726. In an example, the control system may be configured to control movement of the particle beam to a first hole 735 of collimator 725 to enable at least part of the particle beam to reach the patient, to change an energy of the particle beam while the particle beam remains stationary at the first hole, and to control movement of the particle beam from first hole 735 to a second hole 736. The control system may also be configured to change an energy of the particle beam while the particle beam remains stationary at second hole 736 and to control movement of the particle beam from second hole 736 downwards to multiple additional holes in the linear array defined by carrier 726. At each of the multiple additional holes, such as 737, 738, and 739 the particle beam is controlled to remain stationary for a period of time while the energy of the particle beam changes, thereby treating columns within the target at all hole locations.

Figure 23:
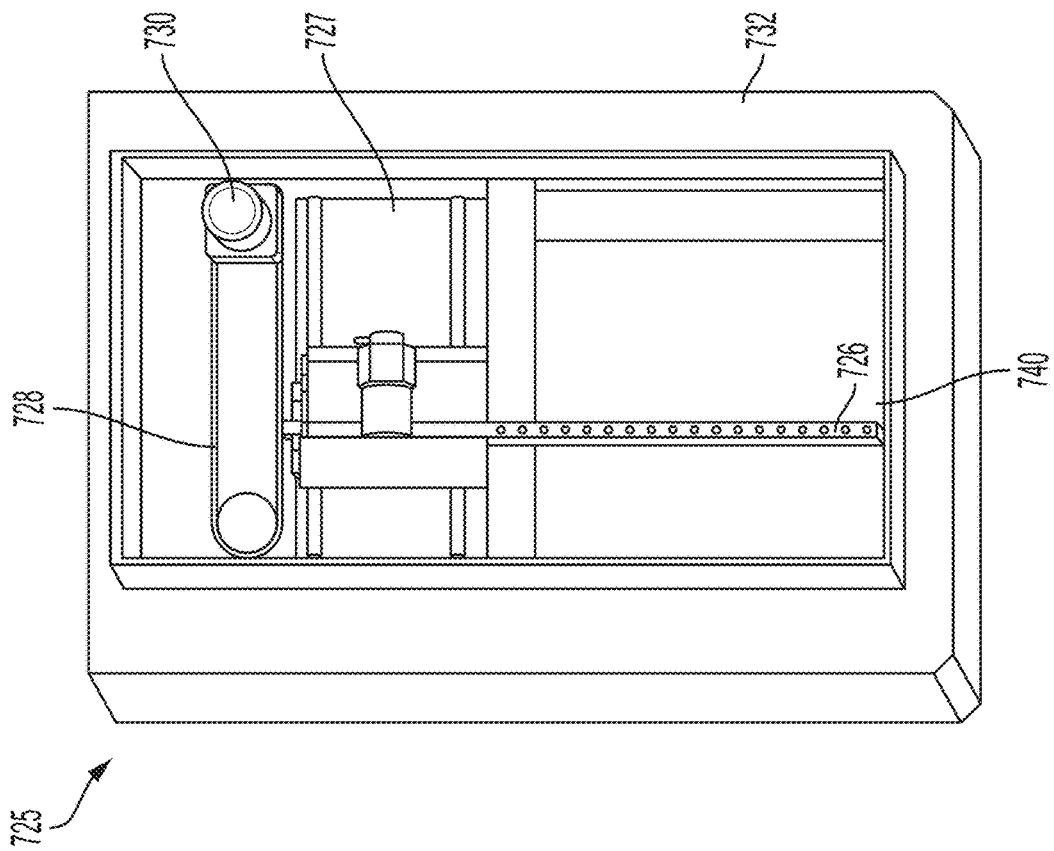
FIG. 23 is a perspective view of the example collimator of FIG. 22.

When the particle beam is to move to another area, such as area 740 that is adjacent to the carrier, carrier 726 may first be moved to cover that area so that columns within the target underneath that area can be treated using ultra-high dose rate radiation as described previously. For example, as shown in FIG. 23, carrier 726 can be moved to area 740 and the particle beam can then be steered upwards through the holes in the carrier to treat columns within the target as described previously. This process may be repeated until the desired amount of the target is treated using ultra-high dose rate radiation. Although not shown in FIGS. 22 and 23, collimator 725 can be mounted to a carriage that is controllable to move in a dimension that is orthogonal to track 727. For example, the carriage may be controlled by a motor that is responsive to one or more commands from the control system. The control system may therefore instruct movement of carrier 726 along track 727 and movement of track 727 via the carriage, thereby implementing two dimensional movement of the carrier within the beam field. As noted, the collimator may also be connected to the nozzle, thereby allowing an additional dimension of movement towards or away from the patient.

Figure 24:
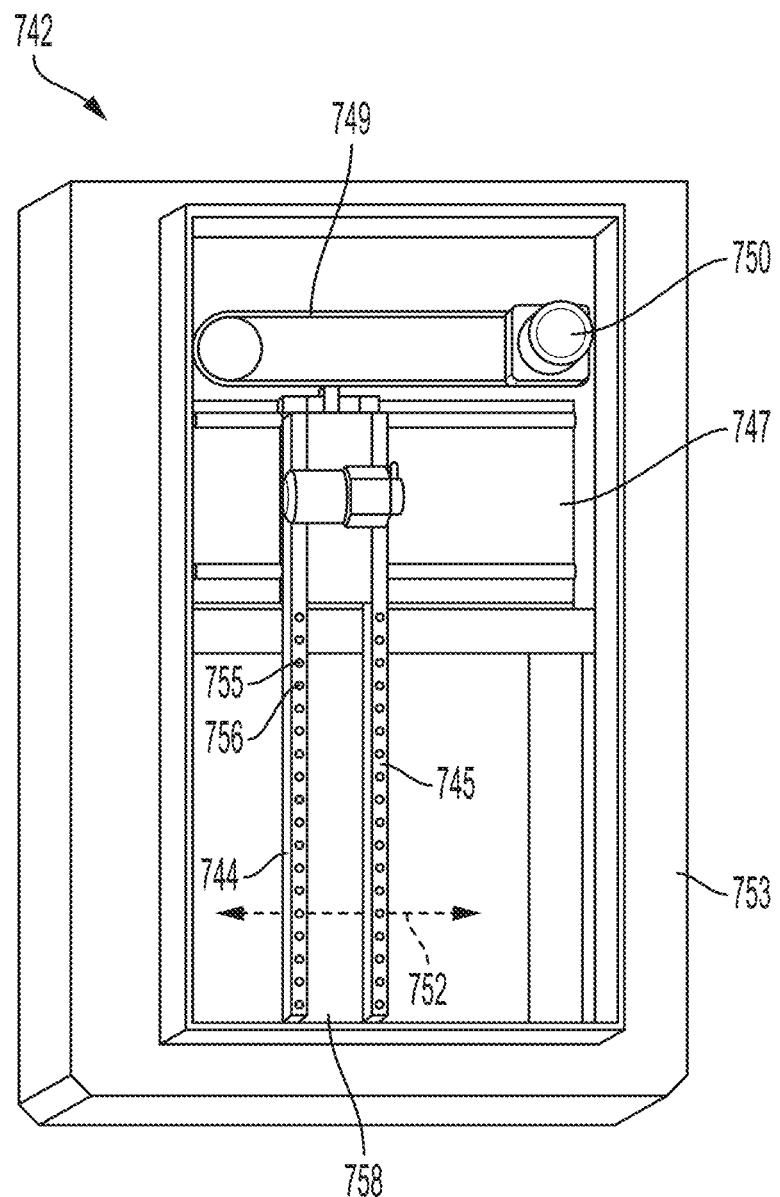
FIG. 24 is a perspective view of an example collimator containing two linear arrays of holes that are not independently controllable.

FIG. 24 shows a variation on collimator 725 of FIGS. 22 and 23. In this example collimator 742, there are two carriers 744 and 745 each including a linear array of holes. Except for the arrangement of the holes into two linear arrays, the composition of collimator 742 and the structure of the holes may be the same as for collimator 725. In this example, the two carriers may be physically connected to move along track 747 in concert. As explained above, the two carriers 744 and 745 are mounted to track 747 and connected to belt 749. Rotary motor 750 drives belt 749 either clockwise or counterclockwise, which causes the two carriers to move in either direction of arrow 752 within frame 753. Motor 750 may be responsive to commands from the control system to cause the carriers to move in order to comply with a treatment plan. In example, the control system may be configured to control movement of the particle beam to a first hole 755 of carrier 744 to enable at least part of the particle beam to reach the patient through the first hole, to change an energy of the particle beam while the particle beam remains stationary at the first hole, and to control movement of the particle beam from first hole 755 to a second hole 756. The control system may also be configured to change an energy of the particle beam while the particle beam remains stationary at second hole 756 and to control movement of the particle beam from second hole 756 downwards to multiple additional holes in the linear array of holes defined by carrier 744. At each of the multiple additional holes the particle beam is controlled to remain stationary for a period of time while the energy of the particle beam changes, thereby treating columns within the target. Thereafter, the particle beam can be steered to carrier 745 and upwards through the holes in carrier 745 to treat columns within the target underneath carrier 745. This process may be repeated until the desired amount of the target is treated using ultra-high dose rate radiation. Although not shown in FIG. 24, collimator 742 can be mounted to a carriage that is controllable to move in a dimension that is orthogonal to track 747. For example, the carriage may be controlled by a motor that is responsive to one or more commands from the control system. The control system may therefore instruct movement of the carriers along track 747 and movement of track 747 via the carriage, thereby implementing two dimensional movement of the carrier within the beam field. In some implementations different carriers 744 and 745 may be immediately adjacent or touching or there may be a separation 758 between the two as shown in FIG. 24. As noted, the collimator may also be connected to the nozzle, thereby allowing an additional dimension of movement towards or away from the patient.

Figure 25:
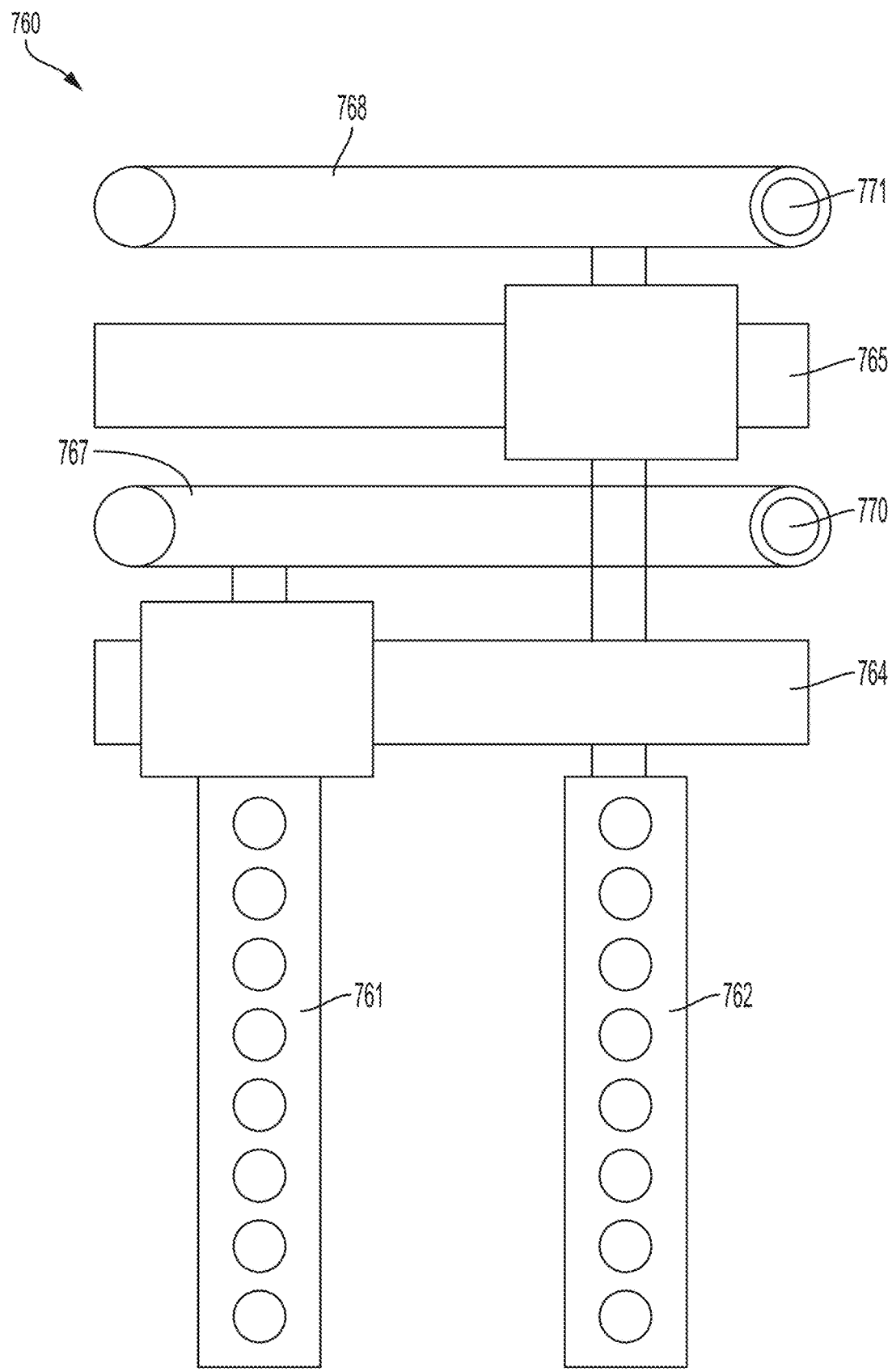
FIG. 25 is a front view of an example collimator containing carriers that are independently controllable.

In some implementations, as shown in FIG. 25, carriers 761 and 762 (which may have the same configuration as carriers 744 and 745, respectively) may be mounted to separate tracks 764 and 765, connected to separate belts 767 and 768, and controlled by separate rotary motors 770 and 771 that are each responsive to commands from the control system. The carriers 761 and 762 may thus be controlled to move independently of each other and relative to each other in order to implement ultra-high dose rate delivery of radiation in accordance with the treatment plan. Each part of collimator 760 and its associated assembly may have the same or similar structure and function as a corresponding part collimator 725.

Although not shown in FIG. 25, collimator 760 can be mounted to a carriage that is controllable to move in a dimension that is orthogonal to tracks 764 and 765. For example, the carriage may be controlled by a motor that is responsive to one or more commands from the control system. The control system may therefore instruct movement of the carriers along tracks 764 and 765 and movement of tracks 764 and 765 via the carriage, thereby implementing two dimensional movement of the carrier within the beam field. In some implementations, each of carriers 761 and 762 may be mounted to separate carriages, thereby enabling independent second dimensional movement of each of carriers 761 and 762. As noted, the collimator may also be connected to the nozzle, thereby allowing an additional dimension of movement towards or away from the patient.

In this regard, FIGS. 24 and 25 each shows two carriers, each containing a single linear array of holes. In some implementations, collimator 742 or 760 may include two or more carriers, each containing a linear array of holes or a two-dimensional array of holes. Each carrier may be physically connected as in FIG. 24 to move together, or each carrier may be independently coupled as in FIG. 25 and independently movable in response to commands from the control system. In addition, each carrier may be connected to enable second dimension movement using one or more carriages, as described previously. In some implementations, two motors may be configured to move carriers, such as carriers 761 and 762, along a single same track independently of each other.

Figure 30:
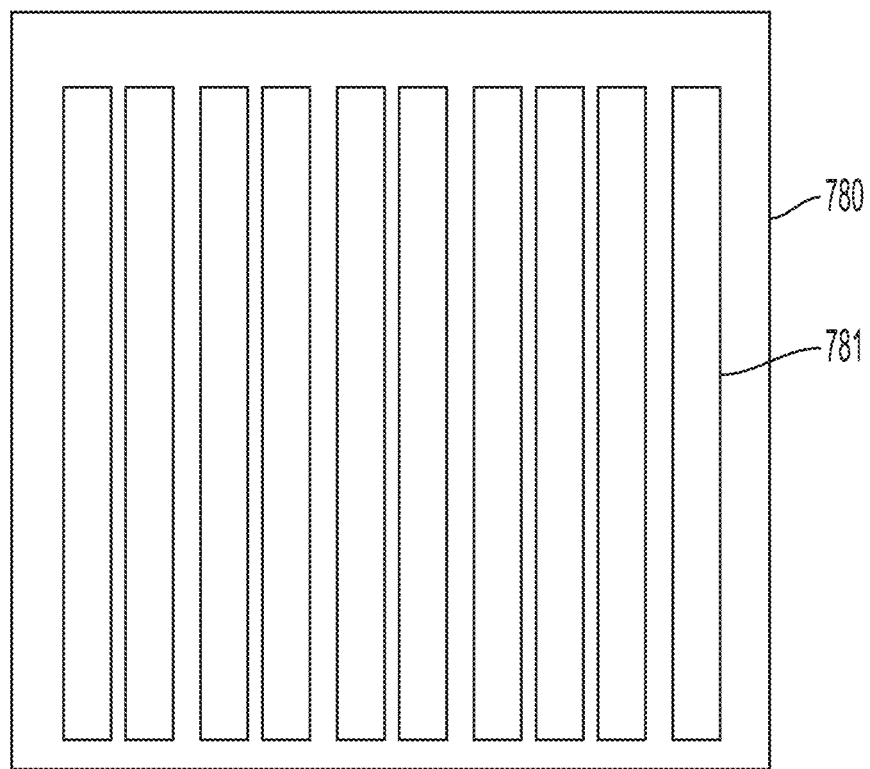
FIG. 30 is a front view of an example collimator containing a linear array of slots.
Figure 31:
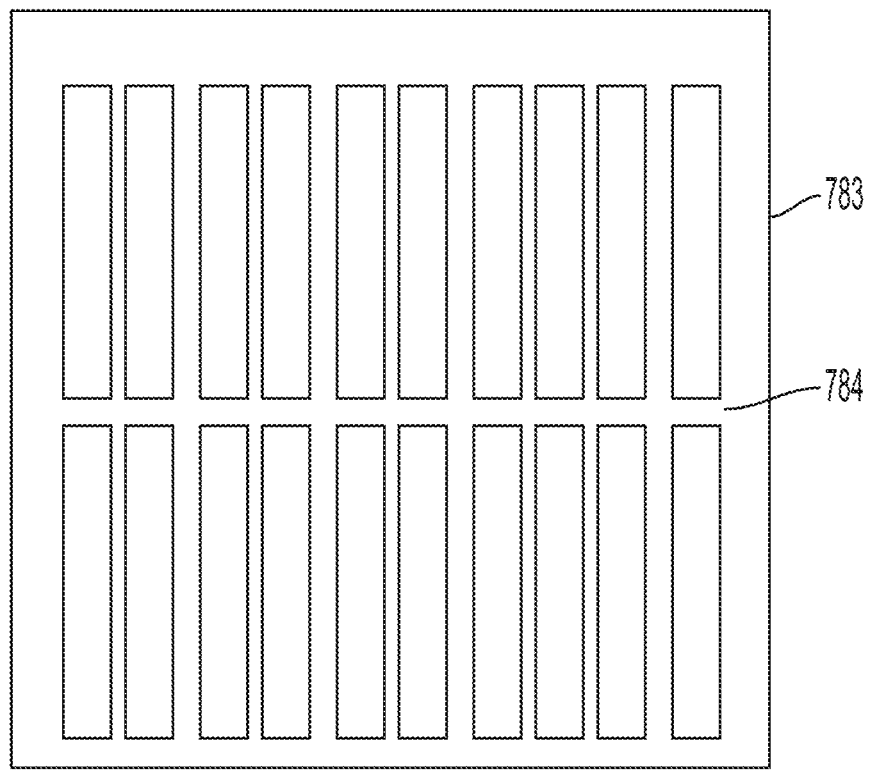
FIG. 31 is a front view of an example collimator containing a two-dimensional array of slots.

In some implementations, the openings through which particle beam passes may be slots instead of holes. An example slot is rectangular in shape and may extend over and across locations over a target where two or more spots of the particle beam are to be delivered. Any of the carriers shown in the implementations of FIGS. 20 to 25 may include slots as openings instead of holes. For example, each linear array of holes in FIGS. 20 to 25 may be replaced by a single slot or two or more adjacent slots. In this regard, FIG. 30 shows an example collimator 780 having an array of slots 781. In this example, the slots extend the entire length of the carrier. However, the slots may extend part-way down the carrier. For example, referring to FIG. 31, a collimator 783 may include a two-dimensional array of slots 784, with each individual slot extending about half-way down carrier 783.

Figure 32:
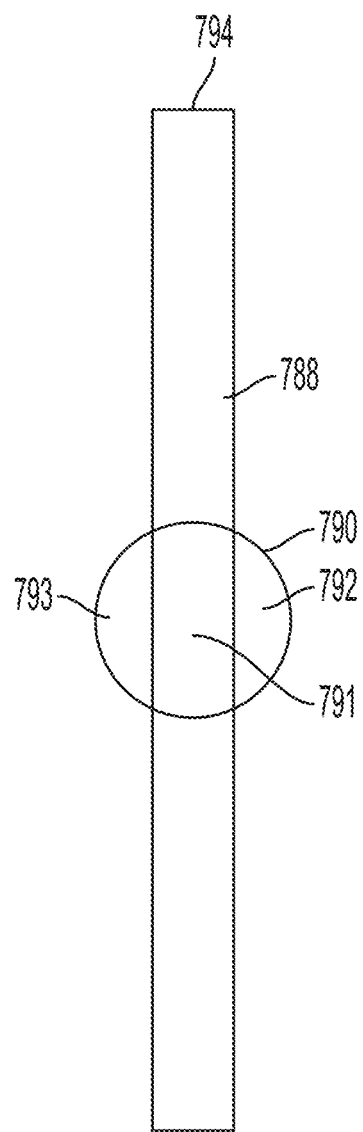
FIG. 32 is a front view of an example slot illustrating collimation performed by a slot on a particle beam.

The slots may be configured to trim and therefore collimate the particle beam in one dimension. For example, as shown in FIG. 32, example slot 788 collimates particle beam spot 790 by allowing part 791 of particle beam to pass through to the patient and to block parts 792 and 793 of the particle beam. At ends of the slots, such as end 794, the particle beam may be collimated in two dimensions. As was the case with collimators that use holes, collimators that use slots may also be used in implementing ultra-high dose rate radiation therapy.

Figure 33:
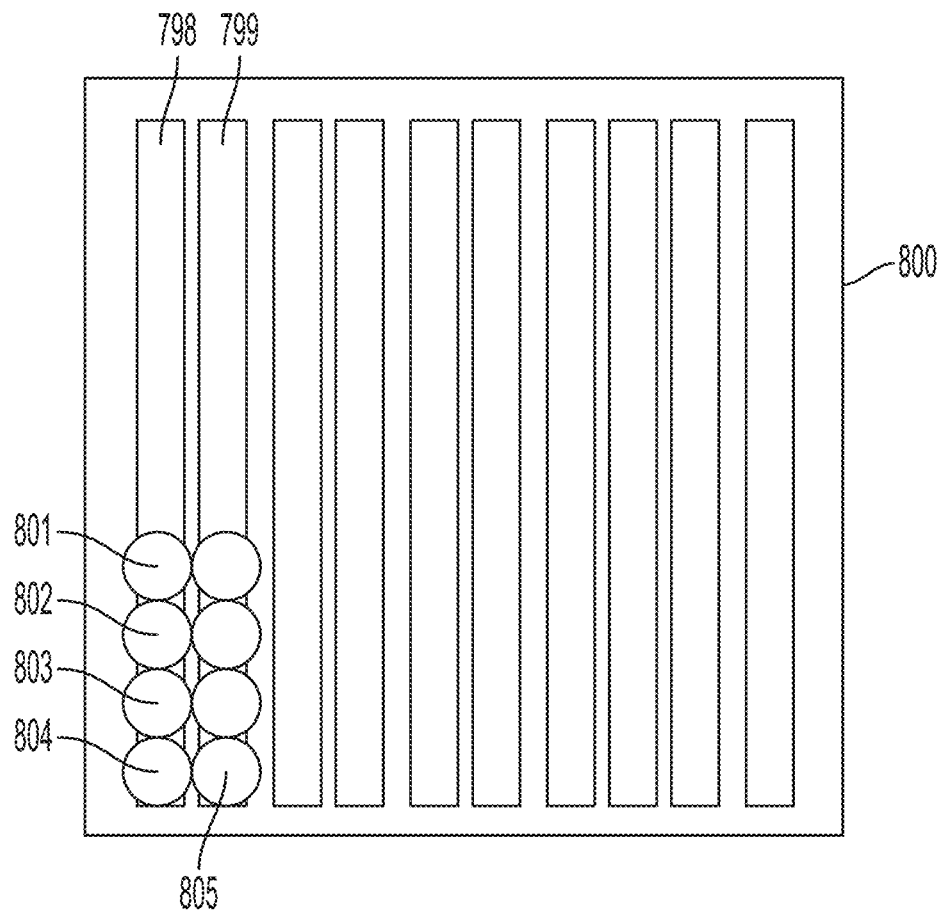
FIG. 33 is a front view of an example collimator containing a linear array of slots showing movement of the particle beam along parts of the slots.

Referring to example collimator 800 FIG. 33 for example, the control system may control movement of the particle beam to a first part 801 of slot 798 to enable at least part of the particle beam to reach the patient, to change an energy of the particle beam while the particle beam remains stationary at the first part 801 of slot 798, and to control movement of the particle beam from the first part 801 of slot 798 to a second part 802 of slot 798. The control system is also configured to change an energy of the particle beam while the particle beam remains stationary at the second part 802 of slot 798, and to control movement of the particle beam from the second part 802 of slot 798 to multiple additional parts 803 and 804 of slot 798. For example, the particle beam may be moved along slot 798 and deliver radiation at discrete locations along the slot. The particle beam is controlled to remain stationary for a period of time at each of the multiple additional parts of the slot while the energy of the particle beam changes at each part thereby treating columns of the target. The particle beam may then be moved to part 805 of slot 799 and proceed upwards along slot 799 depositing radiation in columns. Thus, a collimator that uses slots for openings may still be used to deliver ultra-high dose rate radiation by column to a target in a patient. Overlap between adjacent spots of the particle beam may be controlled in the treatment plan by controlling the current through the scanning magnet to position the spots at appropriate locations. In some implementations, use of slots may increase treatment speed and reduce the generation of stray neutrons that occurs when proton beams are trimmed.

Although the various implementations of the collimator described, for example, with respect to FIGS. 20 to 25 and 30 to 33 are described for use with ultra-high dose rate radiation treatment column-by-column, any implementation of such a collimator may be used in the delivery of doses of radiation that are not at ultra-high dose rates and/or that are not delivered in columns. For example, any collimator described herein may be used in implementing the layer-by-layer scanning approach described with respect to FIG. 1. Furthermore, the collimator implementations described show openings having the same shapes that are regularly arranged on a carrier. In some implementations, openings on the same carrier may have different sizes and/or shapes that may be dictated, for example, by the treatment plan. In addition, the openings may be arranged in an irregular pattern that may be dictated, for example, by the treatment plan. In some implementations, a carrier may include holes only, slots only, or a combination of both slots and holes. In some implementations, a carrier may have a single opening, such as a hole or a slot. The carrier and the particle beam may move in concert.

In some implementations, the example particle therapy system may include a configurable collimator instead of, or in addition to, the example collimators described with respect to FIGS. 20 to 25 and 30 to 33. An example of a configurable collimator that may be used is described in U.S. Patent Publication No. 2017/0128746 entitled "Adaptive Aperture", the contents of which are incorporated herein by reference.

Figure 46:
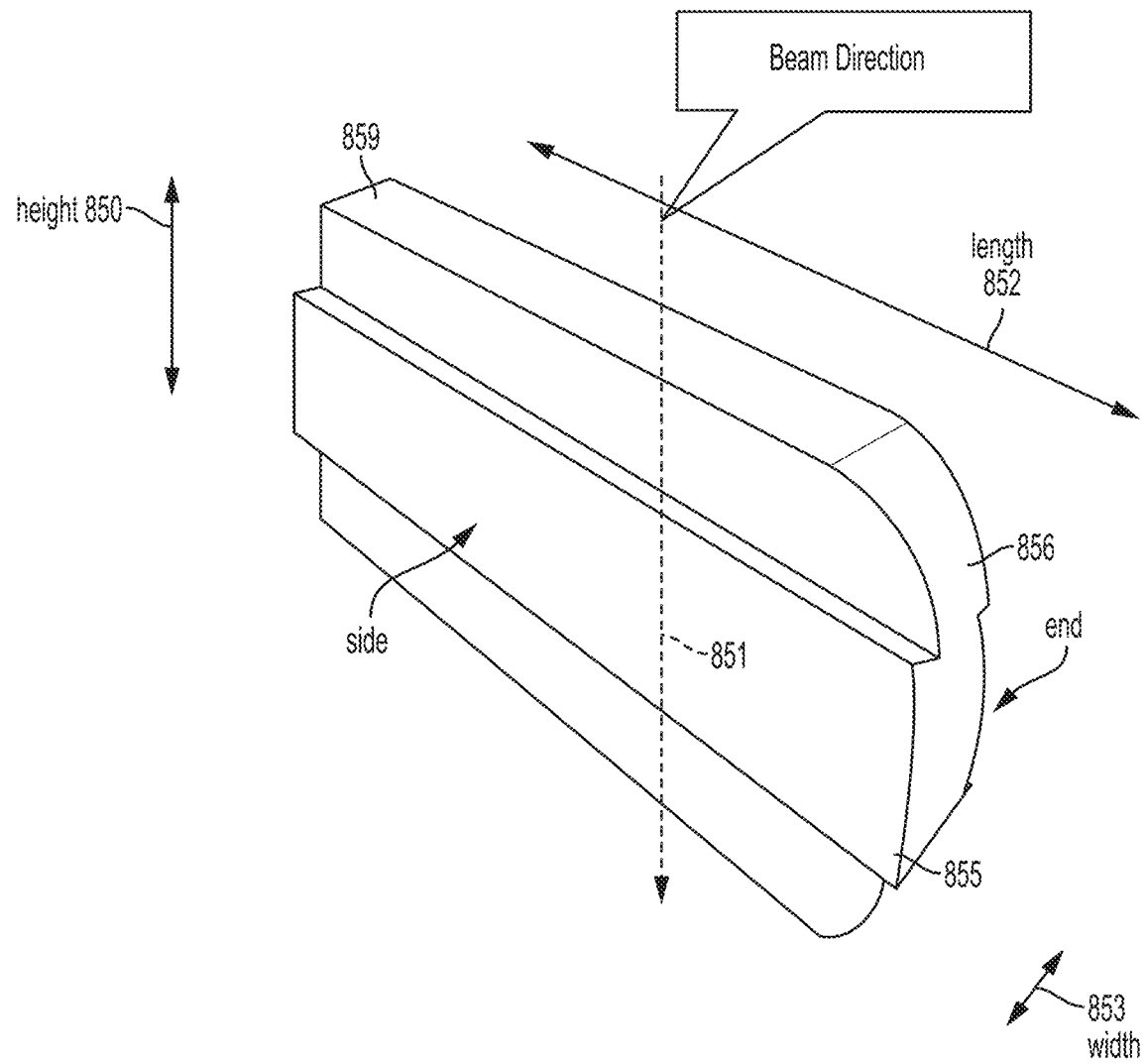
FIG. 46 is a perspective view of an example configurable collimator leaf that is usable with the example configurable collimators described herein.

FIG. 46 shows an example of a leaf 859 that may be used in the configurable collimator, although the configurable collimator is not limited to use with this type of leaf. The height 850 of the leaf is along the beam line (e.g., the direction of the particle beam). The length 852 of the leaf is along its direction of actuation into and out of the treatment area, and is based on the field size, or portion thereof, that the system can treat. The field size corresponds to the treatment area that the beam can impact. The width 853 of the leaf is the direction along which multiple leaves stack when actuated. Generally, the more leaves that are used, the higher the resolution of the aperture that can be produced, including for curved boundaries.

In FIG. 46, leaf 859 includes a tongue and groove feature 855 along its side, which is configured to reduce inter-leaf leakage when multiple such leaves stack. In this example, the curved end 856 of leaf 859 is configured to maintain a surface tangent to the beam at all locations in the treatment area. However, the end of each leaf may be flat, not curved.

In some implementations, the configurable collimator leaves have a height that is sufficient to block at least the maximum beam energy (e.g., the maximum energy of the particle beam output by the accelerator). In some implementations, the configurable collimator leaves have a height that blocks less than the maximum beam energy. In some implementations, the configurable collimator leaves have lengths that are dictated not by the area of an entire treatment area, but rather by the area of a single beam spot (the cross-sectional area of the particle beam) or multiple beam spots.

Figure 47:
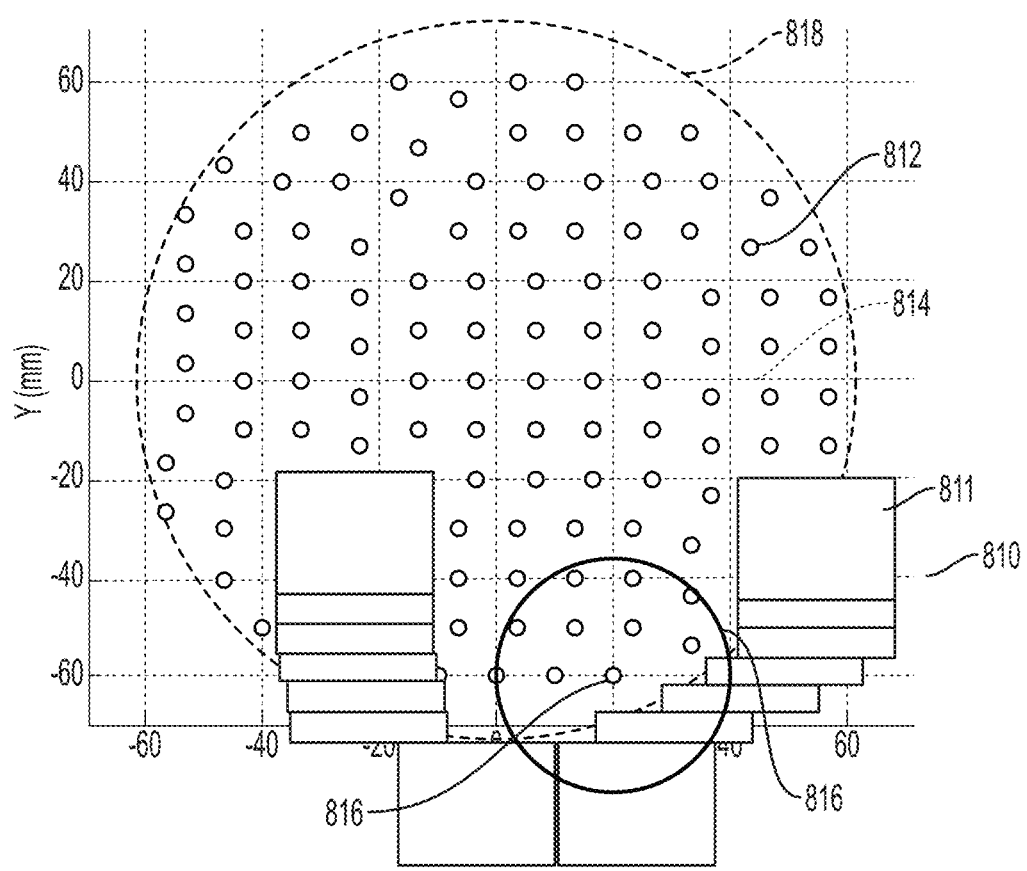
FIG. 47 is a top view of configurable collimator leaves positioned relative to a treatment area of an irradiation target.

FIG. 47 shows an example implementation of part a configurable collimator 810. Configurable collimator 810 includes leaves 811 having a height and made of a material, such as nickel, brass, tungsten, or other metal, sufficient to inhibit or prevent passage of radiation at a given energy. For example in some systems, a particle accelerator is configured to generate a particle beam having a maximum energy of 100 MeV (million electron-volts) to 300 MeV. Accordingly, in such systems, the leaves may be constructed to prevent passage of a beam having an energy of 100 MeV, 150 MeV, 200 MeV, 250 MeV, 300 MeV, and so forth. For example in some systems, a particle accelerator is configured to generate a particle beam having a maximum energy that exceeds 70 MeV. Accordingly, in such systems, the leaves may be constructed to prevent passage of a beam having an energy of 70 MeV or more.

Leaves 811 are mounted on carriages to control their movement relative to a treatment area of an irradiation target, such as a cross-sectional layer of a tumor in a patient. The movement is controlled to cause leaves 811 to cover some parts of treatment area 814, thereby preventing radiation from impacting those parts during treatment, while leaving other parts of the treatment area exposed to the radiation. In the example implementation of FIG. 47, there are fourteen leaves in total, seven on the left and seven on the right. In some implementations, there may be a different number of leaves, e.g., ten in total, five on the left and five on the right, twelve in total, six on the left and six on the right, and so forth.

In FIG. 47, locations 812 represent centers of beam spots and thus the locations of columns in the target to which radiation is to be delivered. Circle 818 represents parts of a treatment boundary beyond which no radiation is intended to be delivered. Beam spots that are close to this boundary (e.g., within one standard deviation of the particle beam's profile) border healthy tissue. These spots may be trimmed (that is, blocked) by appropriate configuration and placement of leaves on the configurable collimator. An example of a beam spot to be trimmed is beam spot 816, having its center at location 816. As shown, leaves 811 are configured to block the portion of beam spot 816 that extends beyond circle 818 and into healthy tissue (or at least tissue not designated for treatment).

In an example implementation, on each of two separate carriages, there are five leaves that are about 5 mm in width and two leaves that are about 81 mm in width. In some implementations, on each of two separate carriages, there are seven leaves, two of which each have widths that are three times or more the widths of each of five other leaves. Other implementations may contain different numbers, sizes, and configurations of leaves, and different numbers and configurations of carriages. For example, some implementations may include any number between five and fifty leaves per carriage, e.g., 5, 6, 7, 8, 9, 10, 11, 2, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 leaves (or more) per carriage.

The carriages can move both horizontally and vertically, as described herein. The leaves are also movable horizontally relative to each carriage into, and out of, the treatment area. In this way, the leaves are configurable to approximate the shape of the treatment boundary in the region near the area being treated (e.g., circle 816 or a portion thereof in this example).

The leaves may be moved vertically and/or horizontally between different columns to be treated so that the leaves are in appropriate positions when the beam is delivered to a particular column. As noted, the leaves may be reconfigured while the beam is stationary and based on beam energy to provide different configurations for different beam energies. As explained, the beam may disperse somewhat in tissue. The configurable collimator may be reconfigured as beam energy changes to maintain a regularly (e.g., cylindrically) shaped column.

Figure 49:
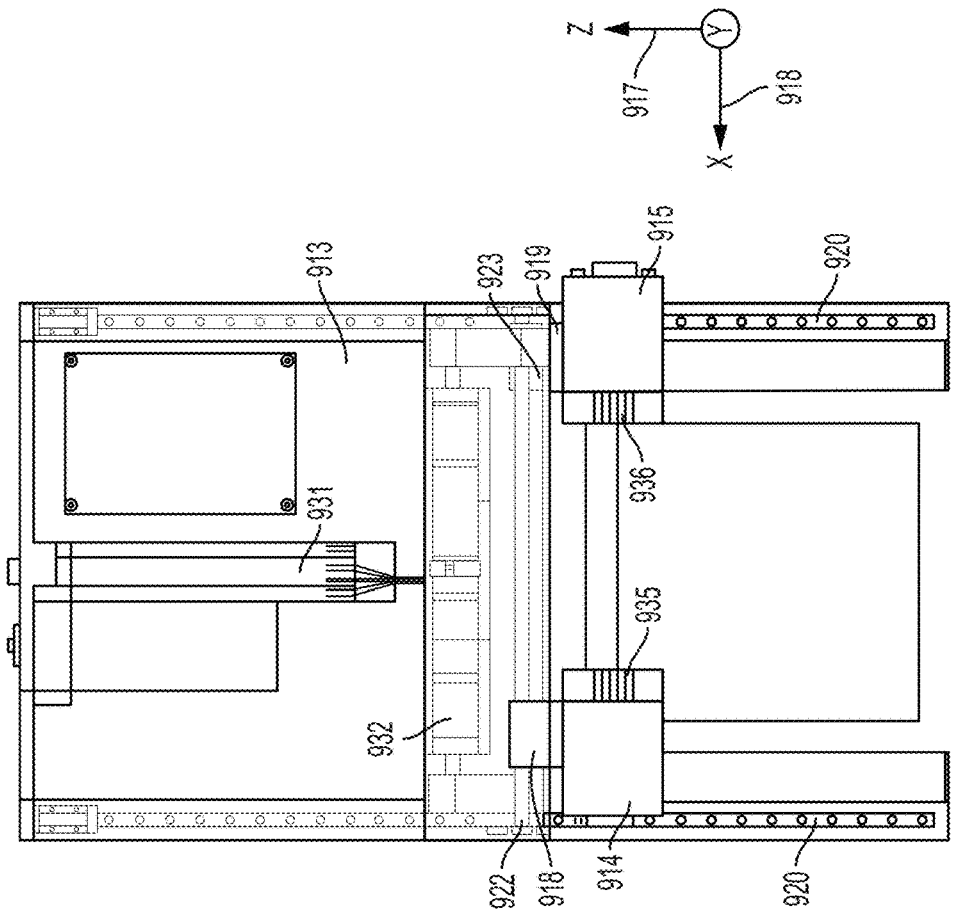
FIG. 49 is a front view of the example configurable collimator.
Figure 48:
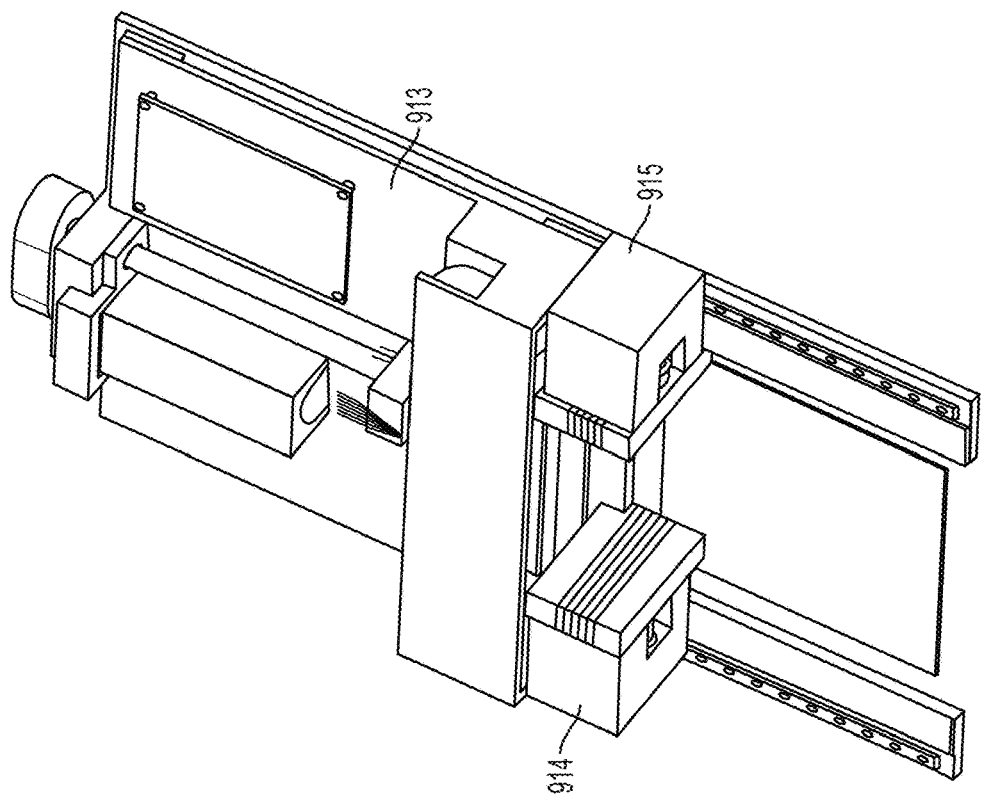
FIG. 48 is a perspective view of an example configurable collimator.
Figure 50:
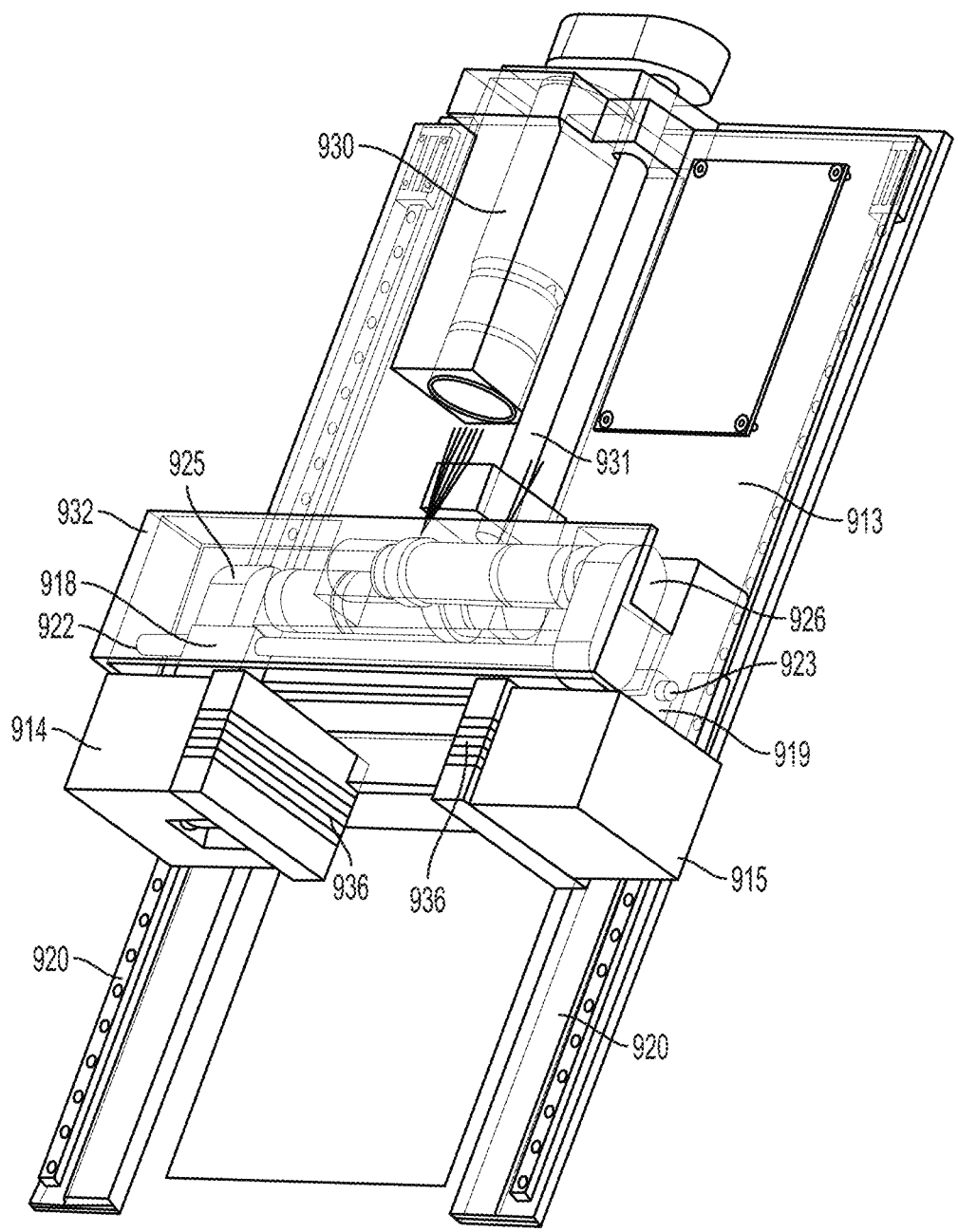
FIG. 50 is a perspective, view of the example configurable collimator having components portrayed in see-through to show the interiors thereof.

FIGS. 48, 49, and 50 show an example implementation of a configurable collimator, including carriages 913, 914, 915 configured to hold, and to move, the leaves described above both vertically and horizontally relative to the treatment target. As shown, vertical movement includes movement in the Cartesian Z-dimension 917, and horizontal movement includes movement in the Cartesian X dimension 918 (with the Cartesian Y dimension being into, or out of, the page in FIG. 49). FIGS. 49 and 50 show parts of carriage housings as transparent in order to show components inside the housings; however, the housings are not actually transparent.

Carriage 913 is referred to herein as the primary carriage, and carriages 914 and 915 are referred to herein as secondary carriages. Secondary carriages 914, 915 are coupled to primary carriage 913, as shown in FIGS. 48 to 50. In this example, secondary carriages 914, 915 each include a housing that is fixed to primary carriage 915 via a corresponding member 918, 919. In this example, primary carriage 913 is movable vertically (the Z dimension) relative to the irradiation target and relative to particle accelerator along tracks 920. The vertical movement of primary carriage 913 also causes the secondary carriages to move vertically. In some implementations, the secondary carriages move vertically in concert. In some implementations, vertical movement of each secondary carriage is independent of vertical movement of the other secondary carriage.

As shown in FIGS. 48 to 50, each secondary carriage 914, 915 is connected to a corresponding rod or rail 922, 923, along which the secondary carriage moves. More specifically, in this example, motor 925 drives secondary carriage 914 to move along rod 922 towards or away from secondary carriage 915. Likewise, in this example, motor 926 drives secondary carriage 915 to move along rod 923 towards or away from secondary carriage 914. Control over movement of the primary and secondary carriages is implemented to position the leaves relative to the irradiation target, as described herein. In addition, the leaves themselves are also configured to move in and out of the carriages, as also described herein.

As shown in FIG. 50, a motor 930 drives the vertical movement of primary carriage 913. For example, as shown in FIG. 50, lead screw 931 is coupled to housing 932, which holds motors 925, 926 that drive corresponding secondary carriages 914, 915, and which is mounted on tracks 920. Lead screw 931 is coupled to, and driven vertically by, motor 930. That is, motor 930 drives lead screw 931 vertically (the Cartesian Z dimension). Because lead screw 931 is fixed to housing 932, this movement also causes housing 932, and thus secondary carriages 914, 915, to move along tracks 920, either towards or away from the irradiation target.

In this example implementation, as noted, seven leaves 935, 936 are mounted on each secondary carriage 914, 915. Each secondary carriage may be configured to move its leaves horizontally into, or out of, the treatment area. The individual leaves on each secondary carriage may be independently and linearly movable using linear motors in the X dimension relative to other leaves on the same secondary carriage. In some implementations, the leaves may also be configured to move in the Y dimension. Furthermore, the leaves on one secondary carriage 914 may be movable independently of the leaves on the other secondary carriage 915. These independent movements of leaves on the secondary carriages, together with the vertical movements enabled by the primary carriage, allow the leaves to be moved into various configurations. As a result, the leaves can conform, both horizontally and vertically, to treatment areas that are randomly shaped both in horizontal and vertical dimensions. The sizes and shapes of the leaves may be varied to create different conformations. For example, the sizes and shapes may be varied to treat a single beam spot and, thus, a single column. In some implementations individual leaves on each secondary carriage may be independently and linearly movable using electric motors that drive lead screws in the X dimension relative to other leaves on the same secondary carriage.

The leaves may be made of any appropriate material that prevents or inhibits transmission of radiation. The type of radiation used may dictate what material(s) are used in the leaves. For example, if the radiation is X-ray, the leaves may be made of lead. In the examples described herein, the radiation is a proton or ion beam. Accordingly, different types of metals or other materials may be used for the leaves. For example, the leaves may be made of nickel, tungsten, lead, brass, steel, iron, or any appropriate combinations thereof. The height of each leaf may determine how well that leaf inhibits transmission of radiation.

In some implementations, the leaves may have the same height, whereas in other implementations, some of the leaves may have heights that are different from heights of others of the leaves. For example, a set of leaves may each be 5 mm in height. However, any appropriate heights may be used. For example, leaves 935, 936 may have any of the following (or other heights): 1 mm, 2 mm, 3 mm, 4 mm, 5 mm, 6 mm, 7 mm, 8 mm, 9 mm, 10 mm, 11 mm, 3 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, and so forth. The leaves may have any combination of the foregoing heights. In addition, each of the leaves may have a different height than one or more others of the leaves.

In some implementations, the leaves have heights that are enough not only to fully stop a particle beam at the maximum expected proton energy (e.g., 3.3 cm of Tungsten at 230 MeV or, e.g., 5.2 cm of nickel), but also to have enough extra material to prevent proton transmission between the leaves. This material may have a tongue and groove structure as shown in FIG. 46, or a similar configuration. The leaf ends may be configured to include curved or tapered surfaces to enhance delivered penumbra for proton beams of various divergence.

In some implementations, there may be more than one primary carriage and corresponding motors and rails. For example, a first primary carriage may control vertical movement of a first secondary carriage, and a second primary carriage may control vertical movement of a second secondary carriage. Therefore, in such implementations, the two secondary carriages can be moved independently in the vertical dimension, if desired. In any case, the primary carriage may be computer controlled. For example, executable instructions are stored in computer memory (e.g., one or more non-transitory machine-readable storage media), and executed by one or more processing devices to control the movement. Control may be performed with, or without, user input during treatment.

As explained, each secondary carriage 914, 915 includes a corresponding motor to control horizontal carriage movement, as described above. In some implementations, all leaves on a single carriage are independently movable using linear motors—with one linear motor controlling each leaf. Each leaf may be controlled by a linear motor of the type described in FIG. 10 to create an edge to block at least some radiation from reaching the patient, e.g., to trim one or more spots produced by the particle beam. As noted, a linear motor used in the configurable collimator may have the same structure and function as a linear motor used with the range modulator. In this case, however, the collimator leaf is attached to the linear motor instead of an energy-absorbing plate. Each linear motor drives its corresponding leaf linearly to reach its position in a configured edge.

In the example implementations described above, each leaf is independently actuated using a separate, and independently-controllable, linear motor such that any appropriate shape can be traced with a leaf configuration. It may be, however, that such flexibility is not required to achieve acceptable edge conformality. The leaves could be mechanically constrained with the ability to achieve only a finite number of configurations. For example, the leaves could be restricted to arrangements that put them in a vertical line, forward diagonal shape, backward diagonal shape, concave shape, convex shape, or any other achievable shape. In this way, flexibility could be traded for mechanical simplicity.

In some cases, better beam performance (penumbra or edge sharpness) results when the particle beam is tangent to the surface of a leaf edge. However, since the beam effectively originates from a single point source, the angle with which it passes through the plane of the configurable collimator changes as the beam is moved away from the center of the field. For this reason, leaves may have curved edges, as shown in FIG. 46, so that the edges can always be placed a location that makes them tangent to the particle beam. In an example implementation of the configurable collimator, the tracks on which both primary and secondary carriages move are curved so that flat leaf edges can be used in lieu of curved leaf edges, and so that the flat but remain tangent to the particle beam.

To summarize, in some implementations, the configurable collimator may have a relatively small size, at least in part due to the linear motors described herein. Thus, in contrast to standard multi-leaf collimators, an example configurable collimator may therefore be used to trim a fraction of a treatment area at one time, e.g., an area that is less than the entire treatment area and that is about equal to one spot size, two spot sizes, three spot sizes, four spot sizes, five spot sizes, and so forth. Thus, in some implementations, the configurable collimator may be small enough to trim a single spot at once and may be large enough to trim several spots in one position, but not the entire field without moving. As noted, the ability to trim a single spot may be used to maintain a regular shape of a treatment column as the energy of the particle beam used to create that column varies.

Figure 51:
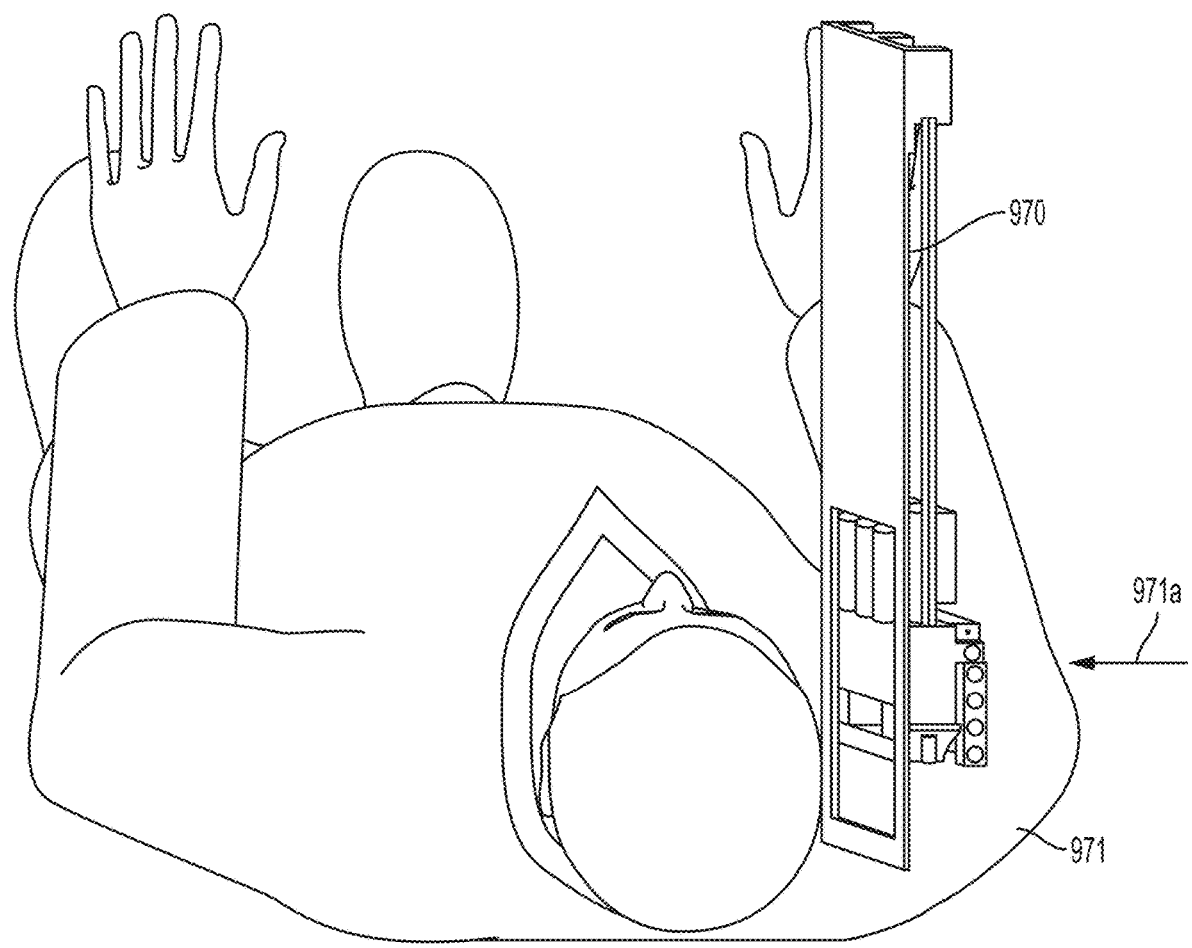
FIG. 51 is a perspective view of the example configurable collimator positioned relative to a patient during particle therapy treatment.

The scanning system may include the configurable collimator described herein, which is placeable relative to the irradiation target to limit the extent of the particle beam and thereby limit the extent of the particle beam. For example, the configurable collimator may be placed in the beam path down-beam of the energy degrader and before the particle beam hits the treatment area of the irradiation target. The configurable collimator is controllable to allow the particle beam to pass therethrough and then hit certain parts of the treatment area, while preventing the particle beam from hitting other parts of the patient. FIG. 51 depicts placement of an implementation of the configurable collimator 970 relative to a patient 971. The direction of beam 971a is also shown.

FIGS. 26 and 27 show parts an example of a proton therapy system 1082 containing a particle accelerator mounted on a gantry. Because the accelerator is mounted on the gantry it is in or adjacent to the treatment room. The particle accelerator may be the synchrocyclotron of FIG. 3; however, the system is not limited to use with synchrocyclotrons. The gantry and the particle accelerator may be controlled, along with the scanning system, to treat columns of an irradiation target using ultra-high dose rate radiation in the manner described herein. In some implementations, the gantry is steel and has two legs (not shown) mounted for rotation on two respective bearings that lie on opposite sides of a patient. The gantry may include a steel truss (not shown) that is connected to each of its legs, that is long enough to span a treatment area in which the patient lies, and that is attached at both ends to the rotating legs of the gantry. The particle accelerator may be supported by the steel truss for motion around the patient.

In the example of FIGS. 26 and 27, the patient is located on a treatment couch 1084. In this example, treatment couch 1084 includes a platform that supports the patient. The platform also may include one or more restraints (not shown) for holding the patient in place and for keeping the patient substantially immobile during movement of the couch and during treatment. The platform may, or may not, be padded and/or have a shape (e.g., an indentation) that corresponds to the shape of part of the patient. The couch may be moved via arm 1085.

FIG. 28 shows an example of the gantry configuration described in U.S. Pat. No. 7,728,311 incorporated herein by reference, and includes components of an alternative implementation of a proton therapy system that usable to treat columns of an irradiation target using ultra-high dose rate radiation in the manner described herein. The example proton therapy system of FIG. 28 includes an inner gantry 1190 having a nozzle 1191, a treatment couch 1192, and a particle accelerator 1193 (e.g., a synchrocyclotron of the type described herein) mounted on an outer gantry 1194 for rotation at least part-way around the patient to deliver radiation to target(s) in the patient. Treatment couch 1192 is controllable and configured to rotate and to translate the patient in the manner described herein.

In the example of FIG. 28, particle accelerator 1193 is also mounted to outer gantry 1194 also to enable linear movement (e.g., translational movement) of the particle accelerator in the directions of arrow 1195 along arms 1196. As also shown in FIG. 28, the particle accelerator 1193 may be connected to a gimbal 1199 for pivoting motion relative to the gantry. This pivoting motion may be used to position the accelerator, and thus the beam, for treatment.

Components of the scanning system including the scanning magnet, the ion chamber, the range modulator, and the collimator may be mounted on, in, or coupled to a nozzle 1081, 1191 of the proton therapy system's inner gantry. These components may be controlled by the control system to treat columns of an irradiation target using ultra-high dose rate radiation. In both examples, the nozzle is movable along a track of the inner gantry (1080 or 1190) relative to the patient and the particle accelerator, and is extensible towards, and retractable away from, the patient, thereby also extending and retracting the components mounted thereon.

In some implementations, the synchrocyclotron used in the proton therapy system described herein may be a variable-energy synchrocyclotron. In some implementations, a variable-energy synchrocyclotron is configured to vary the energy of the output particle beam by varying the magnetic field in which the particle beam is accelerated. For example, the current may be set to any one of multiple values to produce a corresponding magnetic field. In an example implementation, one or more sets of superconducting coils receives variable electrical current to produce a variable magnetic field in the cavity. In some examples, one set of coils receives a fixed electrical current, while one or more other sets of coils receives a variable current so that the total current received by the coil sets varies. In some implementations, all sets of coils are superconducting. In some implementations, some sets of coils, such as the set for the fixed electrical current, are superconducting, while other sets of coils, such as the one or more sets for the variable current, are non-superconducting (e.g., copper) coils.

Generally, in a variable-energy synchrocyclotron, the magnitude of the magnetic field is scalable with the magnitude of the electrical current. Adjusting the total electric current of the coils in a predetermined range can generate a magnetic field that varies in a corresponding, predetermined range. In some examples, a continuous adjustment of the electrical current can lead to a continuous variation of the magnetic field and a continuous variation of the output beam energy. Alternatively, when the electrical current applied to the coils is adjusted in a non-continuous, step-wise manner, the magnetic field and the output beam energy also varies accordingly in a non-continuous (step-wise) manner. The scaling of the magnetic field to the current can allow the variation of the beam energy to be carried out relatively precisely, thus reducing the need for an energy degrader. An example of a variable-energy synchrocyclotron that may be used in the particle therapy systems described herein is described in U.S. Pat. No. 9,730,308 entitled "Particle Accelerator That Produces Charged Particles Having Variable Energies", the contents of which are incorporated herein by reference.

In implementations of the particle therapy system that use a variable-energy synchrocyclotron, controlling the energy of the particle beam to treat a column of the target may be performed by changing the energy of the particle beam output by the synchrocyclotron. In such implementations, a range modulator may or may not be used. For example, controlling the energy of the particle beam may include setting the current in the synchrocyclotron main coils to one of multiple values, each which corresponds to a different energy at which the particle beam is output from the synchrocyclotron. A range modulator may be used along with a variable-energy synchrocyclotron to provide additional changes in energy, for, example, between discrete energy levels provided by the synchrocyclotron.

In some implementations, a particle accelerator other than a synchrocyclotron may be used in the particle therapy system described herein. For example, a cyclotron, a synchrotron, a linear accelerator, or the like may be substituted for the synchrocyclotron described herein. Although a rotational gantry has been described (e.g., the outer gantry), the example particle therapy systems described herein are not limited to use with rotational gantries. Rather, a particle accelerator may be mounted, as appropriate, on any type of robotic or other controllable mechanism(s)—characterized herein also as types of gantries—to implement movement of the particle accelerator. For example, the particle accelerator may be mounted on or more robotic arms to implement rotational, pivotal, and/or translational movement of the accelerator relative to the patient. In some implementations, the particle accelerator may be mounted on a track, and movement along the track may be computer-controlled. In this configuration, rotational and/or translational and/or pivotal movement of the accelerator relative to the patient can also be achieved through appropriate computer control. In some implementations, the particle accelerator may be stationary and located outside the treatment room, with the beam being delivered to a nozzle in the treatment room.

In some examples, as noted above, ultra-high dose rates of radiation may include doses of radiation that exceed 1 Gray-per-second for a duration of less than 500 ms. In some examples, ultra-high dose rates of radiation may include doses of radiation that exceed 1 Gray-per-second for a duration that is between 10 ms and 5 s. In some examples, ultra-high dose rates of radiation may include doses of radiation that exceed 1 Gray-per-second for a duration that is less than 5 s.

In some examples, ultra-high dose rates of radiation include doses of radiation that exceed one of the following doses for a duration of less than 500 ms: 2 Gray-per-second, 3 Gray-per-second, 4 Gray-per-second, 5 Gray-per-second, 6 Gray-per-second, 7 Gray-per-second, 8 Gray-per-second, 9 Gray-per-second, 10 Gray-per-second, 11 Gray-per-second, 12 Gray-per-second, 13 Gray-per-second, 14 Gray-per-second, 15 Gray-per-second, 16 Gray-per-second, 17 Gray-per-second, 18 Gray-per-second, 19 Gray-per-second, 20 Gray-per-second, 30 Gray-per-second, 40 Gray-per-second, 50 Gray-per-second, 60 Gray-per-second, 70 Gray-per-second, 80 Gray-per-second, 90 Gray-per-second, or 100 Gray-per-second. In some examples, ultra-high dose rates of radiation include doses of radiation that exceed one of the following doses for a duration that is between 10 ms and 5 s: 2 Gray-per-second, 3 Gray-per-second, 4 Gray-per-second, 5 Gray-per-second, 6 Gray-per-second, 7 Gray-per-second, 8 Gray-per-second, 9 Gray-per-second, 10 Gray-per-second, 11 Gray-per-second, 12 Gray-per-second, 13 Gray-per-second, 14 Gray-per-second, 15 Gray-per-second, 16 Gray-per-second, 17 Gray-per-second, 18 Gray-per-second, 19 Gray-per-second, 20 Gray-per-second, 30 Gray-per-second, 40 Gray-per-second, 50 Gray-per-second, 60 Gray-per-second, 70 Gray-per-second, 80 Gray-per-second, 90 Gray-per-second, or 100 Gray-per-second. In some examples, ultra-high dose rates of radiation include doses of radiation that exceed one of the following doses for a duration that is less than 5 s: 2 Gray-per-second, 3 Gray-per-second, 4 Gray-per-second, 5 Gray-per-second, 6 Gray-per-second, 7 Gray-per-second, 8 Gray-per-second, 9 Gray-per-second, 10 Gray-per-second, 11 Gray-per-second, 12 Gray-per-second, 13 Gray-per-second, 14 Gray-per-second, 15 Gray-per-second, 16 Gray-per-second, 17 Gray-per-second, 18 Gray-per-second, 19 Gray-per-second, 20 Gray-per-second, 30 Gray-per-second, 40 Gray-per-second, 50 Gray-per-second, 60 Gray-per-second, 70 Gray-per-second, 80 Gray-per-second, 90 Gray-per-second, or 100 Gray-per-second.

In some examples, ultra-high dose rates of radiation include doses of radiation that exceed one or more of the following doses for a duration of less than 500 ms, for a duration that is between 10 ms and 5 s, or for a duration that is less than 5 s: 100 Gray-per-second, 200 Gray-per-second, 300 Gray-per-second, 400 Gray-per-second, or 500 Gray-per-second.

In some examples, ultra-high dose rates of radiation include doses of radiation that are between 20 Gray-per-second and 100 Gray-per-second for a duration of less than 500 ms. In some examples, ultra-high dose rates of radiation include doses of radiation that are between 20 Gray-per-second and 100 Gray-per-second for a duration that is between 10 ms and 5 s. In some examples, ultra-high dose rates of radiation include doses of radiation that are between 20 Gray-per-second and 100 Gray-per-second for a duration that is less than 5 s. In some examples, ultra-high dose rate rates of radiation include doses of radiation that are between 40 Gray-per-second and 120 Gray-per-second for a time period such as less than 5 s. Other examples of the time period are those provided above.

In some implementations, the size, the shape, or the size and shape of the holes in the collimators described herein may be changeable or otherwise configurable—for example, one or more of the hole or slot locations may be moved. For example, one or more of the holes or slots may be formed using fingers or leaves mounted on one or more carriages as described, for example, in U.S. Patent Application No. 2017/0128746 titled "Adaptive Aperture".

Operation of the example proton therapy systems described herein, and operation of all or some component thereof, can be controlled (as appropriate), at least in part, using one or more computer program products, e.g., one or more computer programs tangibly embodied in one or more non-transitory machine-readable media, for execution by, or to control the operation of, one or more data processing apparatus, e.g., a programmable processor, a computer, multiple computers, and/or programmable logic components.

A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a network.

Actions associated with controlling all or part of the operations of the example proton therapy systems described herein can be performed by one or more programmable processors executing one or more computer programs to perform the functions described herein. All or part of the operations can be controlled using special purpose logic circuitry, e.g., an FPGA (field programmable gate array) and/or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only storage area or a random access storage area or both. Elements of a computer (including a server) include one or more processors for executing instructions and one or more storage area devices for storing instructions and data. Generally, a computer will also include, or be operatively coupled to receive data from, or transfer data to, or both, one or more machine-readable storage media for storing data, e.g., magnetic, magneto-optical disks, or optical disks. Non-transitory machine-readable storage media suitable for storing computer program instructions and data include all forms of non-volatile storage area, including by way of example, semiconductor storage area devices, e.g., EPROM, EEPROM, and flash storage area devices; magnetic disks, e.g., internal hard disks or removable disks; magneto-optical disks; and CD-ROM and DVD-ROM disks.

Any two more of the foregoing implementations may be used in an appropriate combination with an appropriate particle accelerator (e.g., a synchrocyclotron). Likewise, individual features of any two more of the foregoing implementations may be used in an appropriate combination. Elements may be left out of the processes, systems, apparatus, etc., described herein without adversely affecting their operation. Various separate elements may be combined into one or more individual elements to perform the functions described herein.

What is claimed is:

1. A system comprising:
    a particle accelerator to apply a particle beam to treat an irradiation target in a patient located in a treatment room, the irradiation target comprising multiple sub-volumes, the particle beam being applied to the irradiation target at an ultra-high dose rate;
    an energy degrader comprising:
        multiple structures, each structure of the multiple structures for changing an energy of the particle beam as the particle beam passes through the structure, each structure of the multiple structures comprising boron carbide; and
        actuators, each actuator for controlling movement of a corresponding one of the multiple structures into and out of a beam field of the particle beam;
        wherein the energy degrader is located in the treatment room; and
    a control system configured to perform operations comprising: (A) prior to application of the particle beam to a sub-volume of the irradiation target, controlling the energy degrader to move one or more of the multiple structures from a retracted position outside of the beam field to a pre-position within the beam field that is proximate to the sub-volume, and (B) after the one or more of the multiple structures are at the pre-position, controlling the one or more of the multiple structures to move between (i) the pre-position and (ii) a location between a beamline of the particle accelerator and the sub-volume so that the one or more of the multiple structures are between the particle beam and the sub-volume during application of the particle beam to the sub-volume.

2. The system of claim 1, wherein each structure comprises a plate.

3. The system of claim 1, wherein each structure comprises a polyhedron.

4. The system of claim 1, wherein each structure is pure boron carbide.

5. The system of claim 1, wherein one or more of the multiple structures comprises a composite material comprised of boron carbide and graphite.

6. The system of claim 1, wherein the energy degrader is located no more than three meters from the patient along the beamline.

7. The system of claim 1, wherein the energy degrader is located no more than two meters from the patient along the beamline.

8. The system of claim 1, wherein the energy degrader is located no more than one meter from the patient along the beamline.

9. The system of claim 1, further comprising:
    a scanning magnet to move the particle beam relative to the patient;
    wherein the energy degrader is located between the scanning magnet and the patient.

10. The system of claim 1, wherein the ultra-high dose rate comprises a dose rate that exceeds 1 Gray-per-second for a duration of less than 5 seconds.

11. The system of claim 1, wherein the ultra-high dose rate comprises a dose rate that is between 20 Gray-per-second and 100 Gray-per-second for a duration that is between 10 milliseconds and 5 seconds.

12. The system of claim 1, wherein the ultra-high dose rate comprises a dose rate that is between 40 Gray-per-second and 120 Gray-per-second for a duration of less than 5 seconds.

13. The system of claim 1, wherein controlling the one or more of the multiple structures to move between (i) the pre-position and (ii) the location comprises controlling one or more of the multiple structures to move while the particle beam is stationary.

14. The system of claim 1, wherein the actuators comprises linear motors.

15. The system of claim 1, wherein the control system is configured to control the energy degrader to move one or more of the multiple structures into, or out of, the beamline in a duration of 50 milliseconds or less.

16. A system comprising:
a particle accelerator to apply a particle beam to treat an irradiation target in a patient located in a treatment room, the irradiation target comprising multiple sub-volumes, the particle beam being applied to the irradiation target at an ultra-high dose rate; and
an energy degrader comprising:
multiple structures, each structure of the multiple structures for changing an energy of the particle beam as the particle beam passes through the structure, each structure of the multiple structures comprising boron carbide; and
actuators for controlling movement of the multiple structures into and out of a beam field of the particle beam;
wherein the energy degrader is located no more than four meters from the patient along a beamline; and
a control system configured to perform operations comprising: (A) prior to application of the particle beam to a sub-volume of the irradiation target, controlling the energy degrader to move one or more of the multiple structures from a retracted position outside of the beam field to a pre-position within the beam field that is proximate to the sub-volume, and (B) after the one or more of the multiple structures are at the pre-position, controlling the one or more of the multiple structures to move between (i) the pre-position and (ii) a location between a beamline of the particle accelerator and the sub-volume so that the one or more of the multiple structures are between the particle beam and the sub-volume during application of the particle beam to the sub-volume.

17. The system of claim 16, wherein controlling the one or more of the multiple structures to move between (i) the pre-position and (ii) the location comprises controlling the one or more of the multiple structures to move while the particle beam is stationary.

18. The system of claim 16, wherein the energy degrader is located no more than three meters from the patient along the beamline.

19. The system of claim 16, wherein the energy degrader is located no more than two meters from the patient along the beamline.

20. The system of claim 16, wherein the energy degrader is located no more than one meter from the patient along the beamline.

21. The system of claim 16, wherein the control system is configured to control the energy degrader to move one or more of the multiple structures into, or out of, the beamline in a duration of 50 milliseconds or less.

* * * * *